US011377485B2

(12) United States Patent
Wong et al.

(10) Patent No.: US 11,377,485 B2
(45) Date of Patent: *Jul. 5, 2022

(54) METHODS FOR MODIFYING HUMAN ANTIBODIES BY GLYCAN ENGINEERING

(71) Applicant: Academia Sinica, Taipei (TW)

(72) Inventors: Chi-Huey Wong, La Jolla, CA (US); Chung-Yi Wu, Taipei (TW)

(73) Assignee: ACADEMIA SINICA, Taipei (TW)

( * ) Notice: Subject to any disclaimer, the term of this patent is extended or adjusted under 35 U.S.C. 154(b) by 379 days.

This patent is subject to a terminal disclaimer.

(21) Appl. No.: 16/150,164

(22) Filed: Oct. 2, 2018

(65) Prior Publication Data

US 2019/0194303 A1 Jun. 27, 2019

Related U.S. Application Data

(63) Continuation-in-part of application No. 12/959,351, filed on Dec. 2, 2010, now Pat. No. 10,087,236.

(60) Provisional application No. 61/265,757, filed on Dec. 2, 2009.

(51) Int. Cl.
C07K 16/18 (2006.01)
C12P 21/00 (2006.01)
C07K 16/28 (2006.01)

(52) U.S. Cl.
CPC .......... C07K 16/18 (2013.01); C07K 16/2887 (2013.01); C12P 21/005 (2013.01); C07K 2317/24 (2013.01); C07K 2317/41 (2013.01); C07K 2317/50 (2013.01); C12Y 204/01 (2013.01); C12Y 204/99001 (2013.01); C12Y 204/99003 (2013.01); C12Y 204/99004 (2013.01)

(58) Field of Classification Search
CPC .............. C12P 21/005; C07K 2317/41; C12Y 204/01; C12Y 204/99001; C12Y 204/99003; C12Y 204/99004
USPC ...................................................... 530/387.3
See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,270,537 A | 6/1981 | Romaine |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,376,110 A | 3/1983 | David et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,596,556 A | 6/1986 | Morrow et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |

(Continued)

FOREIGN PATENT DOCUMENTS

| | | | | |
|---|---|---|---|---|
| CA | 002950423 A1 | * | 12/2015 | ......... C07K 16/1018 |
| CN | 101855339 A | | 10/2010 | |

(Continued)

OTHER PUBLICATIONS

Dissertation, ChongQing Medical University, "Characterization and Culture of Microspheres Isolated Directly From Tumor/Tissues of Breast Cancer Patients Received Neoadjuvant Chemotherapy" May 2011, 120 pages; English translation of Abstract provided.
Extended European Search Report dated Oct. 10, 2019 in European Patent Application No. 17764050.5, in 11 pages.
Horton, Holly M., et al. "Potent in vitro and in vivo activity of an Fc-engineered anti-CD19 monoclonal antibody against lymphoma and leukemia." Cancer Research 68.19 (2008): 8049-8057.
Lazar, Greg A., et al. "Engineered antibody Fc variants with enhanced effector function." Proceedings of the National Academy of Sciences 103.11 (2006): 4005-4010.

(Continued)

Primary Examiner — Lynn A Bristol
(74) Attorney, Agent, or Firm — Ladas & Parry LLP

(57) ABSTRACT

Methods for making modified Fc regions of antibodies and antibody fragments, both human and humanized, and having enhanced stability and efficacy, are provided. Antibodies comprising Fc regions with core fucose residues removed, and attached to oligosaccharides comprising terminal sialyl residues, are provided. Antibodies comprising homogeneous glycosylation of Fc regions with specific oligosaccharides are provided. Fc regions conjugated with homogeneous glycoforms of monosaccharides and trisaccharides, are provided. Methods of preparing human antibodies with modified Fc using glycan engineering, are provided.

36 Claims, 11 Drawing Sheets
(6 of 11 Drawing Sheet(s) Filed in Color)
Specification includes a Sequence Listing.

(56) References Cited

U.S. PATENT DOCUMENTS

| | | |
|---|---|---|
| 4,741,900 A | 5/1988 | Alvarez et al. |
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Darfler |
| 4,940,460 A | 7/1990 | Casey et al. |
| 4,941,880 A | 7/1990 | Burns |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |
| 5,064,413 A | 11/1991 | McKinnon et al. |
| 5,075,109 A | 12/1991 | Tice et al. |
| 5,079,233 A | 1/1992 | Lee |
| 5,100,669 A | 3/1992 | Hyon et al. |
| 5,112,596 A | 5/1992 | Malfroy-Camine |
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A | 11/1994 | Wong et al. |
| 5,374,541 A | 12/1994 | Wong et al. |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Cater et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A | 12/1998 | Akimoto |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,399,071 B1 | 6/2002 | Duthaler |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |
| 6,994,966 B2 | 2/2006 | Dukler |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |
| 7,205,333 B2 | 4/2007 | Wu et al. |
| 7,488,491 B2 | 2/2009 | Tsjui et al. |
| 7,498,298 B2 | 3/2009 | Doronina et al. |
| 7,592,004 B2 | 9/2009 | Kaisheva et al. |
| 7,854,934 B2 | 12/2010 | Danishefsky |
| 7,888,337 B2 | 2/2011 | Wong et al. |
| 7,923,013 B2 | 4/2011 | Tsuji et al. |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 | 9/2011 | Porcelli |
| 8,088,387 B2 | 1/2012 | Steeves et al. |
| 8,101,179 B2 | 1/2012 | Numazaki et al. |
| 8,163,290 B2 | 4/2012 | Tsuji et al. |
| 8,268,969 B2 | 9/2012 | Wong et al. |
| 8,383,554 B2 | 2/2013 | Wong et al. |
| 8,507,660 B2 | 8/2013 | Wong et al. |
| 8,680,020 B2 | 3/2014 | Wong et al. |
| 8,715,963 B2 | 5/2014 | Sethuraman |
| 8,716,465 B2 | 5/2014 | Rossi et al. |
| 8,765,390 B2 | 7/2014 | Allies et al. |
| 8,802,438 B2 | 8/2014 | Rossi et al. |
| 8,815,941 B2 | 8/2014 | Withers |
| 8,883,506 B2 | 11/2014 | Rossi et al. |

(56) References Cited

U.S. PATENT DOCUMENTS

| | | |
|---|---|---|
| 8,906,832 B2 | 12/2014 | Wong et al. |
| 8,907,111 B2 | 12/2014 | Withers |
| 9,187,552 B2 | 11/2015 | Stadheim |
| 9,221,859 B2 | 12/2015 | Withers |
| 9,382,284 B2 | 7/2016 | Withers |
| 9,403,855 B2 | 8/2016 | Wong et al. |
| 9,434,786 B2 | 9/2016 | Wang |
| 9,547,009 B2 | 1/2017 | Wong et al. |
| 9,566,282 B2 | 2/2017 | Bhatia et al. |
| 9,759,726 B2 | 9/2017 | Wong et al. |
| 9,782,476 B2 | 10/2017 | Wong et al. |
| 9,803,177 B2 | 10/2017 | Rossi et al. |
| 9,874,562 B2 | 1/2018 | Wong et al. |
| 9,879,042 B2 | 1/2018 | Wong et al. |
| 9,914,956 B2 | 3/2018 | Wong et al. |
| 9,975,965 B2 | 5/2018 | Wong et al. |
| 9,981,030 B2 | 5/2018 | Wong et al. |
| 9,982,041 B2 | 5/2018 | Wong et al. |
| 10,005,847 B2 * | 6/2018 | Wong ................... C12P 21/005 |
| 10,023,892 B2 * | 7/2018 | Wong ................... A61K 39/42 |
| 10,086,054 B2 | 10/2018 | Wong et al. |
| 10,087,236 B2 | 10/2018 | Wong et al. |
| 10,111,951 B2 | 10/2018 | Wong et al. |
| 10,118,969 B2 * | 11/2018 | Wong ................. C07K 16/2887 |
| 10,119,972 B2 | 11/2018 | Wong et al. |
| 10,130,714 B2 | 11/2018 | Wong et al. |
| 10,150,818 B2 | 12/2018 | Wong et al. |
| 10,214,765 B2 | 2/2019 | Wong et al. |
| 10,336,784 B2 | 7/2019 | Wong et al. |
| 10,538,592 B2 | 1/2020 | Lin et al. |
| 10,618,973 B2 | 4/2020 | Wong et al. |
| 10,918,714 B2 | 2/2021 | Wong et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0118592 A1 | 6/2003 | Ledbetter et al. |
| 2003/0129186 A1 | 7/2003 | Beliveau et al. |
| 2003/0162695 A1 | 8/2003 | Schatzberg et al. |
| 2003/0175884 A1 | 9/2003 | Umana et al. |
| 2003/0219433 A1 | 11/2003 | Hansen et al. |
| 2004/0072290 A1 | 4/2004 | Umana et al. |
| 2004/0086423 A1 | 5/2004 | Wohlstadter |
| 2004/0131692 A1 | 7/2004 | Kreuter et al. |
| 2004/0137557 A1 | 7/2004 | DeFrees et al. |
| 2004/0204354 A1 | 10/2004 | Nelson et al. |
| 2004/0259142 A1 | 12/2004 | Chai et al. |
| 2005/0085413 A1 | 4/2005 | Jin et al. |
| 2005/0089473 A1 | 4/2005 | Black et al. |
| 2005/0106108 A1 | 5/2005 | Hansen et al. |
| 2005/0123546 A1 | 6/2005 | Umana et al. |
| 2005/0124533 A1 | 6/2005 | Schatzberg et al. |
| 2005/0221337 A1 | 10/2005 | Seeberger et al. |
| 2005/0221397 A1 | 10/2005 | Saito |
| 2005/0255491 A1 | 11/2005 | Lee |
| 2006/0019256 A1 | 1/2006 | Clarke et al. |
| 2006/0073122 A1 | 4/2006 | Koezuka et al. |
| 2006/0073161 A1 | 4/2006 | Breton |
| 2006/0211856 A1 | 9/2006 | Tsuji et al. |
| 2006/0216316 A1 | 9/2006 | Dhodapkar et al. |
| 2006/0286140 A1 | 12/2006 | Wickstrom et al. |
| 2006/0286637 A1 | 12/2006 | Hamilton |
| 2007/0059769 A1 | 3/2007 | Blixt et al. |
| 2007/0065949 A1 | 3/2007 | Hutchens |
| 2007/0207090 A1 | 9/2007 | Giudice |
| 2007/0213278 A1 | 9/2007 | Wong et al. |
| 2007/0213297 A1 | 9/2007 | Wong et al. |
| 2007/0219351 A1 | 9/2007 | Fiume et al. |
| 2007/0224189 A1 | 9/2007 | Lazar et al. |
| 2007/0238871 A1 | 10/2007 | Tsuji et al. |
| 2008/0070324 A1 | 3/2008 | Floyd |
| 2008/0145838 A1 | 6/2008 | Suda et al. |
| 2008/0175870 A1 | 7/2008 | Mather et al. |
| 2008/0220988 A1 | 9/2008 | Zhou |
| 2008/0260774 A1 | 10/2008 | Wong et al. |
| 2009/0035179 A1 | 2/2009 | Rakow et al. |
| 2009/0060921 A1 | 3/2009 | Dickey et al. |
| 2009/0081255 A1 | 3/2009 | Bublot et al. |
| 2009/0123439 A1 | 5/2009 | Yun et al. |
| 2009/0285837 A1 | 11/2009 | Kao et al. |
| 2009/0298797 A1 | 12/2009 | Zheng et al. |
| 2009/0317837 A1 | 12/2009 | Wong et al. |
| 2010/0003674 A1 | 1/2010 | Cope et al. |
| 2010/0009339 A1 | 1/2010 | Bovin et al. |
| 2010/0022026 A1 | 1/2010 | Rump et al. |
| 2010/0047827 A1 | 2/2010 | Laine et al. |
| 2010/0047828 A1 | 2/2010 | Sorenson et al. |
| 2010/0068806 A1 | 3/2010 | Laine et al. |
| 2010/0081150 A1 | 4/2010 | Liu et al. |
| 2010/0112195 A1 | 5/2010 | Kodas et al. |
| 2010/0113397 A1 | 5/2010 | Wong et al. |
| 2010/0136009 A1 | 6/2010 | Papkoff et al. |
| 2010/0136042 A1 | 6/2010 | Wong et al. |
| 2010/0173323 A1 | 7/2010 | Strome |
| 2010/0275280 A1 | 10/2010 | Clevers et al. |
| 2011/0086408 A1 | 4/2011 | Power |
| 2011/0104188 A1 | 5/2011 | Tashiro et al. |
| 2011/0124116 A1 | 5/2011 | Wohlstadter et al. |
| 2011/0137570 A1 | 6/2011 | Lapadula et al. |
| 2011/0237459 A1 | 9/2011 | Nova et al. |
| 2011/0262358 A1 | 10/2011 | Torigoe et al. |
| 2011/0263828 A1 | 10/2011 | Wong et al. |
| 2012/0046346 A1 | 2/2012 | Rossi et al. |
| 2012/0171201 A1 | 7/2012 | Sapra |
| 2012/0178705 A1 | 7/2012 | Liang et al. |
| 2012/0178802 A1 | 7/2012 | Withers et al. |
| 2012/0226024 A1 | 9/2012 | Wang et al. |
| 2012/0270826 A1 | 10/2012 | Cope et al. |
| 2012/0294859 A1 | 11/2012 | Goletz et al. |
| 2012/0322864 A1 | 12/2012 | Rossi et al. |
| 2012/0322865 A1 | 12/2012 | Rossi et al. |
| 2012/0328646 A1 | 12/2012 | Wong et al. |
| 2013/0065887 A1 | 3/2013 | Bhatia et al. |
| 2013/0071390 A1 | 3/2013 | Stadheim et al. |
| 2013/0189258 A1 | 7/2013 | Rother |
| 2013/0196356 A1 | 8/2013 | Jackson et al. |
| 2013/0230886 A1 | 9/2013 | Votsmeier et al. |
| 2013/0295104 A1 | 11/2013 | Deckert et al. |
| 2013/0331381 A1 | 12/2013 | Bhatia et al. |
| 2013/0337018 A1 | 12/2013 | Fox |
| 2013/0345289 A1 | 12/2013 | Cope et al. |
| 2014/0051127 A1 | 2/2014 | Wong et al. |
| 2014/0086916 A1 | 3/2014 | Zha |
| 2014/0127241 A1 | 5/2014 | Leuschner et al. |
| 2014/0178365 A1 | 6/2014 | Ghaderi et al. |
| 2014/0227290 A1 | 8/2014 | Sethuraman |
| 2014/0302028 A1 | 10/2014 | Zha |
| 2014/0308746 A1 | 10/2014 | Rossi et al. |
| 2015/0087814 A1 | 3/2015 | Wang |
| 2015/0094237 A1 | 4/2015 | Liang et al. |
| 2015/0160217 A1 | 6/2015 | Wong et al. |
| 2015/0225766 A1 | 8/2015 | Wong et al. |
| 2015/0309041 A1 | 10/2015 | Wong et al. |
| 2015/0344544 A1 | 12/2015 | Wong et al. |
| 2015/0344551 A1 | 12/2015 | Wong et al. |
| 2015/0344559 A1 * | 12/2015 | Wong ............. C12Y 302/01051 424/133.1 |
| 2015/0344585 A1 * | 12/2015 | Wong ................... A61P 35/02 424/133.1 |
| 2015/0344587 A1 * | 12/2015 | Wong ................... A61P 43/00 424/133.1 |
| 2016/0009803 A1 | 1/2016 | Rother et al. |
| 2016/0017390 A1 | 1/2016 | Wong et al. |
| 2016/0058886 A1 | 3/2016 | Fonseca et al. |
| 2016/0102151 A1 | 4/2016 | Wong et al. |
| 2016/0213763 A1 | 7/2016 | Wong et al. |
| 2016/0215061 A1 | 7/2016 | Shaeen |
| 2016/0274121 A1 | 9/2016 | Wong et al. |
| 2016/0280794 A1 | 9/2016 | Wong et al. |
| 2016/0289340 A1 | 10/2016 | Wong et al. |
| 2017/0038378 A1 | 2/2017 | Wong et al. |
| 2017/0275389 A1 | 9/2017 | Wong et al. |

(56) References Cited

U.S. PATENT DOCUMENTS

| | | |
|---|---|---|
| 2017/0283488 A1 | 10/2017 | Yu et al. |
| 2017/0283878 A1 | 10/2017 | Wong et al. |
| 2017/0362265 A1 | 12/2017 | Wong et al. |
| 2017/0362330 A1 | 12/2017 | Liu |
| 2018/0106780 A1 | 4/2018 | Wong et al. |
| 2018/0155761 A1 | 6/2018 | Wong et al. |
| 2018/0193481 A1 | 7/2018 | Chang et al. |
| 2018/0265590 A1* | 9/2018 | Wong ............... A61K 45/06 |
| 2018/0291109 A1 | 10/2018 | Lin et al. |
| 2018/0362662 A1 | 12/2018 | Wong et al. |
| 2019/0085062 A1 | 3/2019 | Wong et al. |
| 2019/0177435 A1 | 6/2019 | Wong et al. |
| 2019/0194303 A1 | 6/2019 | Wong et al. |
| 2019/0277843 A1 | 9/2019 | Wong et al. |
| 2019/0391149 A1 | 12/2019 | Wong et al. |
| 2020/0165649 A1* | 5/2020 | Wong ............... C07K 16/241 |

FOREIGN PATENT DOCUMENTS

| | | | |
|---|---|---|---|
| CN | 101868534 A | 10/2010 | |
| CN | 102203290 A | 9/2011 | |
| CN | 103436627 A | 12/2013 | |
| CN | 104225616 A | 12/2014 | |
| EP | 0404097 A2 | 12/1990 | |
| EP | 0341735 B1 | 9/1992 | |
| EP | 0425235 B1 | 9/1996 | |
| EP | 1208909 A2 | 5/2002 | |
| EP | 1391213 A1 | 2/2004 | |
| EP | 2123271 A1 | 11/2009 | |
| EP | 2187217 A1 | 5/2010 | |
| JP | H05-222085 A | 8/1993 | |
| JP | H05-507068 A | 10/1993 | |
| JP | H05-339283 A | 12/1993 | |
| JP | H06-217769 A | 8/1994 | |
| JP | H11-343295 A | 12/1999 | |
| JP | 2000-506008 A | 5/2000 | |
| JP | 2002-371087 A | 12/2002 | |
| JP | 2008-025989 A | 2/2008 | |
| JP | 2008-526812 A | 7/2008 | |
| JP | 2009-515979 A | 4/2009 | |
| JP | 2010-532995 A | 10/2010 | |
| JP | 2012-503656 A | 2/2012 | |
| WO | WO 87/00195 A1 | 1/1987 | |
| WO | WO 90/03430 A1 | 4/1990 | |
| WO | WO 91/00360 A1 | 1/1991 | |
| WO | WO 91/10741 A1 | 7/1991 | |
| WO | WO 92/00373 A1 | 1/1992 | |
| WO | WO 92/006691 A1 | 4/1992 | |
| WO | WO 92/09690 A2 | 6/1992 | |
| WO | WO 93/01161 A1 | 1/1993 | |
| WO | WO 93/06213 | 4/1993 | |
| WO | WO 93/07861 A1 | 4/1993 | |
| WO | WO 93/08829 A1 | 5/1993 | |
| WO | WO 93/09764 A1 | 5/1993 | |
| WO | WO 93/16185 A2 | 8/1993 | |
| WO | WO 93/021232 A1 | 10/1993 | |
| WO | WO 94/04690 A1 | 3/1994 | |
| WO | WO 94/11026 A2 | 5/1994 | |
| WO | WO 94/29351 A2 | 12/1994 | |
| WO | WO 95/11010 A1 | 4/1995 | |
| WO | WO 96/07754 A1 | 3/1996 | |
| WO | WO 96/16673 A1 | 6/1996 | |
| WO | WO 96/33735 A1 | 10/1996 | |
| WO | WO 96/34096 A1 | 10/1996 | |
| WO | WO 97/05267 A2 | 2/1997 | |
| WO | WO 97/013537 A1 | 4/1997 | |
| WO | WO 97/17852 A1 | 5/1997 | |
| WO | WO 97/037705 A1 | 10/1997 | |
| WO | WO 98/00558 A1 | 1/1998 | |
| WO | WO 98/02463 A1 | 1/1998 | |
| WO | WO 98/24893 A2 | 6/1998 | |
| WO | WO 99/034850 A1 | 7/1999 | |
| WO | WO 99/49019 A2 | 9/1999 | |
| WO | WO 99/051642 A1 | 10/1999 | |
| WO | WO 99/057134 A1 | 11/1999 | |
| WO | WO 01/42505 A2 | 6/2001 | |
| WO | WO 01/86001 A1 | 11/2001 | |
| WO | WO 02/088172 A2 | 11/2002 | |
| WO | WO 03/040104 A1 | 5/2003 | |
| WO | WO 03/68821 A2 | 8/2003 | |
| WO | WO 03/077945 A1 | 9/2003 | |
| WO | WO 2004/035607 A2 | 4/2004 | |
| WO | WO 2004/056312 A2 | 7/2004 | |
| WO | WO 2004/063351 A2 | 7/2004 | |
| WO | WO 2004/103404 A1 | 12/2004 | |
| WO | WO 2005/030258 A2 | 4/2005 | |
| WO | WO 2005/044859 A2 | 5/2005 | |
| WO | WO 2005/088310 A2 | 9/2005 | |
| WO | WO 2005/103081 A2 | 11/2005 | |
| WO | WO 2006/055925 A2 | 5/2006 | |
| WO | WO 2006/064983 A1 | 6/2006 | |
| WO | WO 2006/072624 A2 | 7/2006 | |
| WO | WO 2006/106959 A1 | 10/2006 | |
| WO | WO 2006/126069 A2 | 11/2006 | |
| WO | WO 2006/130458 A2 | 12/2006 | |
| WO | WO 2007/053648 A2 | 5/2007 | |
| WO | WO 2007/059188 A1 | 5/2007 | |
| WO | WO 2007/078873 A1 | 7/2007 | |
| WO | WO 2007/133855 A2 | 11/2007 | |
| WO | WO 2007/146847 A2 | 12/2007 | |
| WO | WO 2008/020596 A2 | 2/2008 | |
| WO | WO 2008/087260 A1 | 7/2008 | |
| WO | WO 2008/118013 A2 | 10/2008 | |
| WO | WO 2008/133801 A1 | 11/2008 | |
| WO | WO 2008/0133857 A1 | 11/2008 | |
| WO | WO 2009/009086 A2 | 1/2009 | |
| WO | WO 2009/029888 A3 | 3/2009 | |
| WO | WO 2009/126735 A1 | 10/2009 | |
| WO | WO 2010/006315 A2 | 1/2010 | |
| WO | WO 2010/009271 A1 | 1/2010 | |
| WO | WO 2010/011703 A1 | 1/2010 | |
| WO | WO2010/029302 A2 | 3/2010 | |
| WO | WO 2011/005756 A1 | 1/2011 | |
| WO | WO 2011/006237 A1 | 1/2011 | |
| WO | WO 2011/031236 A1 | 3/2011 | |
| WO | WO 2011/074621 A1 | 6/2011 | |
| WO | WO 2011/089004 A1 | 7/2011 | |
| WO | WO 2011/130332 A1 | 10/2011 | |
| WO | WO 2011/143262 A2 | 11/2011 | |
| WO | WO 2011/145957 A1 | 11/2011 | |
| WO | WO 2012/082635 A1 | 6/2012 | |
| WO | WO 2012/094540 A2 | 7/2012 | |
| WO | WO 2012/162277 A1 | 11/2012 | |
| WO | WO 2013/011347 A1 | 1/2013 | |
| WO | WO 2013/012066 A1 | 1/2013 | |
| WO | WO 2013/024895 A1 | 2/2013 | |
| WO | WO 2013/066761 A1 | 5/2013 | |
| WO | WO 2013/088395 A1 | 6/2013 | |
| WO | WO 2013/106937 A1 | 7/2013 | |
| WO | 2013120066 | 8/2013 | |
| WO | WO 2013/110946 A1 | 8/2013 | |
| WO | WO 2013/120066 A1 | 8/2013 | |
| WO | WO2013/126993 A1 | 9/2013 | |
| WO | WO 2013/130603 A1 | 9/2013 | |
| WO | WO 2013/152034 A1 | 10/2013 | |
| WO | WO 2013/155375 A1 | 10/2013 | |
| WO | WO 2013/181585 A2 | 12/2013 | |
| WO | WO 2014/031498 A1 | 2/2014 | |
| WO | WO 2014/078373 A1 | 5/2014 | |
| WO | 2014161960 A1 | 10/2014 | |
| WO | WO 2014/161960 A1 | 10/2014 | |
| WO | WO 2014/210397 A1 | 12/2014 | |
| WO | WO 2014/210564 A1 | 12/2014 | |
| WO | WO 2015/026484 A1 | 2/2015 | |
| WO | WO 2015/035337 A1 | 3/2015 | |
| WO | WO 2015/038963 A1 | 3/2015 | |
| WO | WO 2015/184008 A1 | 12/2015 | |
| WO | WO 2016/040369 A2 | 3/2016 | |

(56) References Cited

FOREIGN PATENT DOCUMENTS

| WO | WO 2016/118090 A1 | 7/2016 |
|---|---|---|
| WO | WO 2014/031762 A1 | 2/2017 |

OTHER PUBLICATIONS

Mouquet et al. Complex-type N-glycan recognition by potent broadly neutralizing HIV antibodies, Proc. Natl. Acad. Sci. published online Oct. 30, 2012; Nov. 2012, 109(47), E3268-E3277, 10 pages.

Mouquet et al. "Complex-type N-glycan recognition by potent broadly neutralizing HIV antibodies." Proceedings of the National Academy of Sciences 109.47 (2012): E3268-E327; Supplementary Information, 54 pages.

Nordstrom, Jeffrey L., et al. "Anti-tumor activity and toxicokinetics analysis of MGAH22, an anti-HER2 monoclonal antibody with enhanced Feγ receptor binding properties." Breast Cancer Research 13.6 (2011): R123, 14 pages.

Posey, Avery D., et al. "Precise Glycoediting by CRISPR/Cas9 Mediated Gene Disruption Elucidates the Specificity of a Chimeric Antigen Receptor for the Globoside SSEA-4." Molecular Therapy. vol. 25. No. 5. Supplement 1, Abstract 586, pp. 271; 50 Hampshire St, Floor 5, Cambridge, MA 02139 USA: Cell Press, 2017; Annual Meeting of the American Society of Gene and Cell Therapy, ASGCT 2017, Washington D.C., May 10-May 13, 2017.

Shivatare, Sachin S., et al. "Chemo-enzymatic Synthesis of N-glycans for Array Development and HIV Antibody Profiling." Journal of Visualized Experiments 132 (2018): e55855, 9 pages.

Shivatare, Vidya S., et al. "Unprecedented role of hybrid N-glycans as ligands for HIV-1 broadly neutralizing antibodies." Journal of the American Chemical Society 140.15 (2018): 5202-5210.

Shivatare, Vidya S., et al. "Unprecedented role of hybrid N-glycans as ligands for HIV-1 broadly neutralizing antibodies." Journal of the American Chemical Society 140.15 (2018): 5202-5210, Supporting Information, 68 pages.

Sun, Yi, et al. "Isolation of stem-like cancer cells in primary endometrial cancer using cell surface markers CD133 and CXCR4." Translational Oncology 10.6 (2017): 976-987.

Ward, Elizabeth, et al. "A glycoengineered anti-CD19 antibody with potent antibody-dependent cellular cytotoxicity activity in vitro and lymphoma growth inhibition in vivo." British Journal of Haematology 155.4 (2011): 426-437.

Al-Hajj, Muhammad, et al. "Prospective identification of tumorigenic/ breast cancer cells." Proceedings of the National Academy of Sciences 100.7 (2003): 3983-3988.

Almagro, Juan C., and Johan Fransson. "Humanization of antibodies." Front Biosci 13.1 (2008): 1619-1633.

Beck, Benjamin, and Cédric Blanpain. "Unravelling cancer stem cell potential." Nature Reviews Cancer 13.10 (2013): 727.

Bomken, S., et al. "Understanding the cancer stem cell." British journal of cancer 103.4 (2010): 439-445.

Casset, Florence, et al. "A peptide mimetic of an anti-CD4 monoclonal antibody by rational design." Biochemical and biophysical research communications 307.1 (2003): 198-205.

Clarke, Michael F., and Andrew T. Hass. "Cancer stem cells." Reviews in Cancer Res. (2006) 66(19):9339-9344.

De Genst, Erwin, et al. "Antibody repertoire development in camelids." Developmental & Comparative Immunology 30.1-2 (2006): 187-198.

De Leoz, Maria Lorna A., et al. "High-mannose glycans are elevated during breast cancer progression." Molecular & Cellular Proteomics 10.1 (2011): M110-002717, 9 pages; https://doi.org/10.1074/mcp.M110.002717.

Danishefsky, Samuel J., et al. "Development of Globo-H cancer vaccine." Accounts of Chemical Research 48.3 (2015): 643-652.

De Pascalis, Roberto, et al. "Grafting of "abbreviated" complementarity-determining regions containing specificity-determining residues essential for ligand contact to engineer a less immunogenic humanized monoclonal antibody." The Journal of Immunology 169.6 (2002): 3076-3084.

Dorner, Brigitte G., et al. "MIP-1a, MIP-1β, Rantes, and ATAC/ lymphotactin function together with IFN-? as type 1 cytokines." Proceedings of the National Academy of Sciences 99.9 (2002): 6181-6186.

Fuster, Mark M., and Jeffrey D. Esko. "The sweet and sour of cancer: glycans as novel therapeutic targets." Nature Reviews Cancer 5.7 (2005): 526-542.

Gao, Jingqing, Dianjun Liu, and Zhenxin Wang. "Microarray-based study of carbohydrate-protein binding by gold nanoparticle probes." Analytical chemistry 80.22 (2008): 8822-8827.

Ghaderi, Darius, et al. "Production platforms for biotherapeutic glycoproteins. Occurrence, impact, and challenges of non-human sialylation." Biotechnology and Genetic Engineering Reviews 28.1 (2012): 147-176.

Ginestier, Christophe, et al. "ALDH1 is a marker of normal and malignant human mammary stem cells and a predictor of poor clinical outcome." Cell stem cell 1.5 (2007): 555-567.

Hakomori, S., and W. W. Young Jr. "Tumor-associated glycolipid antigens and modified blood group antigens." Scandinavian Journal of Immunology 7 (1978): 97-117.

Hakomori, Sen-itiroh. "Aberrant glycosylation in cancer cell membranes as focused on glycolipids: overview and perspectives." Cancer research 45.6 (1985): 2405-2414.

Harvey, David J. "Matrix-assisted laser desorption/ionization mass spectrometry of sphingo- and glycosphingo-Lipids." Journal of Mass Spectrometry 30.9 (1995): 1311-1324.

Hwang-Verslues, Wendy W., et al. "Multiple lineages of human breast cancer stem/progenitor cells identified by profiling with stem cell markers." PloS one 4.12 (2009): e8377.

Intra, Jari, et al. "Comparative and phylogenetic analysis of α-l- fucosidase genes." Gene 392.1-2 (2007): 34-46.

Jordan, et al. "Cancer stem cells." N Engl J Med 355.12 (2006): 1253-1261.

Lamminmäki, Urpo, and Jussi A. Kankare. "Crystal structure of a recombinant anti-estradiol Fab fragment in complex with 17β-estradiol." Journal of Biological Chemistry 276.39 (2001): 36687-36694.

Liang, Chi-Hui, et al. "Effects of neighboring glycans on antibody-carbohydrate interaction." Angewandte Chemie International Edition 50.7 (2011): 1608-1612.

Lingwood, Daniel, et al. "Cholesterol modulates glycolipid conformation and receptor activity." Nature chemical biology 7.5 (2011): 260-262.

Listinsky, Jay J., et al. "Glycoengineering in cancer therapeutics: a review with fucose-depleted trastuzumab as the model." Anti-cancer drugs 24.3 (2013): 219-227.

Lloyd et al. "Modelling the human immune response: performance of a 1011 human antibody repertoire against a broad panel of therapeutically relevant antigens" Protein Eng Des Sel. Mar. 2009;22(3):159-68. doi: 10.1093/protein/gzn058. Epub Oct. 29, 2008.

MacCallum, Robert M., et al. "Antibody-antigen interactions: contact analysis and binding site topography." Journal of molecular biology 262.5 (1996): 732-745.

Novak, Anton, et al. "Cholesterol masks membrane glycosphingolipid tumor-associated antigens to reduce their immunodetection in human cancer biopsies." Glycobiology 23.11 (2013): 1230-1239.

Office Action dated Oct. 26, 2018, from corresponding Chinese Patent Application No. 201680006858.6, 13 total pages.

Package insert for human-type human TNF-alpha monoclonal antibody preparation, HUMIRA, subcutaneous injection 40 mg, 2009, p. 1-7; ; Machine translation provided.

Padlan, Eduardo A., et al. "Structure of an antibody-antigen complex: crystal structure of the HyHEL-10 Fab-lysozyme complex." Proceedings of the National Academy of Sciences 86.15 (1989): 5938-5942.

Partial European Search Report dated Jun. 13, 2018 in EP application 16740906.9, 14 pages.

Pece, Salvatore, et al. "Biological and molecular heterogeneity of breast cancers correlates with their cancer stem cell content." Cell 140.1 (2010): 62-73.

(56) References Cited

OTHER PUBLICATIONS

Q5LAD6 ver 52, Definition: Bacteroides fragilis (strain ATCC 25285/NCTN 9343), UniProtKB/TrEMBL [online], May 14, 2014, URL at http://www.uniprot.org/uniprot/Q5LAD6.txt?version=52; downloaded Feb. 8, 2019, 19 pages.

Rajan, Valanila P., et al. "A cloned human DNA restriction fragment determines expression of a GDP-L-fucose: beta-D-galactoside 2-alpha-L-fucosyltransferase in transfected cells. Evidence for isolation and transfer of the human H blood group locus." Journal of Biological Chemistry 264.19 (1989): 11158-11167.

Rouquier, Sylvie, et al. "Molecular cloning of a human genomic region containing the H blood group a (1, 2) fucosyltransferase gene and two H locus-related DNA restriction fragments isolation of a candidate for the human secretor blood group locus." Journal of Biological Chemistry 270.9 (1995): 4632-4639.

Rudikoff, Stuart, et al. "Single amino acid substitution altering antigen-binding specificity." Proceedings of the National Academy of Sciences 79.6 (1982): 1979-1983.

Shaw, Frances L., et al. "A detailed mammosphere assay protocol for the quantification of breast stem cell activity." Journal of mammary gland biology and neoplasia 17.2 (2012): 111-117.

Stanley, Pamela, and Richard D. Cummings. "Chapter 13. Structures common to different glycans." Essentials of Glycobiology [Internet]. 2nd edition. Cold Spring Harbor Laboratory Press (NY), 2009; NCBI Bookshelf, retrieved from the internet on Aug. 17, 2017, 40, pages.

Tripp, Ralph A., et al. "Bioconjugated nanoparticle detection of respiratory syncytial virus infection." International Journal of Nanomedicine 2(1) (2007): 117-124.

Tsai, H. H., C. A. Hart, and J. M. Rhodes. "Production of mucin degrading sulphatase and glycosidases by Bacteroides thetaiotaomicron." Letters in Applied Microbiology 13.2 (1991): 97-101.

Vajdos, Felix F., et al. "Comprehensive functional maps of the antigen-binding site of an anti-ErbB2 antibody obtained with shotgun scanning mutagenesis." Journal of molecular biology 320.2 (2002): 415-428.

Wright, Mollie H., et al. "Brca1 breast tumors contain distinct CD44+/CD24-and CD133+ cells with cancer stem cell characteristics." Breast Cancer Research 10.1 (2008): R10.

Wu, Herren, et al. "Humanization of a murine monoclonal antibody by simultaneous optimization of framework and CDR residues." Journal of Molecular Biology 294.1 (1999): 151-162.

Zhou, Dapeng, et al. "The β1, 3-galactosyltransferase β3GalT-V is a stage-specific embryonic antigen-3 (SSEA-3) synthase." Journal of Biological Chemistry 275.30 (2000): 22631-22634.

U.S. Appl. No. 15/173,496, filed Jun. 3, 2016, Wong et al.

Abbas et al., "Functional diversity of helper T lymphocytes," Nature, Oct. 31, 1996, 383(6603):787-793.

Abrahmsén et al., "Analysis of signals for secretion in the staphylococcal protein A gene," EMBO J., Dec. 30, 1985, 4(13B):3901-3906.

Achtman, M., Epidemic Spread and Antigenic Variability of Neisseria Meningitidis, Trends Microbial 1995, 3, 186-192.

Adam et al., "Proteomic profiling of mechanistically distinct enzyme classes using a common chemotype", Nat. Biotechnol., Aug. 2002, 20(8):805-809.

Agard, N. et al., A Strain-Promoted [3+2]Azide-Alkyne Cycloaddition for Covalent Modification of Biomolecules in Living Systems, J. Am. Chem. Soc. 2004, 126, 15046-15047.

Ahmadi, T. S. et al., Shape-Controlled Synthesis of Colloidal Platinum Nanoparticles, Science, 272, 1924 (1996).

Ahmed et al.,Structural Characterization of Anti-Inflammatory Immunoglobulin G Fc Proteins, K Mol Biol (2014) 426, 3166-3179.

Altevogt, Peter et al., Different Patterns of Lectin Binding and Cell Surface Sialylation Detected on Related High- and Low-Metastatic Tumor Lines, Cancer Res. 43, 5138-5144, 1983.

Altschul SF et al., "Basic local alignment search tool", J Mol Biol. Oct. 5, 1990;215(3):403-10.

Altschul SF, et al., "Gapped BLAST and PSI-BLAST: a new generation of protein database search programs", Nucleic Acids Res. Sep. 1, 1997;25(17):3389-402.

Amin, M. N. et al. Synthetic glycopeptides reveal the glycan specificity of HIV-neutralizing antibodies. Nat. Chem. Biol. 9, 521-526, (2013.

Anderson et al., "Stimulation of Natural Killer T Cells by Glycolipids", Molecules, May 2013, 18(12), 15662-15688.

Andrews et al., Synthesis and influenza virus sialidase inhibitory activity of analogues of 4-Guanidino-Neu5Ac2en (Zanamivir modified in the glycerol side-chain. Eur J Med Chern Jul.-Aug. 1999;34(7-8):563-74.

Angata et al., "Chemical diversity in the sialic acids and related α-keto acids: an evolutionary perspective," Chem. Rev., Feb. 2002, 102(2):439-469.

Anthony, Robert et al., Recapitulation of IVIG Anti-Inflammatory Activity with a Recombinant IgG Fc, Science Apr. 18, 2008. 320:373-376.

Arase et al., "NK1.1$^+$ CD4$^+$ CD8$^-$ thymocytes with specific lymphokine secretion," Eur. J. Immunol., Jan. 1993, 23(1):307-310.

Arié et al., "Chaperone function of FkpA, a heat shock prolyl isomerase, in the periplasm of Escherichia coli," Mol. Microbiol., Jan. 2001, 39(1):199-210.

Aspeslagh et al., "Galactose-modified iNKT cell agonists stabilized by an induced fit of CD1d prevent tumour metastasis," EMBO J., Jun. 1, 2011, 30(11):2294-2305.

Astronomo, R. D. & Burton, D.R. Carbohydrate vaccines: developing sweet solutions to sticky situations? Nat. Rev. Drug. Discov. 9, 308-324, (2010.

Bachmann, Cellular and Molecular Biology, vol. 2, Chapter 72: Derivations and Genotypes of Some Mutant Derivatives of Escherichia coli K-12, Neidhardt et al., eds.,. 1987, pp. 1190-1219, American Society for Microbiology, Washington, D.C.

Bacilieri, Magdalena et al., Ligand-Based Drug Design Methodologies in Drug Discovery Process: An Overview, Current Drug Discovery Technologies, vol. 3 (3), Sep. 2006, p. 155-165.

Database ENA [Online] "Bacteroides Fragilis NCTC 9343, Complete Genome," Mar. 3, 2005, XP002775523, retrieved from EBI Database Accession No. CR626927, DOI: 10.1126/science. 1107008, sequence, 2 Pages.

Database ENA [Online] "Bacteroides Thetaiotaomicron VPI-5482, Section 8 of 21 of the Complete Genome," XP002775522, Mar. 29, 2003, retrieved from EBI Database Accession No. AE016933, DOI: 10.1126/science.1080029, sequence, 2 Pages.

Bai, Dan et al., Exploring Forster Electronic Energy Transfer in a Decoupled/Anthracenyl-based Borondipyrromethene (Bodipy) Dyad, Physical Chemistry Chemical Physics (2012), 14(13), 4447-4456.

Bailey, Ryan et al., Real-Time Multicolor DNA Detection with Chemoresponsive Diffraction Gratings and Nanoparticle Probes, J. Am Chem. Soc., 2003, 125, 13541-13547.

Baldwin et al., "Monoclonal antibodies in cancer treatment," Lancet, Mar. 15, 1986, 327(8481):603-605.

Banchereau et al., "Dendritic cells and the control of immunity," Nature, Mar. 19, 1998, 392(6673):245-252.

Barbas et al., "Assembly of combinatorial antibody libraries on phage surfaces: the gene III site," Proc. Natl. Acad. Sci. U.S.A., Sep. 15, 1991, 88(18):7978-7982.

Barbas et al., "In vitro evolution of a neutralizing human antibody to human immunodeficiency virus type 1 to enhance affinity and broaden strain cross-reactivity," Proc. Nat. Acad. Sci. U.S.A., Apr. 26, 1994, 91(9):3809-3813.

Barbas et al., "Semisynthetic combinatorial antibody libraries: a chemical solution to the diversity problem," Proc. Natl. Acad. Sci. U.S.A., May 15, 1992, 89(10):4457-4461.

Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.

Barnes et al., "Methods for growth of cultured cells in serum-free medium," Anal. Biochem., Mar. 1, 1980, 102(2):255-270.

Barouch, D. H. Challenges in the development of an HIV-I vaccine. Nature 455, 613-619, (2008).

(56) References Cited

OTHER PUBLICATIONS

Barry, C.S et al., 'Naked' and Hydrated Confirmers of the Conserved Core Pentasaccharide of N-Linked Glycoproteins and Its Building Blocks, Journal of the American Chemical Society, 2013, vol. 135(45), p. 16895-16903.
Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.
Baselga J, et al., "Phase II study of weekly intravenous recombinant humanized anti-p185HER2 monoclonal antibody in patients with HER2/neu-overexpressing metastatic breast cancer", *J Clin Oncol.* Mar. 1996;14(3):737-44.
Baskin, J.M.; Amacher, S. L.; Bertozzi, C.R."In vivo imaging of membraneassociated glycans in developing zebrafish." Science 2008, 320, 664-667.
Bass et al., "Hormone phage: an enrichment method for variant proteins with altered binding properties," *Proteins*, 1990, 8(4):309-314.
Bassell, G.J. et al., Single mRNAs Visualized By Ultrastructural in Situ Hybridization are Principally Localized at Actin Filament Intersections in Fibroblasts, J. Cell Biol., 126, 863-876 (1994.
Baz et al., Emergence of oseltamivir-resistant pandemic H1N1 virus during prophylaxis. N Engl J Med. Dec. 3, 2009;361(23):2296-7. doi: 10.1056/NEJMc0910060. Epub Nov. 11, 2009.
Beck A., "Biosimilar, biobetter and next generation therapeutic antibodies" *MAbs*. Mar.-Apr. 2011;3(2): 107-10. Epub Mar. 1, 2011.
Beckman et al., Antibody constructs in cancer therapy: protein engineering strategies to improve exposure in solid tumors, cancer, 109(2): 170-179 (2007).
Bendayan, Moise, Possibilities of False Immunocytochemical Results Generated By The Use of Momoclonal Antibodies: The Example of the Anti-Proinsulin Antibody, J. Histochem. Cytochem, 43: 881-886, (1995).
Bennett, Clay et al., Chemoenzymatic Approaches to Glycoprotein Synthesis, Chem. Soc. Rev. 2007, 36:1227-1238.
Berg, Jan-Olof et al., Purification of Glycoside Hydrolases From Bacteroides Fragilis, Applied and Environmental Microbiology, vol. 40, No. 1, Jul. 1980, p. 40-47.
Berge, Steven et al. "Pharmaceutical Salts," J. Pharmaceutical Sciences (1977) 66: 1-19.
Berra et al., "Correlation between ganglioside distribution and histological grading of human astrocytomas," *Int. J. Cancer*, Sep. 15, 1985, 36(3):363-366.
Best, M. D. "Click chemistry and bioorthogonal reactions: unprecedented selectivity in the labeling of biological molecules." Biochemistry 2009, 48, 6571-6584.
Bertozzi, CR et al., Glycans in Cancer and Inflammation—Potential for Therapeutics and Diagnostics, Nat Rev Drug Discovery, 2005, 4, 477-488.
Bigi et al., "Human sialidase NEU4 long and short are extrinsic proteins bound to outer mitochondrial membrane and the endoplasmic reticulum, respectively," *Glycobiology*, Feb. 2010, 20(2):148-157.
Birklé et al., "Role of tumor-associated gangliosides in cancer progression," *Biochimie*, Mar.-Apr. 2003, 85(3-4):455-463.
Blixt, O. et al. Printed covalent glycan array for ligand profiling of diverse glycan binding proteins. Proc. Natl. Acad. Sci. U. S. A. 101, 17033-17038, (2004.
Bobo et al., "Convection-enhanced delivery of macromolecules in the brain," *Proc. Natl. Acad. Sci. U.S.A.*, Mar. 15, 1994, 91(6) 2076-2080.
Boens, N. et al., "Fluorescent indicators based on BODIPY." Chem. Soc. Rev. 2012, 41, 1130-1172.
Boerner et al., "Production of antigen-specific human monoclonal antibodies from in vitro-primed human splenocytes," *J. Immunol.*, Jul. 1, 1991, 147(1):86-95.
Borg et al., "CD1d-lipid-antigen recognition by the semi-invariant NKT T-cell receptor," *Nature*, Jul. 5, 2007, 448(7149):44-49.

Bosmann et al., "Enzyme activity in invasive tumors of human breast and colon," *Proc. Natl. Acad. Sci. USA*, May 1974, 71(5):1833-1837.
Bost, Kenneth et al., Antibodies Against A Peptide Sequence Within The HIV Envelope Protein Crossreacts With Human Interleukin-2, Immunol. Invest., 17: 577-586 (1988).
Bothmann et al., "The periplasmic *Escherichia coli* peptidylprolyl cis, trans-isomerase FkpA. I. Increased functional expression of antibody fragments with and without cis-prolines," *J. Biol. Chem.*, Jun. 2, 2000, 275(22):17100-17105.
Boyer, David et al., Photothermal Imaging of Nanometer-Sized Metal Particles Among Scatterers, Science, 2002, 297, 1160-116 3.
Braun-Howland et al., Development of a Rapid Method for Detecting Bacterial Cell In Situ Using 16S rRNA-Targeted Probes, Biotechniques, 13, 928-931 (1992).
Brennan et al., "Preparation of bispecific antibodies by chemical recombination of monoclonal immunoglobulin $G_1$ fragments," *Science*, Jul. 5, 1985, 229(4708):81-83.
Bricard et al., "Enrichment of human $CD4^+$ $V\alpha24/V\beta11$ invariant NKT cells in intrahepatic malignant tumors," *J. Immunol.*, Apr. 15, 2009, 182(2):5140-5151.
Brimble et al., "The cell surface glycosphingolipids SSEA-3 and SSEA-4 are not essential for human ESC pluripotency," *Stem Cells*, Jan. 2007, 25(1):54-62.
Brodeur et al., *Monoclonal Antibody Production Techniques and Applications, Chapter 4: Mouse-Human Myeloma Partners for the Production of Heterohybridomas*, Schook, ed., 1987, pp. 51-63, Marcel Dekker, Inc., New York.
Bruchez, Marcel et al. Semiconductor Nanocrystals as Fluorescent Biological Labels, Science 281:2013-2016, 1998.
Brüuggemann et al., "Designer mice: the production of human antibody repertoires in transgenic animals," *Year in Immunol.*, 1993, 7:33-40.
Buchini et al., "Towards a new generation of specific *Trypanosoma cruzi* trans-sialidase inhibitors," *Angew. Chem. Int. Ed. Engl.*, 2008, 47(14):2700-2703.
Burton, D.R., Mascola, J. R. Antibody responses to envelope glycoproteins in HIV-I infection. Nature Immunol. 16, 571-6, (2015).
Calarese, D. A. et al. Antibody domain exchange is an immunological solution to carbohydrate cluster recognition. Science 300, 2065-2071, (2003).
Cao, Y. C. et al., Nanoparticles with Raman Spectroscopic Fingerprints for DNA and RNA Detection, Science, 2002, 289, 1757-60.
Capel PJ et al., "Heterogeneity of human IgG Fc receptors" *Immunomethods*. Feb. 1994;4(1):25-34.
Carlsson, Jan et al., Protein Thiolation and Reversible Protein-Protein Conjugation, Biochem J 173: 723-737 (1978).
Carter et al., "High level *Escherichia coli* expression and production of a bivalent humanized antibody fragment," *Nature Biotechnology*, Feb. 1992, 10(2): 163-167.
Carter et al., "Humanization of an anti-p185$^{HER2}$ antibody for human cancer therapy," *Proc. Natl. Acad. Sci. U.S.A.*, May 15, 1992, 89(10):4285-4289.
Carter PJ. "Potent antibody therapeutics by design" *Nat Rev Immunol.* May 2006;6(5):343-357.
Carter, A rationale for using steroids in the treatment of severe cases of H5N1 avian influenza. J Med Microbiol. Jul. 2007;56(Pt 7):875-83.
Centers for Disease Control and Prevention (CDC), "Influenza activity—United States and worldwide, Aug. 2007 season" *MMWR*, Jun. 27, 2008, 57(25):692-697.
Cespedes et al., Mouse models in oncogenesis and cancer therapy, Clin Transl Oncl., 8(5): 318-329 (2006).
Chan, Warren et al., Quantum Dot Bioconjugates for Ultrasensitive Nonisotopic Detection, Science 281:2016-2018 (1998).
Chandler et al., Synthesis of the potent influenza neuraminidase inhibitor 5-guanidino Neu5Ac2en. X-Ray molecular structure of 5-acetaminido-4amino-2,6-anahydro-3,4,5-tryoxy-D-erythoro-L-gluco-nononic acid. J Chem Soc Perkin Trans 1. 1995; 1173-1180.

(56) References Cited

OTHER PUBLICATIONS

Chang et al., "Expression of Globo H and SSEA3 in breast cancer stem cells and the involvement of fucosyl transferases 1 and 2 in Globo H synthesis," Proc. Natl. Acad. Sci. U.S.A., Aug. 19, 2008, 105(33):11667-11672.

Chang, S. H. et al. Glycan array on aluminum oxide-coated glass slides through phosphonate chemistry. J. Am. Chem. Soc. 132, 13371-13380, (2010).

Chang et al., "Potent immune-modulating and anticancer effects of NKT cell stimulatory glycolipids," Proc. Natl. Acad. Sci. USA, Jun. 19, 2007, 104(25):10299-10304.

Chari, Ravi et al., Immunoconjuates Containing Novel Maytansinoids: Promising. Anticancer Drugs Cancer Research 52: 127-131 (1992).

Chauhan, D. P.; Saha, T.; Lahiri, M.; Talukdar, P. "BODIPY based 'click on' fluorogenic dyes: application in live cell imaging." Tetrahedron Lett. 2014, 55, 244-247.

Chen et al., "Chaperone activity of DsbC," J. Bio. Chem., Jul. 9. 1999, 274(28):19601-19605.

Chen et al., "Selection and analysis of an optimized anti-VEGF antibody: crystal structure of an affinity-matured Fab in complex with antigen," J. Mol. Biol., Nov. 5, 1999, 293(4):865-881.

Chen et al., "Selective killing of transformed cells by cyclin/cyclin-dependent kinase 2 antagonists," Proc. Natl. Acad. Sci. U.S.A., Apr. 13, 1999, 96(8):4325-4329.

Cheng, Peter et al., Oseltamivir-and Amandtadine-resistant Influenza Viruses A (H1N1), Emerg. Infect. Dis., Jun. 2009, 15(6): 966-968.

Cheung et al., Stage-specific embryonic antigen-3 (SSEA-3) and beta3GalT5 are cancer specific and significant markers for breast cancer stem cells, PNAS, Jan. 26, 2016, vol. 113, No. 4, pp. 960-965.

Cheung et al., Glycoconjugate Journal, Jul. 2015, vol. 32, No. 5, pp. 323, Abstract No. 338; DOI: 10.1007 /s10719-015-9596-4; Meeting Info: 23rd International Symposium on Glycoconjugates, Glyco 23. Split, Croatia, Sep. 15, 2015-Sep. 20, 2015.

Chiang et al., Ethyl caffeate suppresses NF-kappaB activation and its downstream inflammatory mediators, iNOS, COX-2, and PGE2 in vitro or in mouse skin. Br J Pharmacol. Oct. 2005; 146(3):352-63.

Chiari, M. et al., Advanced Polymers for Molecular Recognition and Sensing at the Interface. J Chromatography B, Apr. 15, 2008, 866(1-2):89-103.

Childs et al., Receptor-Binding Specificity of Pandemic Influenza A (H1N1) 2009 Virus Determined by Carbohydrate Microarray. Nat. Biotechnol. 2009, 27(9): 797-799.

Cho, Se-Heon et al., Sialyl-Tn Antigen Expression Occurs Early During Human Mammary Carcinogenesis and is Associated with High Nuclear Grade and Aneuploidy, Cancer Res. 54, 6302-6305, 1994.

Chong et al., Influenza Virus Sialidase: Effect of Calcium on Steady-State Kinetic Parameters, Biochim. Biophys. Acta, Mar. 8, 1991, 1077(1): 65-71.

Chothia et al., "Canonical structures for the hypervariable regions of immunoglobulins," J. Mol. Biol., Aug. 20, 1987, 196(4):901-917.

Chothia et al., "Domain association in immunoglobulin molecules. The packing of variable domains," J. Mol. Biol., Dec. 5, 1985, 186(3):651-663.

Chu, Kuo-Chinget al., Efficient and Stereoselective Synthesis of [alpha](2->9) Oligosialic Acids: From Monomers to Dodecamers, Angewandte Chemie International Edition, vol. 50, No. 40, Sep. 2011, 9391-9395.

Clackson et al., "Making antibody fragments using phage display libraries," Nature, Aug. 15, 1991, 352(6336):624-628.

Clark EA et al., "Structure, function, and genetics of human B cell-associated surface molecules" Adv Cancer Res. 1989;52:81-149.

Clynes R, et al., "Fc receptors are required in passive and active immunity to melanoma" Proc Natl Acad Sci U S A. Jan. 20, 1998;95(2):652-6.

Codelli, J. A. et al., Second-Generation Difluorinated Cycloctynes for Copper-Free Click Chemistry, J. Am. Chem. Soc. 2008, 130, 11486-11493.

Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.

Coligan et al., Current Protocols in Immunology, sections 2.5.1-2. 6.7, 1991.

Collins et al., Crystal Structures of Oseltamivir-Resistant Influenza Virus Neuraminidase Mutants, Nature, Jun. 26, 2008, 453(7199):1258-1261.

Connor, Robert et al., Receptor Specifcity in Human, Avian, and Equine H2 and H3 Influenza Virus Isolates, Virology, 205: 17, 1994.

Cox et al., New Options for the Prevention of Influenza, N. Engl. J. Med. Oct. 28, 1999, 341(18): 1387-1388.

Cragg, M.S. et al., Complement-Mediated Lysis By Anti-CD20 mAb Correlates with Segregation into Lipid Rafts, Blood 101 (2003) 1045-1052.

Cragg, M.S. et al., Antibody Specificity Controls in Vivo Effector Mechanism of Anti-CD20 Reagents, Blood, 103 (2004) 2738-2743.

Craigo, J. K., Montelaro, R. C. Lessons in AIDS vaccine development learned from studies of equine infectious, anemia virus infection and immunity. Viruses 5, 2963-76, (2013.

Crispin et al., "Carbohydrate and domain architecture of an immature antibody glycoform exhibiting enhanced effector functions," J. Mol. Biol., Apr. 17, 2009, 387(5):1061-1066.

Cunningham et al., "High-resolution epitope mapping of hGH-receptor interactions by alanine-scanning mutagenesis," Science, Jun. 2, 1989, 244(4908):1081-1085.

Cyranoski, Threat of Pandemic Brings Flu Drug Back to Life, Nat. Med. Sep. 2005, 11(9): 909.

Daëron, "Fc receptor biology," Ammm. Rev. Immunol., 1997, 15:203-234.

Davies, JW et al., Streamlining Lead Discovery by Aligning in Silico and High-Throughput Screening, Curr Opin Chem Biol. Aug. 2006; 10(4):343-51.

Davodeau et al., "Close phenotypic and functional similarities between human and murine αβ T cells expressing invariant TCR alpha-chains," J. Immunol., Jun. 15, 1997, 158(12):5603-5611.

De Almeida et al., "Thiacycloalkynes for copper-free click chemistry," Angew. Chem. Int. Ed. Engl., Mar. 5, 2012, 51(10):2443-2447.

Debets, M. F. et al., Bioconjugation with Strained Alkenes and Alkynes, Acc. Chem. Res. 2011, 44, 805-815.

De Haas et al., "Fcγ receptors of phagocytes," J. Lab. Clin. Med., Oct. 1995, 126(4):330-341.

Dejong et al., Fatal outcome of human influenza A (H5N1) is associated with high viral load and hypercytokinemia. Nat Med Oct. 2006; 12(10): 1203-7. Epub Sep. 10, 2006.

Delente, Jacqubs, Glycosylation Revisited, Trends in Biotechnology 3, letters to editor, No. 9 (1985).

Dellabona et al., "An invariant Vα24-JαQ/Vβ11 T cell receptor is expressed in all individuals by clonally expanded CD4$^{-8-\ T\ cells}$," J. Exp. Med., Sep. 1, 1994, 180(3):1171-1176.

Demchenko, A.V., Ed., Hanbook of Chemical Glycosylation: Advances in Stereoselectivity and Therapeutic Relevance (2008) Wiley-VCH. Chapter 1. General Aspects of the Glycosidic Bond Formation, in 28 pages.

Dennis, Carina, Cancer: Off by a whisker, Nature 442: 739-741 (2006).

De Paz, J. L., Horlacher, T. & Seeberger, P.H. Oligosaccharide microarrays to map interactions of carbohydrates in biological systems. Methods Enzymol. 415, 269-292, (2006).

Dhodapkar et al., "α-Galactosyl ceramide-loaded dendritic cells for expansion of natural killer T cells" CAPLUS 145:354715 (2006).

Dhodapkar et al., "A reversible defect in natural killer T cell function characterizes the progression of premalignant to malignant multiple myeloma," J. Exp. Med., Jun. 16, 2003, 197(12):1667-1676.

Dicker, Martina et al., Using Glyco-Engineering to Produce Therapeutic Proteins, Expert Opinion on Biological Therapy, vol. 15, Jan. 1, 2015, pp. 1501-1516.

(56) References Cited

OTHER PUBLICATIONS

Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.
Dohi, H. et al., Stereoselective Glycal Fluorophosphorlation: Synthesis of ADP-2-Fluoroheptose, an Inhibitor of the LPS Biosynthesis, Chem-Eur J 2008, 14, 9530-9539.
Dommerholt, Jan, Readily Accessible Bicyclononynes for Bioorthogonal Labeling and Three-Dimensional Imaging of Living Cells, Angew. Chem. Int. Ed. 2010, 49, 9422-9425.
Doores KJ, et al. A nonself sugar mimic of the HIV glycan shield shows enhanced antigenicity. Proc. Natl. Acad Sci. US.A. 107(40), 17107-17112, (2010).
Doores, K. J. & Burton, D.R. Variable Loop Glycan Dependency of the Broad and Potent HIV-I-Neutralizing Antibodies PG9 and PG16. J. Virol. 84, 10510-10521, (2010).
Doores, K. J. et al. Envelope glycans of immunodeficiency virions are almost entirely oligomannose antigens. Proc. Natl. Acad. Sci. U. S. A 107, 13800-13805, (2010).
Doronina, Svetlana et al., Development of Potent Monoclonal Antibody Auristatin Conjugates for Cancer Therapy, Nat Biotechnol 21(7): 778-784 (2003).
Dougan, Michael et al., Immune Therapy for Cancer, Annual Review of Immunology, 2009, 27, p. 83-117.
Rabasseda, X., et al. "Gemtuzmab Ozogamicin" Drugs of the Future 25(7): 686-692 (2000).
Dubertret. Benoit et al., In Vivo Imaging of Quantum Dots Encapsulated in Phospholipid Micelles, Science 298:759-1762, 2002.
Duncan, AR; Winter, G, The binding Site for C1q on IgG, Nature 322:738-40 (1988).
Dunn et al., Zanamivir: A Review of Its Use in Influenza, Drugs, Oct. 1999, 58(4):761-784.
Durrant et al., "Immunology in the clinic review series; focus on cancer: glycolipids as targets for tumour immunotherapy," Clin. Exp. Immunol., Feb. 2012, 167(2):206-215.
Eberl et al., "Selective bystander proliferation of memory CD4$^+$ and CD8$^+$ T cells upon NK T or T cell activation," J. Immunol., Oct. 15, 2000, 165(8):4305-4311.
Eberl et al., "Selective induction of NK cell proliferation and cytotoxicity by activated NKT cells," Eur. J. Immunol., Apr. 2000, 30(4):985-992.
Eggink, D. et al. Lack of complex N-glycans on HIV-I envelope glycoproteins preserves protein conformation and entry function. Virology 401, 236-247, (2010).
Eisen, Michael et al., Binding of the Influenza A Virus to Cell-Surface Receptors: Structures of Five Hemagglutinin-Sialyloligosaccharide Complexes Determined By X-Ray Crystallography, Virology, 232:19, 1997.
Ellis J., et al., Evaluation of Four Real-Time PCR Assays for Detection of Influenza A9H1N1)v Viruses, Euro Surveill. 2009; 14(22), p. 1-3.
Embleton et al., "In-cell PCR from mRNA: amplifying and linking the rearranged immunoglobulin heavy and light chain V-genes within single cells," Nucl. Acids Res., Aug. 11, 1992, 20(15):3831-3837.
Engels et al., "Gene synthesis [new synthetic methods (77)]," Angew. Chem. Int. Ed. Engl., Jun. 1989, 28(6):716-734.
European Search Report issued in connection with corresponding European Patent Application No. 15181446.4, Dec. 7, 2015, 10 pages.
Evans, Michael et al., "Mechanism-based profiling of enzyme families," Chem. Rev., Aug. 2006, 106(8):3279-3301.
Evans, "The rise of azide-alkyne 1,3-dipolar 'click' cycloaddition and its application to polymer science and surface modification," Australian J. Chem., Jun. 2007, 60(6):384-395.
Extended European Search Report dated Jan. 5, 2016 in European Patent Application No. 13830785.5, in 10 pages.
Extended European Search Report, App. No. 15799789.1, dated Nov. 28, 2017, 10 Pages.
Extended European Search Report, App. No. 15800191.7, dated Nov. 28, 2017, 12 Pages.
Extended European Search Report, App. No. 15799981.4, dated Nov. 29, 2017, 9 Pages.
Falkowska, E. et al. Broadly neutralizing HIV antibodies define a glycan-dependent epitope on the prefusion conformation of gp41 on cleaved envelope trimers. Immunity 40, 657-68, 2014.
Fan, Shu-Quan et al., Remarkable Transglycosylation Activity of Glycosynthase Mutants of Endo-D, an Endo-β-N-acetylglucosaminidase from Streptococcus pneumoniae, JBC vol. 287, No. 14, pp. 11272-11281, Mar. 30, 2012.
Fazio, F. et al., Synthesis of sugar arrays in microtiter plate. J. Am. Chem. Soc. 124, 14397-14402, (2002).
FDA Guidance for Industry for Container Closure Systems for Packaging Human Drugs and Biologics, May 1999, pp. 1-56.
Fedson, Confronting the next influenza pandemic with anti-inflammatory and immunomodulatory agents: why they are needed and how they might work. Influenza Other Respi Viruses. Jul. 2009;3(4):129-42.
Feizi, Ten, Carbohydrate Differentiation Antigens: Probable Ligands for Cell Adhesion Molecules,Trends Biochem. Sci. 1991, 16, 84-86.
Fellouse et al., "Synthetic antibodies from a four-amino-acid code: a dominant role for tyrosine in antigen recognition," Proc. Natl. Acad. Sci. U.S.A., Aug. 24, 2004, 101(34):12467-12472.
Fernandez-Tejada, Alberto et al., Designing synthetic vaccines for HIV. Expert Rev. Vaccines 14, 815-31, 2015.
Fernandez-Megia et al., A Click Approach to Unprotected Glycodendrimers. Macromolecules 2006, vol. 39, pp. 2113-2120.
Fessner et al., Enzymes in Organic Synthesis, Short Enzymatic Synthesis of L-Fucose Analogs. Eur. J. Org. Chem 2000, p. 125-132.
Fiehn, Oliver, Combining Genomics, Metabolome Analysis, and Biochemical Modelling to Understand Metabolic Networks, Comparative and Functional Genomics 2:155-168, 2001.
Fishwild et al., "High-avidity human IgGK monoclonal antibodies from a novel strain of minilocus transgenic mice," Nature Biotechnol., Jul. 1996, 14(7):845-851.
Fraker, PJ et al., Protein and Cell Membrane Iodinations with a Sparingly Soluble Chloroamide, 1,3,4,6-tetrachloro-3a,6a-diphrenylglycoluril, Biochem. Biophys. Res. Commun. 80: 49-57 (1978).
Frank, Natasha et al., The Therapeutic Promise of the Cancer Stem Cell Concept, Journal of Clinical Investigation, 120(1) 41-50, Jan. 2010.
Fredman et al., "Expression of gangliosides GD3 and 3'-isoLM1 in autopsy brains from patients with malignant tumors," J. Neurochem., Jan. 1993, 60(1):99-105.
Fredman et al., "Potential ganglioside antigens associated with human gliomas," Neurol. Res., Jun. 1986, 8(2): 123-126.
Fredman et al., "Sialyllactotetraosylceramide, a ganglioside marker for human malignant gliomas," J. Neurochem., Mar. 1988, 50(3):912-919.
Friscourt, F. et al., A Fluorogenic Probe for the Catalyst-Free Detection of Azide-Tagged Molecules, J. Am. Chem. Soc. 2012, 134, 18809-18815.
Friscourt et al., "Polar Dibenzocyclooctynes for Selective Labeling of Extracellular Glycoconjugates of Living Cells," J. Am. Chem. Soc., Mar. 21, 2012, 134(11):5381-5389.
Fujimore, Kenji et al., A Modeling Analysis of Monoclonal Antibody Percolation Through Tumors: A Binding-Site Barrier, J Nuc Med. 31: 1191-1198 (1990).
Fujio, M. et al. "Structure-Based Discovery of Glycolipids for CD1d-Mediated NKT Cell Activation: Turning the Adjuvant versus Immunosuppression Activity." CAPLUS 145:240945 (2006).
Fujio, M. et al. "Structure-Based Discovery of Glycolipids for CD1d-Mediated NKT Cell Activation: Turning the Adjuvant versus Immunosuppression Activity." J. Am. Chem. Soc. (2006), vol. 128, pp. 9022-9023.
Fujita M et al., "A novel disaccharide substrate having 1,2-oxazoline moiety for detection of transglycosylating activity of endoglycosidases" Biochim Biophys Acta. Sep. 3, 2001;1528(1):9-14.

(56) References Cited

OTHER PUBLICATIONS

Fukui, S et al., Oligosaccharide microarrays for high-throughput detection and specificity assignments of carbohydrate-protein interactions. Nat. Biotechnol. 20, 1011-1017, (2002).

Gabius, HJ. Tumor Lectinology: at the intersection of carbohydrate chemistry, biochemistry, cell biology and oncology. Angew. Chem. Int. Ed. Engl. 1988, 27, 1267-1276.

Galfre et al., "Preparation of monoclonal antibodies: strategies and procedures," Methods Enzymol., 1981, 73(Pt B):3-46.

Gamblin, SJ et al., The Structure and Receptor Binding Properties of the 1918 Influenza Hemagglutinin, Science, 303:1838, 2004.

Garces, F. et al. Structural evolution of glycan recognition by a family of potent HIV antibodies. Cell 159, 69-79, (2014).

Gaschen, B. et al. AIDS—Diversity Considerations in HIV-I vaccine selection. Science 296, 2354-2360, (2002).

Gazzano-Santoro et al., "A non-radioactive complement-dependent cytotoxicity assay for anti-CD20 nonclonal antibody," J. Immunol. Methods, Mar. 28, 1997, 202(2):163-171.

Geiler et al., Comparison of pro-inflammatory cytokine expression and cellular signal transduction in human macrophages infected with different influenza A viruses. Med Microbiol Immunol. Feb. 2011;200(1):53-60.

GenBank accession No. AAA24922.1, "endoglycosidase F [Elizabethkingia meningoseptica]," May 27, 2008.

GenBank accession No. AAA24923.1, "endoglycosidase, partial [Elizabethkingia meningoseptica]," Jun. 8, 1993.

GenBank accession No. AAA24924.1, "endoglycosidase, partial [Elizabethkingia meningoseptica]," Jun. 7, 1993.

GenBank accession No. AAA26738.1, "endo-beta-N-acetylglucosaminidase H [Streptomyces plicatus]," Apr. 26, 1993.

GenBank accession No. J05449.1, "F.meningosepticum peptide-N-4-(N-acetyl-beta-D-glucosaminyl) asparagine amidase (PNGase F) mRNA, complete cds," Jan. 16, 1996.

GenBank accession No. YP_212855.1, "Putative exported alpha-L-fucosidase protein [Bacteroides fragilis NCTC 9343]," Mar. 2, 2014.

GenBank accession No. WP_008769537.1, published May 10, 2013.

GenBank accession No. WP_008767711.1, published May 10, 2013.

Geoghegan, Kieran et al., Site-Directed Conjugation of Nonpeptide Groups to Peptides and Proteins Via Periodate Oxidation of a 2-amino Alcohol. Applications to Modification at N-Terminal Serine, Bioconjugate chem. 3:138-146 (1992).

Gerson et al., "ESR. Spectra and Structures of Radical Anions in the Dibenzo[a, e]cyclooxtene Series," Helvetica Chinica Acta, Jan. 1, 1976, 59(6): 2038-2048.

Giaccone, Giuseppe et al., "A phase I study of the natural killer T-cell ligand α-galactosylceramide (KRN7000) in patients with solid tumors," Clin. Cancer Res., Dec. 2002, 8(12):3702-3709.

Gill et al., "Direct brain infusion of glial cell line-derived neurotrophic factor in Parkinson disease," Nature Med., May 2003, 9(5):589-595 and Addendum from Apr. 2006, 12(4):479.

Go, E. P. et al. Characterization of glycosylation profiles of HIV-I transmitted/founder envelopes by mass spectrometry. J. Virol. 85, 8270-8284, (2011).

Go, E. P. et al. Comparative Analysis of the Glycosylation Profiles of Membrane-Anchored HIV-I Envelope Glycoprotein Trimers and Soluble gp140. J. Virol. 89, 8245-57, (2015).

Godefroy, S. et al., Effect of Skin Barrier Disruption on Immune Responses to Topically Applied Cross-Reacting Material, CRM197 of Diphtheria Toxin, Infect. Immun 2005, 73, 4803.

Goding, Monoclonal Antibodies: Principles and Practice 2nd ed., Chapter 3: Production of Monoclonal Antibodies, 1986, pp. 59-103, Academic Press, London.

Goldenthal et al., "Safety Evaluation of Vaccine Adjuvants: National Cooperative Vaccine Development Working Group," AIDS Res. Hum. Retroviruses, 1993, 9(Supp. 1):S47-S51.

Golkowski et al., "Strategy for catch and release of azide-tagged biomolecules utilizing a photolabile strained alkyne construct," Organic and Biomolecular Chemistry, Jan. 1, 2012, 10(23):4496.

Goochee CF et al., "The oligosaccharides of glycoproteins: bioprocess factors affecting oligosaccharide structure and their effect on glycoprotein properties", Biotechnology (N Y). Dec. 1991;9(12):1347-55.

Gordon et al., "Reactivity of biarylazacyclooctynones in copper-free click chemistry," J. Am. Chem. Soc., Jun. 6, 2012, 134(22): 9199-9208.

Gottschling et al., "Stage-specific embryonic antigen-4 is expressed in basaloid lung cancer and associated with poor prognosis," Eur. Respir. J., Mar. 2013, 41(3):656-663.

Govorkova et al., Combination chemotherapy for influenza. Viruses. Aug. 2010;2(8):1510-29.

Graham et al., "Characteristics of a human cell line transformed by DNA from human adenovirus type 5," J. Gen. Virol., Jul. 1977, 36(1):59-72.

Graham, Duncan et al., Surface-Enhanced Resonance Raman Scattering as a Novel Method of DNA Discrimination, Angew. Chem., 2000, 112(6), 1103-1105.

Gram et al., "In vitro selection and affinity maturation of antibodies from a naive combinatorial immunoglobulin library," Proc. Natl. Acad. Sci. U.S.A., Apr. 15, 1992, 89(8):3576-3580.

Grandjean, C. et al., On The Preparation of Carbohydrate-Protein Conjugates Using the Traceless Staudinger Ligation, J Org Chem 2005, 70, 7123-7132.

Green, "Targeting targeted therapy," N. Engl. J. Med., May 20, 2004, 350(21):2191-2193.

Greene, Theodora et al., "Protective Groups in Organic Synthesis," pp. 42-51 and 96-103, 1991.

Greenbaum et al., "Chemical approaches for functionally probing the proteome," Mol. Cell. Proteomics, 2002, 1:60-68.

Griffiths et al., "Human anti-self antibodies with high specificity from phage display libraries," EMBO J., Feb. 1993, 12(2):725-734.

Gruber et al., "Efficient tumor cell lysis mediated by a bispecific single chain antibody expressed in Escherichia coli," J. Immunol., Jun. 1, 1994, 152(11):5368-5374.

Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943.

Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.

Gulland, Fire Cases of Spread of Oseltamivir Resistant Swine Flu Between Patients are Reported in Wales, BMJ, Nov. 23, 2009:339:b4975.

Guss et al., "Structure of the IgG-binding regions of streptococcal protein G," EMBO J., Jul. 1986, 5(7):1567-1575.

Guyer et al., "Immunoglobulin binding by mouse intestinal epithelial cell receptors," J. Immunol., Aug. 1976, 117(2):587-593.

Ha, Ya et al., X-Ray Structures of H5 Avian and H9 Swine Influenza Virus Hemagglutinins Bound to Avian and Human Receptor Analogs, Proc Natl Acad Sci USA, 98:11181-11186, 2001.

Ha, Ya et al., X-Ray Structure of the Hemagglutinin of a Potential H3 Avian Progenitor of the 1968 Hong Kong Pandemic Influenza Virus, Virology, 309:209-218, 2003.

Hajishengallis, "Mucosal immunization with a bacterial protein antigen genetically coupled to cholera toxin A2/B subunits," J. Immuol., May 1, 1995, 154(9):4322-4332.

Hakomori et al., "Glycosphingolipid antigens and cancer therapy," Chem. Biol., Feb. 1997, 4(2):97-104.

Hakomori, "Glycosylation defining cancer malignancy: new wine in an old bottle," Proc. Natl. Acad. Sci. U.S.A., Aug. 6, 2002, 99(16):10231-10233.

Ham, Richard et al., Media and Growth Requirements, Meth. Enz 58, 44 (1979).

Hammerling et al., in: Monoclonal Antibodies and T-Cell Hybridomas 563-587, 1981.

Han, Junyan et al., 3- and 5-Functionalized BODIPYs via the Liebeskind-Srogl Reaction, Organic & Biomolecular Chemistry (2009), 7(1), 34-36.

(56) References Cited

OTHER PUBLICATIONS

Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).
Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).
Hara et al., "Overproduction of penicillin-binding protein 7 suppresses thermosensitive growth defect at low osmolarity due to an spr mutation of *Escherichia coli*." *Microbial Drug Resistance*, Spring 1996, 2(1):63-72.
Harris, "Production of humanized monoclonal antibodies for in vivo imaging and therapy," *Biochem. Soc. Transactions*, Nov. 1995, 23(4):1035-1038.
Hasegawa, Akira, et al., Synthesis of Sialyl Lewis X Ganglioside Analogues Containing Modified L-Fucose Residues, Carbohydr. Res. 1995, 274, 165-181.
Hata, K. et al., Limited Inhibitory Effects of Oseltamivir and Zanamivir on Human Sialidases, Antimicrobial Agents and Chemotherapy, vol. 52, No. 10, Oct. 2008, in 8 pages.
Hawkins et al., "Selection of phage antibodies by binding affinity. Mimicking affinity maturation," *J. Mol. Biol.*, 1992, 226(3):889-896.
Healthy Living, "10 Simple and Natural Ways to Boost Your Immune System," Published Jan. 31, 2014, downloaded from online, http://www.everydayhealth.com/columns/white-seeber-grogan-the-remedy-chicks/ten-simple-natural-ways-to-b . . . on Aug. 19, 2016.
Henglein, A. et al., Absorption Spectrum and Some Chemical Reactions of Colloidal Platinum in Aqueous Solution, J. Phys. Chem., 99, 14129 (1995).
Herner, A et al., A new family of bioorthogonally applicable fluorogenic labelst, Org. Biomol. Chem. 2013, 11, 3297-3306.
Herter et al. "Glycoengineering of therapeutic antibodies enhances monocyte/macrophage-mediated phagocytosis and cytotoxicity" J Immunol. Mar. 1, 2014, vol. 192 No. 5, pp. 2252-2260.
Hey, Thomas et al., Artificial, non-antibody binding proteins for pharmaceutical and industrial application, Trends in Biotechnology 23(10) 514-522 (2005).
Heyman, "Complement and Fc-receptors in regulation of the antibody response," *Immunol. Lett.*, Dec. 1996, 54(2-3): 195-199.
Hinman et al., "Preparation and characterization of monoclonal antibody conjugates of the calicheamicins: a novel and potent family of antitumor antibiotics," *Cancer Res.*, Jul. 15, 1993, 53(14):3336-3342.
Hirabayashi, J. et al., Oligosaccharide Microarrays for Glycomics, Trends in Biotechnology 21 (4): 141-143, 2003.
Hogrefe et al., "A bacteriophage lambda vector for the cloning and expression of immunoglobulin Fab fragments on the surface of filamentous phage," *Gene*, Jun. 15, 1993, 128(1):119-126.
Holliger et al., "'Diabodies': small bivalent and bispecific antibody fragments," *Proc. Natl. Acad. Sci. U.S.A.*, Jul. 15, 1993, 90(14):6444-6448.
Holmskov, Uffe et al., Collectins: Collagenous C-Type Lectins of the Innate Immune Defense System, 1994, Immunol. Today, 15: 67.
Honda et al., Synthesis and anti-influenza virus activity of 7-0-alkylated derivatives related to zanamivir. Bioorg Med Chern Lett. Aug. 5, 2002;12(15):1925-8.
Honegger et al., "Yet another numbering scheme for immunoglobulin variable domains: an automatic modeling and analysis tool," *J. Mol. Biol.*, Jun. 8, 2001, 309:657-670.
Hoogenboom et al., "By-passing immunisation: Human antibodies from synthetic repertoires of germline $V_H$ gene segments rearranged in vitro," *J. Mol. Biol.*, Sep. 20, 1992, 227(2):381-388.
Hoogenboom et al., "Multi-subunit proteins on the surface of filamentous phage: methodologies for displaying antibody (Fab) heavy and light chains," *Nucl. Acids Res.*, Aug. 11, 1991 19(15):4133-4137.

Hotha, Srinivas et al., "Click Chemistry" Inspired Synthesis of Pseudo-Oligosaccharides and Amino Acid Glycoconjugates, J Org Chem 2006, 71, 364-367.
Horiya, S. et al., Recent strategies targeting HIV glycans in vaccine design. Nat. Chem. Biol. 10, 990-999, (2014).
Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.
Howard et al., "Biological properties of interleukin 10," *Immunol. Today*, Jun. 1992, 13(6):198-200.
Hsu et al., "Alkynyl sugar analogs for the labeling and visualization of glycoconjugates in cells," *Proc. Natl. Acad. Sci. USA*, Feb. 20, 2007, 104(8), 2614-2619.
Hsu, C, H. et al. Highly alpha-selective sialyl phosphate donors for efficient preparation of natural sialosides. Chem. Eur. J 16-6, 1754-1760, (2010).
Hsu, Nien-Yeen et al., Desorption Ionization of Biomolecules on Metals, Anal. Chem., 80, 5203-5210, 2008.
Huang et al., "Carbohydrate-based vaccines with a glycolipid adjuvant for breast cancer," *Proc. Natl. Acad. Sci. U.S.A.*, Feb. 12, 2013, 110(7):2517-2522.
Huang, Wei et al., Chemoenzymatic Glycoengineering of Intact IgG Antibodies for Gain of Functions, Journal American Chemical Socirty, vol. 134, No. 9, Jul. 25, 2012, pp. 12308-12318.
Huang, Lijun et al., Iterative One-Pot Syntheses of Chitotetroses, Carbohydr. Res. 2006, 341, 1669-1679.
Huang et al., Recombinant immunotherpaeutics: current state and perspectives regarding the feasibility and market, Appl Microbiol Biotechnol, 87: 401-410. 2010.
Hung et al., "Investigation of SSEA-4 binding protein in breast cancer cells," *J. Am. Chem. Soc.*, Apr. 24, 2013, 135(16):5934-5937.
Hurle et al., "Protein engineering techniques for antibody humanization," *Curr. Opin. Biotechnol.*, Aug. 1994, 5(4):428-433.
Immunogenicity, Wikipedia p. 1-3. Downloaded on Aug. 16, 2016 from https://en.wikipedia.org/wiki/Immunogenicity. (2016).
Inouye et al., "Single-step purification of $F(ab')_{2\mu}$ fragments of mouse monoclonal antibodies (immunoglobulins M) by hydrophobic interaction high-performance liquid chromatography using TSKgel Ether-5PW," *J. Biochem. Biophys. Methods*, Feb. 1993, 26(1):27-39.
International Search Report and Written Opinion issued for International application No. PCT/US2015/011748, dated Aug. 21, 2015, 27 pages.
International Search Report and Written Opinion issued for International application No. PCT/US2015/032737, dated Oct. 1, 2015, 13 pages.
International Search Report and Written Opinion issued for International application No. PCT/US2015/032738, dated Oct. 20, 2015, 15 pages.
International Search Report and Written Opinion issued for International application No. PCT/US2015/032740, dated Oct. 26, 2015, 13 pages.
International Search Report and Written Opinion issued for International application No. PCT/US2015/032744, dated Oct. 2, 2015, 12 pages.
International Search Report and Written Opinion issued for International application No. PCT/US2015/032745, dated Oct. 8, 2015, 13 pages.
International Search Report dated Jan. 13, 2012, from corresponding International Patent Application No. PCT/US2011/035982, 17 pages.
International Search Report dated Nov. 13, 2014, from corresponding International Patent Application No. PCT/US2014/054617, 10 pages.
International Search Report issued for International application No. PCT/US2015/049014, dated Dec. 14, 2015, 3 pages.
International Search Report and Written Opinion in International Application No. PCT/US16/15858, dated Jun. 27, 2016, in 8 pages.
International Search Report issued for International application No. PCT/US15/22977, dated Jun. 22, 2015, 3 pages.
International Search Report issued for International application No. PCT/US15/40199, dated Mar. 2, 2016, 6 pages.

(56) References Cited

OTHER PUBLICATIONS

International Search Report issued for International application No. PCT/US2009/050754, dated Feb. 24, 2010, 11 pages.
International Search Report and Written Opinion in International Application No. PCT/US2017/021454, dated Jul. 31, 2017, 17 pages.
International Search Report and Written Opinion in International Application No. PCT/US2017/048074, dated Dec. 26, 2017, 17 pages.
Isshiki et al., Cloning, Expression, and Characterization of a Novel UDP-galactose:b-N-Acetylglucosamine b1,3-Galactosyltransferase (b3Gal-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.
Ito, Akihiro et al., A Novel Ganglioside Isolated From Renal Cell Carcinoma, Biol Chem 2001, 276, 16695.
Jackson et al., "In vitro antibody maturation: Improvement of a high affinity, neutralizing antibody against IL-1β," *J. Immunol.*, Apr. 1, 1995, 154(7):3310-3319.
Jacobs et al., "Metabolic labeling of glycoproteins with chemical tags through unnatural sialic acid biosynthesis," *Methods Enzymol.*, 2000, 327:260-275.
Jakobovits et al., "Analysis of homozygous mutant chimeric mice: deletion of the immunoglobulin heavy-chain joining region blocks B-cell development and antibody J production," *Proc. Natl. Acad. Sci. U.S.A.*, Mar. 15, 1993, 90(6):2551-2555.
Jakobovits et al., "Germ-line transmission and expression of a human-derived yeast artificial chromosome," *Nature*, Mar. 18, 1993, 362(6417):255-258.
Japanese Office Action dated Apr. 21, 2015, from Related Japanese Patent Application No. 2013-510261, 6 Pages.
Jayasena, Sumedha, Aptamers: An Emerging Class of Molecules That Rival Antibodies in Diagnostics, Clin. Chem. (1999), 45, 1628-1650.
Jenkins N, Curling EM., "Glycosylation of recombinant proteins: problems and prospects", *Enzyme Microb Technol.* May 1994;16(5):354-64.
Jewett, J.C.; Bertozzi, C.R., Cu-Free Click Cycloaddition Reactions in Chemical Biology, Chem. Soc. Rev. 2010, 39, 1272-1279.
Jewett, J.C.; Sletten, E. M.; Bertozzi, C.R., Rapid Cu-Free Click Chemistry with Readily Synthesized Biarylazacyclooctynones, J. Am. Chem. Soc. 2010, 132, 3688-3690.
Jewett et al., "Synthesis of a fluorogenic cyclooctyne activate by Cu-free click chemistry," *Org. Lett.*, Nov. 18, 2011, 13(22):5937-5939.
Jez et al. "Significant Impact of Single N-Glycan Residues on the Biological Activity of Fc-based Antibody-like Fragments" Journal of Biological Chemistry Jul. 13, 2012, vol. 287 No 29, pp. 24313-24319.
Jin, R. C. et al., Photoinduced Conversion of Silver Nanospheres to Nanoprisms, Science (2001), 294, 1901-1903.
Jobling, Michael et al., Fusion Proteins Containing the A2 Domain of Cholera Toxin Assemble With B Polypeptides of Cholera Toxin To Form Immunoreactive and Functional Holotoxin-Like Chimeras, Infect Immun., 60: 4915-24, 1992.
John, F. & Hendrickson, T. L. Synthesis of Truncated Analogues for Studying the Process of Glycosyl Phosphatidylinositol Modification. Org. Lett. 12, 2080-2083, (2010).
Jones et al., "Rapid PCR-cloning of full-length mouse immunoglobulin variable regions," *Nature Biotechnol.*, Jan. 1991, 9(1):88-89.
Jones et al., "Replacing the complementarity-determining regions in a human antibody with those from a mouse," *Nature*, May 29-Jun. 4, 1986, 321(6069):522-525.
Jones, "Analysis of polypeptides and proteins," *Adv. Drug Delivery Rev.*, Jan.-Apr. 1993, 10(1):29-90.
Jonges, M. et al., Dynamics of Antiviral-Resistant Influenza Viruses in the Netherlands, 2005-2008, Antiviral Res., Sep. 2009, 83(3): 290-297.
Jorgensen, Trond et al., Up-Regulation of the Oligosaccharide Sialyl Lewisx: A New Prognostic Parameter in Metastatic Prostate Cancer, Cancer Res. 55, 1817-1819, 1995.
Jose, Jiney et al., Energy transfer dyads based on Nile Red, Tetrahedron Letters (2009), 50(47), 6442-6445.
Joshi, Shantaran et al., Cell Surface Properties Associated with Malignancy of Metastatic Large Cell Lymphoma Cells, (1987) Cancer Res. 47, 3551-3557.
Joyce, J. G. et al. An oligosaccharide-based HIV-I 2G12 mimotope vaccine induces carbohydrate-specific antibodies that fail to neutralize HIV-I virions. Proc. Natl. Acad. Sci. U. S. A 105, 15684-15689, (2008).
Junttila et al. "Superior in vivo efficacy of afucosylated trastuzumab in the treatment of HER2-amplified breast cancer" Cancer Res. 2010, vol. 70 No. 11, pp. 4481-4489.
Kakeji, Y. et al., Correlation Between Sialyl Tn Antigen and Lymphatic Metastasis in Patients with Borrmann Type IV Gastric Carcinoma, Brit. J. Cancer 71, 191-195, 1995.
Kale et al., Detection of intact influenza viruses using biotinylated biantennary S-sialosides. J Am Chem Soc. Jul. 2, 2008;130(26):8169-71.
Kalesh et al., "Peptide-based activity-based probes (ABPs) for target-specific profiling of protein tyrosine phosphatases (PTPs)," *Chem. Commun.*, Jan. 28, 2010, 46(4):589-591.
Kamkaew, A. et al., "BODIPY dyes in photodynamic therapy." Chem. Soc. Rev. 2013, 42, 77-88.
Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.
Kaneko et al., "Anti-inflammatory activity of immunoglobulin G resulting from Fc sialylation," *Science*, Aug. 4, 2006, 313(5787):670-673.
Kawakami et al., "Critical role of Vα14+ natural killer T cells in the innate phase of host protection against Streptococcus pneumoniae infection," *Eur. J. Immunol.*, Dec. 2003, 33(12):3322-3330.
Kawano et al., "CD1d-restricted and TCR-mediated activation of $v_α14$ NKT cells by glycosylceramides," *Science*, Nov. 28, 1997, 278(5343): 1626-1629.
Kanie, Osman et al., Orthogonal glycosylation strategy in synthesis of extended blood group B determinant. Tetrahedron Lett. 37, 4551-4554 (1996).
Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.
Kannagi et al., "Stage-specific embryonic antigens (SSEA-3 and -4) are epitopes of a unique globo-series ganglioside isolated from human teratocarcinoma cells," *EMBO J.*, 1983, 2(12):2355-2361.
Kannappan, Ramaswamy et al., "Photoaffinity labeling of sialidase with a biotin-conjugated phenylaminodizairine derivative of 2,3-didehydro-2-deoxy-N-acetylneuraminic acid," *Biol. Pharm. Bull.*, Mar. 2008, 31(3):352-356.
Karlin, Samuel et al., Applications and Statistics for Multiple High-Scoring Segments in Molecular Sequences, Proc. Natl. Acad Sci. USA 90:5873-77, 1993.
Karlin S. et al., "Methods for assessing the statistical significance of molecular sequence features by using general scoring schemes", *Proc Natl Acad Sci USA.* Mar. 1990;87(6):2264-8.
Karmakar, M. et al., Current Trends in Research and Application of Microbial Cellulases, Research Journal of Microbiology, (2011) 6(1): 41-53.
Katagiri, Yohko et al., Laminin Binding Protein, 34/67 Laminin Receptor, Carries Stage-Specific Embryonic Antigen-4 Epitope Defined By Monoclonal Antibody Raft.2, Biochemical and Biophysical Research Communcations, 332, 1004-1011, 2005.
Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.
Kermani, Pouneh et al., Production of ScFv Antibody Fragments Following Immunization with a Phage-Displayed Fusion Protein

(56) References Cited

OTHER PUBLICATIONS and Analysis of Reactivity to Surface-Exposed Epitopes of the Protein F of Pseudomonas Aeruginosa by Cytofluorometry, Hybridoma, 14(4):323-328 (1995).
Kidd et al., "Profiling serine hydrolase activities in complex proteomes," *Biochemistry*, Apr. 3, 2001, 40(13):4005-4015.
Kiick, K.L. et al., Identificationof an Expanded Set of Translationally Active f Methionine Analogues in *Escherichia coli*, FEBS Letters 56:9487, 2001.
Kim et al., "Localization of the site of the murine IgG1 molecule that is involved in binding to the murine intestinal Fc receptor," *Eur. J. Immunol.*, 1994, 24:2429-2434.
Kim et al., High-Throughput Screening of Glycan-Binding Proteins Using Miniature Pig Kidney N-Glycan-Immobilized Beads, Chemistry & biology 15.3, p. 215-223 (2008).
Kim, Gap-Sue et al., Synthesis, linear extinction, and preliminary resonant hyper-Rayleigh scattering studies of gold-core/silver-shell nanoparticles: comparisons of theory and experiment, Chem Phys. Lett., 2002, 3 5 2, 421-428.
Kimura et al., Design and Synthesis of Immobilized Tamiflu Analog on Resin for Affinity Chromatography, Tetrahedron Lett., Jul. 1, 2009, 50(26):3205-3208.
King, M. et al., New Tetramethlthiepinium (TMTI) For Copper-Free Click Chemistry, Chem. Commun. 2012, 48, 9308-9309.
Kitamura et al., "α-galactosylceramide induces early B-cell activation through IL-4 production by NKT cells," *Cell. Immunol.*, Jan. 10, 2000, 199(1):37-42.
Klein, J. et al., "Isomaltines and their N-acyl derivatives, their preparation, and use of some acyl derivatives as surfactants or for preparation of hydrophilic polymers," CAPLUS 110:95711 (1989).
Köhler et al., "Continuous cultures of fused cells secreting antibody of predefined specificity," *Nature*, Aug. 7, 1975, 256(5517):495-497.
Kolb et al., "Click chemistry: diverse chemical function from a few good reactions,"*Angew. Chem. Int. Ed. Engl.*, Jun. 1, 2001, 40(11):2004-2021.
Kolb et al., "The growing impact of click chemistry on drug discovery," *Drug Discov. Today*, Dec. 15, 2003, 8(24): 1128-1137.
Komarova et al. "Plant-Made Trastuzumab (Herceptin) Inhibits HER2/Neu+ Cell Proliferation and Retards Tumor Growth" PLOS ONE 2011,vol. 6 No. 3, p. e17541.
Komba S, et al. Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.
Komori, Tatsuya et al., Study on Systematizing the Synthesis of the A-Series Ganglioside Glycans GT1a, GD1a, and GM1 Using the Newly Developed N-Troc-Protected GM3 and GalN Intermediates, Carbohydr. Res. 2009, 344, 1453.
Kong, L. et al. Expression-system-dependent modulation of HIV-I envelope/glycoprotein antigenicity and immunogenicity. J. Mol. Biol. 403, 131-147, (2010).
Kontermann, "Intrabodies as therapeutic agents," *Methods*, Oct. 2004, 34(2):163-170.
Kos, "Regulation of adaptive immunity by natural killer cells," *Immunol. Res.*, 1998, 17(3):303-312.
Koshihara et al., "Caffeic acid is a selective inhibitor for leukotriene biosynthesis," Biochmica et biophysica acta, 1984, 792(1), pp. 92-97.
Kostelny et al., "Formation of a bispecific antibody by the use of leucine zippers," *J. Immunol.*, Mar. 1, 1992, 148(5): 1547-1553.
Kotteas et al., Immunotherapy for pancreatic cancer, J cancer Res Clin Oncol, 142(8): 1795-1805, 2016.
Kozbor, "A human hybrid myeloma for production of human monoclonal antibodies," *J. Immunol.*, Dec. 1984, 133(6):3001-3005.
Kriegler M et al., "A novel form of NF/cachectin is a cell surface cytotoxic transmembrane protein: ramifications for the complex physiology of TNF" *Cell.* Apr. 8, 1988;53(1):45-53.

Krise, Jeffrey et al., Prodrugs of Phosphates, Phosphonates, and Phosphinates, Adv. Drug Deliv. Rev. 1996, 19(2), 287-310.
Kruis et al., Low dose balsalazide (1.5 g twice daily) and mesalazine (0.5 g three times daily) maintained remission of ulcerative colitis but high dose alsalazide (3.0 g twice daily) was superior in preventing relapses. Gut. Dec. 2001;49(6):783-9.
Kubin, R. F. et al., Fluorescence Quantum Yields of Some Rhodamine Dyes, Luminescence 1982, 27, 455-462.
Kubler-Kielb, J. et al., A New Method for Conjugation of Carbohydrates to Proteins Using an Aminooxy-Thiol Heterbifunctional Linker, J Org Chem 2005, 70, 6987-6990.
Kudo et al., "Up-regulation of a set of glycosyltransferase genes in human colorectal cancer," *Lab. Invest.*, Jul. 1998, 78(7):797-811.
Kwong, Peter et al., Rational Design of Vaccines to Elicit Broadly Neutralizing Antibodies to HIV-I. Cold Spring Harb.Perspect. Med. 1, 2011, 1-16.
Lantz et al., "An invariant T cell receptor α chain is used by a unique subset of major histocompatibility complex class I-specific $CD4^+$ and $CD4^-8^-$ T cells in mice and humans," *J. Exp. Med.*, Sep. 1, 1994, 180(3):1097-1106.
Lau et al., "N-Glycans in cancer progression," *Glycobiology*, Oct. 2008, 18(10):750-760.
Lau, K. et al. Highly efficient chemoenzymatic synthesis of β1-4-linked galactosides with promiscuous bacterial β1-4-galactosyltransferases. Chem. Commun. 46, 6066-6068, (2010).
Le, Mai et al., Avian flu: Isolation of Drug-Resistant H5N1 Virus, Nature, Oct. 20, 2005, 437(7062):1108.
Lebens et al., Mucosal vaccines based on the use of cholera toxin B as immunogen and antigen carrier, *Dev. Biol. Stand.*, 1994, 82:215-227.
Le Droumaguet, C. et al., Fluorogenic Click Reaction., Chem. Soc. Rev. 2010, 39, 1233-1239.
Lederman et al., A single amino acid substitution in a common African allele of the CD4 molecule ablates binding of the monoclonal antibody, OKT4, Molecular Immunology, 28, 1171-1181 (1991).
Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.
Lee et al., "Bivalent antibody phage display mimics natural immunoglobulin," *J. Immunol. Methods*, Jan. 2004, 284(1-2):119-132.
Lee et al., "High-affinity human antibodies from phage-displayed synthetic Fab libraries with a single framework scaffold," *J. Mol. Biol.*, Jul. 23, 2004, 340(5):1073-1093.
Lee et al., A new Solvent System for Efficient Synthesis of 1,2,3-Triazoles, Tetrahedron Lett., Jul. 17, 2006, 47(29):5105-5109.
Lee et al., An Efficient and Practical Method for the Synthesis of Mono-N-Protected α,ω-diaminoalkanes, Tetrahedron Lett., Apr. 2, 2001, 42(14):2709-2711.
Lee, H.K. et al. Reactivity-based one-pot synthesis of oligomannoses: defining antigens recognized by 2G12, a broadly neutralizing anti-HIV-I antibody. Angew. Chem. Int. Ed. 43, 1000-1003, (2004.
Lee et al., Immunogenicity Study of Globo H Analogues with Modification at the Reducing or Nonreducing end of the tumor antigen, J Am Chem Soc, 136: 16844-16853 (2014).
Lefranc et al., "IMGT, the international ImMunoGeneTics database," *Nucleic Acids Res.*, Jan. 1, 1999, 27(1):209-212.
Lehninger, *Biochemistry: The Molecular Basis of Cell Structure and Function*, $2^{nd}$. ed., 1975, pp. 73-75, Worth Publishers, New York.
Lei, Jianqing et al., Potential antitumor applications of a monoclonal antibody specifically targeting human papilloma virus 16 E749-57 peptide, Microbiology and Immunology, 2012, vol. 56, pp. 456-462.
Lemieux, R. U. et al., Halide ion catalyzed glycosidation reactions. Syntheses of a-linked disaccharides. J Am. Chem. Soc. 97(14), 4056-62, (1975).
Leung et al., "A method for random mutagenesis of a defined DNA segment using a modified polymerase chain reaction," *Technique—A Journal of Methods in Cell and Molecular Biology*, Aug. 1989, 1(1):11-15.
Lew et al., Discovery and Development of GS 4104 (oseltamivir): an Orally Active Influenza Neuraminidase Inhibitor, Curr Med Chem, Jun. 2000, 7(6):663-672.

(56) References Cited

OTHER PUBLICATIONS

Li et al., β-endorphin omission analogs: Dissociation of Immunoreactivity from other biological activities, Proc Natl Avad Sci USA, 77:3211-3214 (1980).

Li, Y. et al., "Adapting cDNA microarray format to cytokine detection protein arrays," Langmuir 19.5 (2003): 1557-1566.

Li, Henghui et al., MALDI-MS Analysis of Sialylated N-Glycan Linkage Isomers Using Solid-Phase Two Step Derivatization Method, Analytica Chimica Acta 924 (2016) 77-85.

Li et al., "Design of a potent CD1d-binding NKT cell ligand as a vaccine adjuvant," Proc. Natl. Acad. Sci. USA, Jul. 20, 2010, 107:13010-13015.

Li, J.; Hu, M.; Yao, S. Q. "Rapid synthesis, screening, and identification ofxanthone and xanthene-based fluorophores using click chemistry." Org. Lett. 2009, 11, 3008-3011.

Li, Lingling, et al., "Syntheses and spectral properties of functionalized, water-soluble BODIPY derivatives." J. Org. Chem. 2008, 73, 1963-1970.

Li, L. et al. Efficient chemoenzymatic swisemanynthesis of an N-glycan isomer library. Chem. Sci. 6, 5652-5661 (2015).

Liang, Yuh-Jin et al., Switching of the Core Structures of Glycosphingolipids From Blobo- and Lacto- to Ganglio-Series Upon Human Embryonic Stem Cell Differentiation, PNAS, 107(52), Dec. 2010, 22564-22569.

Liang et al., "Quantitative microarray analysis of intact glycolipid-CD1d interaction and correlation with cell-based cytokine production," J. Am. Chem. Soc., Sep. 17, 2008, 130(37):12348-12354.

Liang, P. H., Wang, S. K. & Wong, C.-H. Quantitative analysis of carbohydrate-protein interactions using glycan microarrays: Determination of surface and solution dissociation constants. J. Am. Chem. Soc. 129, 11177-11184, (2007).

Liang, Chi-Hui et al., Iron Oxide/Gold Core/Shell Nanoparticles for Ultrasensitive Detection of Carbohydrate-Protein Interactions, Anal. Chem. 2009; 81, 7750-7756.

Liao, Shih-Fen et al., Immunization of Fucose-Containing Polysaccharides From Reishi Mushroom Induces Antibodies to Tumor-Associated Globo H-Series Epitopes, Proceedings National Academy of Sciences PNAS, vol. 110, No. 34, Aug. 1, 2013, pp. 13809-13814.

Lin et al., A common glycan structure on immunoglobulin G for enhancement of effector functions, Proc. Natl. Acad. Sci,, Aug. 25, 2015, vol. 112, No. 34, p. 10611-10616.

Lindmark et al., "Binding of immunoglobulins to protein A and immunoglobulin levels in mammalian sera," J. Immunol. Meth., Aug. 12, 1983, 62(1): 1-13.

Liu C, et al., "Expansion of spleen myeloid suppressor cells represses NK cell cytotoxicity in tumor-bearing host" Blood. May 15, 2007;109(10):4336-42. Epub Jan. 23, 2007.

Liu et al., "Activity-based protein profiling: the serine hydrolases," Proc. Natl. Acad. Sci. USA, Dec. 21, 1999, 96(26): 14694-14699.

Liu et al., "Eradication of large colon tumor xenografts by targeted delivery of maytansinoids," Proc. Natl., Acad. Sci. U.S.A., Aug. 6, 1996, 93(16):8618-8623.

Liu et al., Enhanced anti-influenza agents conjugated with anti-inflammatory activity. J Med Chem. Oct. 11, 2012;55(19):8493-501.

Liu et al., Intramolecular ion-pair prodrugs of znamivir nad guanidino-oseltamivir. Bioorganic & Medicinal Chemistry. Jun. 2011; 19(16):4796-4802.

Liu et al., Synthesis and anti-influenza activities of carboxyl alkoxyalkyl esters of 4-guanidino-Neu5Ac2en (zanamivir). Bioorg Med Chem Lett. Sep. 1, 2007;17(17):4851-4. Epub Jun. 20, 2007.

LoBuglio et al., "Mouse/human chimeric monoclonal antibody in man: kinetics and immune response," Proc. Natl. Acad. Sci. U.S.A., Jun. 1989, 86(11):4220-4224.

Lode et al., "Targeted therapy with a novel enediyene antibiotic calicheamicin $\Theta^I_1$ effectively suppresses growth and dissemination of liver metastases in a syngeneic model of murine neuroblastoma," Cancer Res., Jul. 15, 1998, 58(14):2925-2928.

Lonberg et al., "Antigen-specific human antibodies from mice comprising four distinct genetic modifications," Nature, Apr. 28, 1994, 368(6474):856-859.

Lonberg et al., "Human antibodies from transgenic mice," Int. Rev. Immunol., 1995, 13(1):65-93.

Lopes, J.F. et al., Simulataneous Chromatographic Separation of Enantiomers, Anomers and Structural Isomers of Some Biologically Relevant Monsaccharides. J. Chomatogr. A, (2008) 1188:34-42.

Lou, et al., Stage-specific embryonic antigent-4 as a potential therapeutic target in glioblastoma multiforms and other cancers. Proc Natl Acad Sci USA 2014, 111(7):2482-7.

Loudet, A.; Burgess, K. "BODIPY dyes and their derivatives: syntheses and spectroscopic properties." Chem. Rev. 2007, 107, 4891-4932.

Louis et al., "The 2007 WHO classification of tumours of the central nervous system," Acta. Neuropathol., Aug. 2007, 114(2):97-109.

Lu et al., "Design of a mechanism-based probe for neuraminidase to capture influenza viruses," Angew. Chem. Int. Ed. Engl., Oct. 28, 2005, 44(42):6888-6892.

Lu, Guokai et al., Reactivity-Based One-Pot Synthesis of Immunosuppressive Glycolipids From the Caribbean Sponge Plakortis Simplex, Chinese J. Chem. 2009, 27, 2217-2222.

Lu et al., "Single chain anti-c-Met antibody conjugated nanoparticles for in vivo tumor-targeted imaging and drug delivery," Biomaterials, Apr. 2011, 32(12):3265-3274.

MacBeath, G. and Schreiber, S. L., Printing Proteins as Microarrays for High-Throughput Function Determination, Science, 289, 1760-1763, 2000.

MacDonald, Simon et al., Potent and Long-Acting Dimeric Inhibitors of Influenza Virus Neuraminidase Are Effective at a Once-Weekly Dosing Regimen, Antimicrobial Agents and Chemotherapy, 48(12), 4542-4549, Dec. 2004.

MacFarlane GT, et al., "Formation of glycoprotein degrading enzymes by Bacteroides fragilis" FEMS Microbiol Lett. Jan. 15, 1991;61 (2-3):289-93.

Makino et al., Predominant expression of invariant $V_\alpha 14^+$ TCR α chain in $NK1.1^+$ T cell populations, Int. Immunol., Jul. 1995, 7(7):1157-1161.

Mandler et al., "Immunoconjugates of geldanamycin and anti-HER2 monoclonal antibodies: antiproliferative activity on human breast carcinoma cell lines," J. Nat. Cancer Inst., Oct. 4, 2000, 92(19): 1573-1581.

Mandler et al., "Modifications in synthesis strategy improve the yield and efficacy of geldanamycin-herceptin immunoconjugates," Bioconjugate Chem., Jul.-Aug. 2002, 13(4):786-791.

Mandler et al., "Synthesis and evaluation of antiproliferative activity of a geldanamycin-Herceptin™ immunoconjugate," Bioorganic & Med. Chem. Letters, May 15, 2000, 10(10):1025-1028.

Mandal, M., Dudkin, V. Y., Geng, X. & Danishefsky, S. J. In pursuit of carbohydrate-based HIV vaccines, part I: The total synthesis of hybrid-type gp 120 fragments. Angew. Chem. Int. Ed. 43, 2557-2561, (2004).

Månsson et al., "Characterization of new gangliosides of the lactotetraose series in murine xenografts of a human glioma cell line," FEBS Lett., May 26, 1986, 201(1):109-113.

Marasco et al., "Design, intracellular expression, and activity of a human anti-human immunodeficiency virus type 1 gp120 single-chain antibody," Proc. Natl. Acad. Sci. U.S.A., Aug. 15, 1993, 90(16):7889-7893.

Marasco, "Intrabodies: turning the humoral immune system outside in for intracellular immunization," Gene Therapy, Jan. 1997, 4(1):11-15.

Marcato et al., "Chapter 17: The Rocky Road from Cancer Stem Cell Discovery to Diagnostic Applicability," Cancer Stem Cells Theories and Practice, pp. 335-360, Mar. 22, 2011.

Marks et al., "By-passing immunization. Human antibodies from V-gene libraries displayed on phage," J. Mol. Biol., Dec. 5, 1991, 222(3):581-597.

Marks et al., "By-passing immunization: Building high affinity human antibodies by chain shuffling," Nature Biotechnology, Jul. 1992, 10(7):779-783.

Massart, R., IEEE Transactions On Magnetics, 17, 1247 (1981).

(56) References Cited

OTHER PUBLICATIONS

Masuko, T. et al., Thiolation of Chitosan. Attachment of Proteins Via Thioether Formation, Biomacromolecules 2005, 6, 880-884.
Mather et al., "Culture of testicular cells in hormone-supplemented serum-free medium," Annals N.Y. Acad. Sci., 1982, 383:44-68.
Mather, "Establishment and characterization of two distinct mouse testicular epithelial cell lines," Biol. Reprod., Aug. 1980, 23(1):243-252.
Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.
Matsuda et al., "Structure and physical map of 64 variable segments in the 3' 0.8-megabase region of the human immunoglobulin heavy-chain locus," Nature Genet., Jan. 1993, 3(1):88-94.
Matz et al., "Fluorescent proteins from nonbioluminescent Anthozoa species," Nat. Biotechnol., Oct. 1999, 17(10):969-973.
McCafferty et al., "Phage antibodies: Filamentous phage displaying antibody variable domains," Nature, Dec. 6, 1990, 348:552-554.
McConville, Malcolm J., and M. A. Ferguson. "The structure, biosynthesis and function of glycosylated phosphatidylinositols in the parasitic protozoa and higher eukaryotes." Biochemical Journal 294.Pt 2 (1993): 305.
McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.
McKimm-Breschkin, "Resistance of influenza viruses to neuraminidase inhibitors—a review," Antiviral Res., Jul. 2000, 47(1): 1-17.
McKimm-Breschkin, J. et al., "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, 2264-2272.
Meezan et al., "Comparative studies on the carbohydrate-containing membrane components of normal and virus-transformed mouse fibroblasts: II: Separation of glycoproteins and glycopeptides by Sephadex chromatography," Biochemistry, Jun. 1969, 8(6):2518-2524.
Mendelson et al., NKp46 O-glycan Sequences that are involved in the interaction with Hemagglutinin Type 1 of Influenza Virus. J. Virol. Feb. 10, 2010, 84(8):3789-3797.
McLellan, J. S. et al. Structure of Hiv-I gp120 V1/V2 domain with broadly neutralizing antibody PG9. Nature 480, 336-343, 2011.
Merck, MAB4304, Anti-Stage-Specific Embryonic Antigen-4 Antibody, Clone MC-813-70, 4 Pages, found at http://www.emdmillipore.com/US/en/product/Anti-Stage-/specific-Embryonic-Antigen-4-Antibody-clone-MC-813-70,MM_NF-MAB4304, downloaded Jul. 26, 2017.
Meyer, "Malignant gliomas in adults," N. Engl. J. Med., Oct. 23, 2008, 359(17):1850.
Michaluart et al., "Inhibitory effects of caffeic acid phenethyl ester on the activity and expression of cyclooxygenase-2 in human oral epithelial cells and in a rat model of inflammation" Cancer Res. May 15, 1999;59(10):2347-2352.
Milstein, C & Cuello, AC, Hybrid Hydridomas and their use in immunohistochemistry, Nature 305, 537-540, Oct. 1983.
Mimura et al., "Role of oligosaccharide residues of IgG1-Fc in FcγRIIb binding," J. Biol. Chem., Dec. 7, 2001, 276(49):45539-45547.
Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," Cancer Res., Jul. 15, 2001, 61(14):5349-5354.
Miyagi et al., "Mammalian sialidases: Physiological and pathological roles in cellular functions," Glycobiology, Jul. 2012, 22(7):880-896.
Miyagi et al., "Plasma membrane-associated sialidase as a crucial regulator of transmembrane signalling," J. Biochem., Sep. 2008, 144(3):279-285.

Miyagi et al., "Sialidase and malignancy: a minireview," Glycoconj. J., 2004, 20(3):189-198.
Miyagi, "Aberrant expression of sialidase and cancer progression," Proc. Jpn. Acad. Ser. B. Phys. Biol. Sci., 2008(10), 84:407-418.
Miyaji, E. N. et al., Induction of Neutralizing Antibodies Against Diphtheria Toxin By Priming with Recombinant Mycobacterium Bovis BCG Expressing CRM 197, a Mutant Diphtheria Toxin, Infect. Immun. 2001, 69, 869.
Miyamoto et al., "A synthetic glycolipid prevents autoimmune encephalomyelitis by inducing $T_H2$ bias of natural killer T cells," Nature, Oct. 4, 2001, 413(6855):531-534.
Moal, E. Le et al., Enhanced Fluorescence Cell Imaging with Metal-Coated Slides, Biophysical Journal, vol. 92, 2150-2161, Mar. 2007.
Monti et al., "Sialidases in vertebrates: a family of enzymes tailored for several cell functions," Adv. Carbohydr. Chern. Biochem., 2010, 64:403-479.
Moody, M. D. et al., Array-based ELISAs for High-Throughput Analysis of Human/Cytokines. Biotechniques (2001), 31, 186-194.
Morelle, W. et al., "The Mass Spectrometric Analysis of Glycoproteins and their Glycan Structures", Review in Current Analytical Chemistry, vol. 1, No. 1 (2005), pp. 29-57.
Mori K, et al., "Non-fucosylated therapeutic antibodies: the next generation of therapeutic antibodies" Cytotechnology. Dec. 2007;55(2-3):109-14. Epub Oct. 31, 2007.
Morimoto et al., "Single-step purification of F(ab')2 fragments of mouse monoclonal antibodies (immunoglobulins G1) by hydrophobic interaction high performance liquid chromatography using TSKgel Phenyl-5PW," J. Biochem. Biophys. Meth., Mar. 1992, 24(1-2):107-117.
Morphy et al., Designed multiple ligands. An emerging drug discovery paradigm. J Med Chem. Oct. 20, 2005;48(21):6523-43.
Morphy et al., From magic bullets to designed multiple ligands. Drug Discov Today. Aug. 1, 2004;9(15):641-51.
Morrison et al., "Chimeric human antibody molecules: mouse antigen-binding domains with human constant region domains," Proc. Natl. Acad. Sci. U.S.A., Nov. 1984, 81(21):6851-6855.
Morrison, "Immunology. Success in specification," Nature, Apr. 28, 1994, 368(6474):812-813.
Moscona, "Global transmission of oseltamivir-resistant influenza," N Engl. J Med, Mar. 5, 2009, 360(10):953-956.
Moscona, Oseltamivir Resistance—Disabling Our Influenza Defenses, The New England Journal of Medicine, 2005, vol. 353, pp. 2633-2636.
Mosmann et al., "The expanding universe of T-cell subsets: Th1, Th2 and more," Immunol. Today, Mar. 1996, 17(3):138-146.
Mossong et al., "Emergence of oseltamivir-resistant influenza A H1N1 virus during the 2007-2008 winter season in Luxembourg: clinical characteristics and epidemiology," Antiviral Res., Oct. 2009, 84(1):91-94.
Mouquet, H. et al. Complex-type N-glycan recognition by potent broadly neutralizing HIV antibodies. Proc. Natl. Acad. Sci. U. S. A 109, E3268-E3277, (2012).
Munson et al., "Ligand: a versatile computerized approach for characterization of ligand-binding systems," Anal. Biochem., Sep. 1, 1980, 107(1):220-239.
Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).
Muthana, S., Yu, H., Huang, S., and Chen, X. Chemoenzymatic synthesis of size-defined polysaccharides by sialyltransferase-catalyzed block transfer of oligosaccharides. J. Am. Chern. Soc. 129, 11918-11919, (2007).
Natarajan et al., Caffeic acid phenethyl ester is a potent and specific inhibitor of activation of nuclear transcription factor NF-kappa B. Proc Natl Acad Sci USA Aug. 20, 1996;93(17):9090-5.
Neuberger et al., "Recombinant antibodies possessing novel effector functions," Nature, Dec. 13-19, 1984, 312(5995):604-608.
Neuberger, "Generating high-avidity human Mabs in mice," Nature Biotechnol., Jul. 1996, 14(7):826.

(56) References Cited

OTHER PUBLICATIONS

Ni, Jing et al., Immunoassay Readout Method Using Extrinsic Raman Labels Adsorbed on Immunogold Colloids, Anal. Chem., 1999, 71(21), pp. 4903-4908.
Nicolaou et al., "Calicheamicin $\Theta^I{}_1$: A rationally designed molecule with extremely potent and selective DNA cleaving properties and apoptosis inducing activity," Angew. Chem. Intl. Ed. Engl., Feb. 1, 1994, 33(2): 183-186.
Niculescu-Duvaz et al., "Antibody-directed enzyme prodrug therapy (ADEPT): A review," Adv. Drg. Del. Rev., Jul. 7, 1997, 26(2-3):151-172.
Nieuwenhuis et al., "CD1d-dependent macrophage-mediated clearance of *Pseudomonas aeruginosa* from lung," Nat. Med., Jun. 2002, 8(6):588-593.
Nielsen, U. B. et al., Multiplexed Sandwich Assays in Microarray Format, Journal Immunol. Meth. (2004), 290, 107-120.
Ning, X. et al., Visualizing Metabolically-Labeled Glycoconjugates of Living Cells By Copper-Free and Fast Huisgen Cycloadditions, J. Angew. Chem. Int. Ed. 2008, 47, 2253-2255.
Noto et al., "CD44 and SSEA-4 positive cells in an oral cancer cell line HSC-4 possess cancer stem-like cell characteristics," Oral Oncol., Aug. 2013, 49(8):787-795.
Nowak, MW et al., Nicotinic Receptor Binding Site Probed With Unnatural Amino Acid Incorporation in Intact Cells, Science 268:439, 1995.
Novotný et al., "Structural invariants of antigen binding: comparison of immunoglobulin $V_L$-$V_H$ and $V_L$-$V_L$ domain dimers," Proc. Natl. Acad. Sci. USA, Jul. 1985, 82(14):4592-4596.
Oberli, Matthias et al., A Possible Oligosaccharide-Conjugate Vaccine Candidate for Clostridium Difficile is Antigenic and Immunogenic, Chemistry & Biology, vol. 18, No. 5, May 2011, 580-588.
Ochiai et al. "Expeditious Chemoenzymatic Synthesis of Homogeneous N-Glycoproteins Carrying Defined Oligosaccharide Ligands" J. Am. Chem. Soc. 2008, vol. 130 No. 41, p. 13790-13803.
Office Action dated Dec. 3, 2013, from corresponding Chinese Patent Application No. 201180034218.3, 15 total pages.
Office Action dated Oct. 22, 2014, from corresponding Chinese Patent Application No. 201180034218.3, 16 total pages.
Office Action dated Aug. 29, 2017, from corresponding Japanese Patent Application No. 2016-169045, 5 total pages.
O'Garra, "Cytokines induce the development of functionally heterogeneous T helper cell subsets," Immunity, Mar. 1998, 8(3):275-283.
Okada, Yoshio et al. Changes in the Expression of Sialyl-Lewisx, a Hepatic Necroinflammation-Associated Carbohydrate Neoantigen, in Human Depatocellular Carcinomas, (1994) Cancer 73, 1811-1816.
Okamura et al., "Interleukin-18: a novel cytokine that augments both innate and acquired immunity," Adv. Immunol., 1998, 70:281-312.
Olden, Kenneth et al., Carbohydrate Moieties of Glycoproteins: A Re-Evaluation of Their Function, Biochem et Biophys Acta 650:209-232 (1982).
Orlandi et al., "Cloning immunoglobulin variable domains for expression by the polymerase chain reaction," Proc. Natl. Acad. Sci. U.S.A., May 1989, 86(10):3833-3837.
Ørum et al., "Efficient method for constructing comprehensive murine Fab antibody libraries displayed on phage." Nucleic Acids Res., Sep. 25, 1993, 21 (19):4491-4498.
Otsubo N, et al., Synthesis of sialyl Le$^x$ ganglioside analogues modified at C-6 of the galactose residue to elucidate the mechanism of selection recognition, Carbohydr. Res. 1998, 306, 517-530.
Ottolini et al., Combination anti-inflammatory and antiviral therapy of influenza in a cotton rat model. Pediatr. Pulmonol. 2003:36;290-4.
Oyelaran, 0. & Gildersleeve, J. C. Glycan arrays: recent advances and future challenges. Curr. Opin. Chem. Biol. 13, 406-413, (2009).
Pabst, M. et al., Glycan profiles of the 27 Nglycosylation sites of the HIV envelope protein CN54gp140. Biol. Chem. 393, 719-730, (2012).
Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.
Pan, Yanbin et al., Synthesis and Immunological Properties of N-Modified GM3 Antigens as Therapeutic Cancer Vaccines, J. Med. Chem., 48(3), 875-883, 2005.
Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).
Pancera, M. et al. Structural basis for diverse N-glycan recognition by HIV-I-neutralizing V1-V2-directed antibody PG16. Nat. Struct. Mol. Biol. 20, 804-813, (2013).
Papanastassiou et al., "The potential for efficacy of the modified (ICP 34.5$^-$) herpes simplex virus HSV1716 following intratumoural injection into human malignant glioma: a proof of principle study," Gene Therapy, Mar. 2002, 9(6):398-406.
Parker, C. A.; Rees, W. T., Correction of Fluorescence Spectra and Measurement of Fluorescence Quantum Efficiency, Analyst 1960, 85, 587-600.
Parrish, M. L. et al., A Microarray Platform Comparison for Neuroscience Applications, J. Neurosci. Methods, 2004, 132, 57-68.
Patricelli et al., "Functional interrogation of the kinome using nucleotide acyl phosphates," Biochemistry, Jan. 16, 2007, 46(2):350-358.
Paulson, J. C., Blixt, 0. & Collins, B. E. Sweet spots in functional glycomics. Nat. Chem. Biol. 2, 238-248, (2006).
Pearlman et al., *Peptide and Protein Drug Delivery, Chapter 6: Analysis of Protein Drugs*, Lee, ed., 1991, pp. 247-301, Marcel Dekker Publishing, New York.
Peelle et al., "Characterization and use of green fluorescent proteins from *Renilla mulleri* and *Ptilosarcus guernyi* for the human cell display of functional peptides," J. Protein Chem., Aug. 2001, 20(6):507-519.
Peipp et al., "Antibody fucosylation differentially impacts cytotoxicity mediated by NK and PMN effector cells," Blood, 2008, 112(6):2390-2399.
Peiris et al., Re-emergence of fatal human influenza A subtype H5N1disease. Lancet. Feb. 21, 2004;363(9409):617-9.
Pejchal, R. et al. A potent and broad neutralizing antibody recognizes and penetrates the HIV glycan shield. Science 334, 1097-1103, (2011).
Pellicci et al., "Differential recognition of CD1d-α-galactosyl ceramide by the Vβ8.2 and Vβ7 semi-invariant NKT T-cell receptors," Immunity, Jul. 17, 2009, 31(1):47-59.
Perlmutter, R.M. et al., Subclass Restriction of Murine Anti-Carbohydrate Antibodies, Journal of Immunology 1978, 121, 566-572.
Pettit, George et al., Antineoplastic Agents. Part 189. The Absolute Configuration and Synthesis of Natural (−)-Dolastatin 10, J Am Chem Soc. 111:5463-5465 (1989).
Pettit, George et al., "Dolastatins 24: synthesis of (−)-dolastatin 10. X-Ray molecular structure of N, N-dimethylvalyl-valyl-dolaisoleuine tert-butyl ester." J Chem Soc Perkin Trans. 15:859-863 (1996).
Pettit, George et al., Antineoplastic Agents 365. Dolastatin 10 SAR Probes, Anti-Cancer Drug Design 13:243-277 (1998).
Pettit, Robin et al., Specific Activities of Dolastatin 10 and Peptide Derivatives Against Cryptococcus Neoformans, Antimicrob Agents Chemother. 42:2961-2965 (1998).
Pettit, George et al., The Dolastatins; 18: Stereospecific Synthesis of Dolaproine, Synthesis, 719-725 (1996).
Piizi, G. and Hardinger, S., Stereochemistry: an Introduction, UCLA Chemistry 30A Presentation, Fall 2002, in 40 pages.
Plückthun, "Mono- and bivalent antibody fragments produced in *Escherichia coli*: Engineering, folding and antigen binding," Immunol. Rev., Dec. 1992, 130:151-188.
Plückthun, *Handbook of Experimental Pharmacology*, vol. 113: *The Pharacology of Monoclonal Antibodies, Chapter 11: Antibodies from Escherichia coli*, Rosenberg et al., eds., 1994, pp. 269-315, Springer-Verlag, Berlin.

(56) References Cited

OTHER PUBLICATIONS

Poloukhtine et al., "Selective labeling of living cells by a phototriggered click reaction," *J. Am. Chem. Soc.*, Nov. 4, 2009, 131(43): 15769-15776.
Porcelli, S.A., "Preparation of α-galactosylceramide derivatives as modulators of immunity and autoimmunity," CAPLUS 147:440317 (2007).
Potier et al., "Fluorometric assay of neuraminidase with a sodium (4-methylumbelliferyl-alpha-D-N-acetylneuraminate) substrate," Anal. Biochem., Apr. 15, 1979, 94(2):287-296.
Pratt, M. R. & Bertozzi, C. R. Chemoselective ligation applied to the synthesis of a biantennary N-linked glycoform of CD52. J Am. Chem. Soc. 125, 6149-6159, (2003).
Prescher, J. A.; Bertozzi, C.R. "Chemistry in living systems." Nat. Chem. Biol. 2005, 1, 13-21.
Presta et al., "Humanization of an antibody directed against IgE," *J. Immunol.*, Sep. 1, 1993, 151(5):2623-2632.
Presta et al., "Humanization of an anti-vascular endothelial growth factor monoclonal antibody for the therapy of solid tumors and other disorders," *Cancer Res.*, Oct. 15, 1997, 57(20):4593-4599.
Presta, "Antibody engineering," *Curr. Opin. Biotechnol.*, Aug. 1992, 2(4):394-398.
Presta, "Antibody engineering," *Curr. Opin. Struct. Biol.*, Aug. 1992, 2(4):593-596.
Pritchard, L. K. et al. Structural Constraints Determine the Glycosylation of HIV-I Envelope Trimers. Cell Rep. 11, 1604-13, (2015).
Pritchard, Laura et al., Cell- and Protein-Directed Glycosylation of Native Cleaved HIV-I Envelope. J. Virol. 89, 8932-44, (2015).
Proba et al., "Functional antibody single-chain fragments from the cytoplasm of *Escherichia coli*: influence of thioredoxin reductase (TrxB)," *Gene*, Jul. 4, 1995, 159(2):203-207.
Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosomal catabolism of keratan sulfate.
Puigbò P, Guzmán E, Romeu A, Garcia-Vallvé S. Optimizer: a web server for optimizing the codon usage of DNA sequences. *Nucleic Acids Res.* Jul. 2007;35(Web Server issue):W126-31. Epub Apr. 16, 2007.
Qi, Jianjun et al., Developing visible fluorogenic 'clickon' dyes for cellular imaging, Bioconjugate Chem. 2011, 22, 1758-1762.
Rabbani, Said et al., Glycosyltransferases: An efficient tool for the enzymatic synthesis of oligosaccharides and derivatives as well as mimetics thereof Chimia 60, 23-27, (2006).
Raju et al., "Synthesis and evaluation of 3"- and 4" -deoxy and -fluoro analogs of the immunostimulatory glycolipid, KRN7000," *Bioorg. Med. Chem. Lett.*, 2009, 19:4122-4125.
Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.
Rana, G. Kucukayan-Dogu, E. Bengu "Growth of vertically aligned carbon nanotubes over self-ordered nano-porous alumina films and their surface properties" Applied Surface Science, 2012, 258 7112-7117.
Raska, M. et al. Glycosylation patterns of HIV-I gp120 depend on the type of expressing cells and affect antibody recognition. J. Biol. Chem. 285, 20860-20869, (2010).
Ravetch et al., "Divergent roles for Fc receptors and complement in vivo," *Ann. Rev. Immunol.*, 1998, 16:421-432.
Ravetch et al., "Fc receptors," *Annu. Rev. Immunol.*, 1991, 9:457-492.
Reyes et al., "Expression of human β-interferon cDNA under the control of a thymidine kinase promoter from herpes simplex virus," *Nature*, Jun. 17, 1982, 297(5867):598-601.
Rtechmann et al., "Reshaping human antibodies for therapy," *Nature*, Mar. 24, 1988, 332(6162):323-327.
Rillahan, C. D. & Paulson, J. C. Glycan microarrays for decoding the glycome. Annu. Rev. Biochem. 80, 797-823, (2011).

Ritamo, Ilja al., Comparison of the Glycosylation of in Vitro Generated Polyclonal Human IgG and Therapeutic Immunoglins, Mol Immunol. Feb. 2014; 57(2): 255-62.
Rogers, GN et al., Single Amino Acid Substitutions in Influenza Haemagglutinin Change Receptor Binding Specificity. Nature, 304:76, 1983.
Rogers, GN et al., Receptor Determinants of Human and Animal Influenza Virus Isolates: Differences in Receptor Specificity of the H3 Hemagglutinin Based on Species of Origin. Virology, 127:361, 1983.
Roguska et al., "Humanization of murine monoclonal antibodies through variable domain resurfacing," *Proc. Natl. Acad. Sci. U.S.A.*, Feb. 1, 1994, 91(3):969-973.
Romagnani, "Induction of $T_H1$ and $T_H2$ responses: a key role for the 'natural' immune response?" *Immunol. Today*, Oct. 1992, 13(10):379-381.
Roos et al., "Specific inhibition of the classical complement pathway by C1q-binding peptides," *J. Immunol.*, Dec. 15, 2001, 167(12):7052-7059.
Rosenstein, N.E. et al., Meningococcal Disease, N Engl J Med 2001, 344, 1378-1388.
Rostovtsev et al., "A stepwise Huisgen cycloaddition process catalyzed by copper(I) regioselective ligation of azides and terminal alkynes," *Angew. Chem. Int. Ed. Engl.*, Jul. 15, 2002, 41(41):2596-2599.
Roth, Jurgen et al., Reexpression of Poly(sialic Acid) Units of the Neural Cell Adhesion Molecule in Wilms Tumor, Proc. Natl. Acad. Sci. 85, 2999-3000, 1988.
Rowland et al., "Drug localisation and growth inhibition studies of vindesine-monoclonal anti-CEA conjugates in a human tumour xenograft," *Cancer Immunol. Immunother.*, 1986, 21(3): 183-187.
Rudnick et al., Affinity and Avidity in Antibody-Based Tumor Targeting, Can Biotherp & Radoipharm, 24, 155-162 (2009).
Ruiz et al., "IMGT, the international ImMunoGeneTics database," *Nucl. Acids Res.*, Jan. 1, 2000, 28(1):219-221.
Russell et al., "The structure of H5N1 avian influenza neuraminidase suggests new opportunities for drug design," Nature, Sep. 7, 2006, 443(7107):45-49.
Saito, Seiichi et al., Haptoglobin-β Chain Defined By Monoclonal Antibody RM2 as a Novel Serum Marker for Prostate Cancer, Int. J Cancer, 2008, 123(3), 633-640.
Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Saitoh, Osamu et al., Differential Glycosylation and Cell Surface Expression of Lysosomal Membrane Glycoproteins in Sublines of a Human Colon Cancer Exhibiting Distinct Metastatic Potentials*, J. Biol. Chem. 267, 5700-5711, 1992.
Sakurama, Haruko et al., Differences in the Substrate Specificities and Active-Site Structures of Two a-L-Fucosidases (Glycoside Hydrolase Family 29) From Bacteroides Thetaiotaomicron, Bioscience Biotechnology Biochemistry, vol. 76, No. 5, May 23, 2012, pp. 1022-1024.
Salisbury et al., "Activity-based probes for proteomic profiling of histone deacetylase complexes," *Proc. Natl. Acad. Sci. USA*, Jan. 23, 2007, 104(4): 1171-1176.
Salomon et al., Inhibition of the cytokine response does not protect against lethal H5N1 nfluenza infection. Proc Natl Acad Sci U S A Jul. 24, 2007;104(30): 12479-81.
Sanna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).
Sarkar et al., "Disaccharide uptake and priming in animal cells: inhibition of sialyl Lewis X by acetylated Galβ1 →4GlcNAcβ-O-naphthalenemethanol," *Proc. Natl. Acad. Sci. USA*, Apr. 11, 1995, 92(8):3323-3327.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.

(56) References Cited

OTHER PUBLICATIONS

Sauter, NK et al., Binding of Influenza Virus Hemagglutinin to Analogs of Its Cell-Surface Receptor, Sialic Acid: Analysis By Proton Nuclear Magnetic Resonance Spectroscopy and X-Ray Crystallography. Biochemistry, 31 :9609, 1992.
Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." Proc. Nat. Acad. Sci. US.A., 2006, 103, 12371-12376.
Sawada, Tetsuji et al., E-Selectin Binding By Pancreatic Tumor Cells is Inhibited By Cancer Sera, Int. J. Cancer 57, 901-907, 1994.
Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.
Scanlan, C. N. et al., Exploiting the defensive sugars of HIV-I for drug and vaccine design. Nature 446, 1038-1045, (2007).
Schelhaas, Michael et al., Protecting Group Strategies in Organic Synthesis, Angew. Chem. Int. Ed. Engl. 1996, 35, 2056-2083.
Schena, M. et al., Quantitative Monitoring of Gene Expression Patterns with a Complementary DNA Microarray, Science, 1995, 270:467-70.
Schengrund et al., "Localization of sialidase in the plasma membrane of rat liver cells," J. Biol. Chem., May 10, 1972, 247(9):2742-2746.
Schenkel-Brunner, *Human Blood Groups, Chapter 8: P System*, 1995, p. 211-234, Springer-Verlag, Vienna.
Schier et al., "Identification of functional and structural amino-acid residues by parsimonious mutagenesis," Gene, Mar. 9, 1996, 169(2):147-155.
Schmitz, U. et al., Phage Display: A Molecular Tool For The Generation of Antibodies-A Review, Placenta, 21 Suppl. A:S 106 (2000).
Schneider, M.C. et al., Interactions Between Neisseria Meningitidis and the Complement System, Trends Microbial 2007, 15, 233-240.
Schroder et al., The Peptides, vol. 1, p. 76-136, 1965.
Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.
Schweitzer, Barry et al., Multiplexed Protein Profiling on Microarrays By Rolling-Circle Amplification, Nat. Biotechnol. (2002), 20, 359-365.
Scurr, D. J. et al. Surface characterization of carbohydrate microarrays. Langmuir 26, 17143- 17155, (2010).
Sell, "Cancer-associated carbohydrates identified by monoclonal antibodies," Hum. Pathol., Oct. 1990, 21(10): 1003-1019.
Serna, S et al., Construction of N-Glycan Microarrays by Using Modular Synthesis and On-Chip Nanoscale Enzymatic Glycosylation. Chem. Eur. J 16, 13163-13175, (2010).
Severi et al., "Sialic acid utilization by bacterial pathogens," Microbiology, Sep. 2007, 153(Pt 9):2817-2822.
Seyrantepe et al., "Neu4, a novel human lysosomal lumen sialidase, confers normal phenotype to sialidosis and galactosialidosis cells," J. Biol. Chem., Aug. 27, 2004, 279(35):37021-37029.
Shalaby et al., "Development of humanized bispecific antibodies reactive with cytotoxic lymphocytes and tumor cells overexpressing the HER2 protooncogene," J. Exp. Med., Jan. 1, 1992, 175(1):217-225.
Sheu et al., "Surveillance for neuraminidase inhibitor resistance among human influenza A and B viruses circulating worldwide from 2004 to 2008," Antimicrob. Agents Chemother., Sep. 2008, 52(9):3284-3292.
Shevinsky, LH et al., Monoclonal Antibody to Murine Embryos Defines a Stage-Specific Embryonic Antigen Expressed on Mouse Embryos and Human Teratocarinoma Cells., CELL vol. 30, Issue 3, Oct. 1982, pp. 697-705.
Shie, Jiun-Jie et al., "A concise and flexible synthesis of the potent anti-influenza agents tamiflu and tamiphosphor," Angew. Chem. Int. Ed Engl., 2008, 47(31):5788-5791.
Shie, Jiun-Jie et al., An Azido-BODIPY Probe for Glycosylation: Initiation of Strong Fluorescence Upon Triazole Formation, J. Am. Chem. Soc. 2014, 136, 9953-9961.
Shieh, Peyton et al., Fluorogenic Azidofluoresceins for Biological Imaging, J. Am. Chem. Soc. 2012, 134, 17428-17431.
Shields et al., "High resolution mapping of the binding site on human IgG1 for FcγRI, FcγRII, FcγRIII, and FcRn and design of IgG1 variants with improved binding to the FcγR," J. Biol. Chem., Mar. 2, 2001, 276(9):6591-6604.
Shields et al., "Lack of fucose on human IgG1 N-linked oligosaccharide improves binding to human FcγRIII antibody-dependent cellular toxicity," J. Biol. Chem., Jul. 26, 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J. Biol. Chem., Jan. 31, 2003, 278(5):3466-3473.
Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).
Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.
Shriver, Zachary et al., Glycomics: a Pathway to a Class of New and Improved Therapeutics, Nat Rev Drug Disc, 2004, 3, 863-873.
Sidhu et al., "Phage-displayed antibody libraries of synthetic heavy chain complementarity determining regions," J. Mol. Biol., Apr. 23, 2004, 338(2):299-310.
Siebenlist et al., "E. coli RNA polymerase interacts homologously with two different promoters," Cell, Jun. 1980, 20(2):269-281.
Sieber et al., "Proteomic profiling of metalloprotease activities with cocktails of active-site probes," Nat. Chem. Biol., May 2006, 2(5):274-281.
Simmons et al., "Expression of full-length immunoglobulins in *Escherichia coli*: Rapid and efficient production of aglycosylated antibodies," J. Immunol. Methods, May 1, 2002, 263(1-2): 133-147.
Sims et al., "A humanized CD18 antibody can block function without cell destruction," J. Immunol., Aug. 15, 1993, 151(4):2296-2308.
Sivakumar, Krishnamoorthy et al., "A fluorogenic 1,3-dipolar cycloaddition reaction of 3-azidocoumarins and acetylenes." Org. Lett. 2004,24, 4603-4606.
Skehel, John et al., Receptor Binding and Membrane Fusion in Virus Entry: The Influenza Hemagglutinin, Ann. Rev Biochem, 69:531, 2000.
Skerra, "Bacterial expression of immunoglobulin fragments," Curr. Opinion in Immunol., Apr. 1993, 5(2):256-262.
Slamon DJ, et al., Human breast cancer: correlation of relapse and survival with amplification of the HER-2/neu oncogene, Science. Jan. 9, 1987; 235(4785): 177-82.
Sletten et al., "Bioorthogonal Chemistry: Fishing for Selectivity in a Sea of Functionality," Angew. Che. Int. Ed. Engl., Aug. 27, 2009, 48(38):6974-6998.
Smith RA et al., "The active form of tumor necrosis factor is a trimer" J Biol Chem. May 25, 1987;262(15):6951-4.
Smyth MJ, et al., "CD4+CD25+ T regulatory cells suppress NK cell-mediated immunotherapy of cancer" J Immunol. Feb. 1, 2006;176(3): 1582-7.
Sok, Devin et al., Snapshot: Broadly Neutralizing Antibodies. Cell 155, 728-728, (2013).
Solomons, G. and Fryhle, C., Chapter 5 Titled, Stereochemistry: Chiral Molecules, p. 184-228, in "Organic Chemistry," 7th Edition, Wiley, Jun. 18, 2002.
Soriano del Amo, David et al. Chemoenzymatic synthesis of the sialyl Lewis X glycan and its derivatives. Carbohydr. Res. 345, 1107-13, (2010).
Spinosa, Maria Rita et al., The Neisseria Meningitidis Capsule is Important for Intracellular Survival in Huamn Cells, Infect Immun 2007, 75, 3594-3603.
Srinivasan, et al., Quantitative Biochemical Rationale for Differences in Transmissibility of 1918 Pandemic Influenza A Viruses, Proc. Natl. Acad. Sci., 105, 2800-2805, 2008.

(56) References Cited

OTHER PUBLICATIONS

Stein, K.E. et al., The Immune Response to an Isomaltohexosyl-Protein Conjugate, a Thymus-Dependent Analogue of Alpha(1 Replaced By 6) Dextran., J Immunol 1982, 128, 1350-1354.
Stein, K.E., Thymus-Independent and Thymus-Dependent Responses to Polysaccharide Antigens, J Infect Dis 1992, 165 Suppl 1, S49-52.
Stephens, David, Conquering the Meningococcus, FEMS Microbial Rev 2007, 31, 3-14.
Stephens, D.S. et al., Epidemic Meningitis, Meningococcaemia, and Neisseria Meningitidis, Lancet 2007, 369, 2196-2210.
Stephenson et al., "Neuraminidase inhibitor resistance after oseltamivir treatment of acute influenza A and B in children," Clin. Infect. Dis., Feb. 15, 2009, 48(4):389-396.
Stevanovic, Stefan, Identification of Tumour-Associated T-Cell Epitopes for Vaccine Development, Nat. Rev. Cancer, 2002, 2, 514-520.
Stevens, James et al., Structure of the Uncleaved Human H1 Hemagglutinin From the Extinct 1918 Influenza Virus, Science, 303:1866, 2004.
Stevens, James et al., Structure and Receptor Specificity of the Hemagglutinin From an H5N1 Influenza Virus, Science, 312:404, 2006.
Stevens et al., Glycan Microarry Analysis of the Hemagglutinins From Modern and Pandemic Influenza Viruses Reveals Different Receptor Specificities. Journal of Molecular Biology 355.5 (2006): 1143-1155.
Stickings, Paul et al., Transcutaneous Immunization with Cross-Reacting Material CRM197 of Diphtheria Toxin Boosts Functional Antibody Levels in Mice Primed Parenterally with Adsorbed Diphtheria Toxoid Vaccine, Infection and Immunity, 2008,. 76, 1766-1773.
Stockmann, H. et al., Development and Evaluation of New Cyclootynes for Cell Surface Glycan Imaging in Cancer Cells, Chem. Sci. 2011, 2, 932-936.
Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.
Stubbs et al., "Synthesis and use of mechanism-based protein-profiling probes for retaining β-D-glucosaminidases facilitate identification of *Pseudomonas aeruginosa* NagZ," *J. Am. Chem. Soc.*, Jan. 9, 2008, 130(1):327-335.
Su, G. Hahner, W. Zhou "Investigation of the pore formation in anodic aluminum oxide" J Mater. Chem. 2008, 18 5787-5795.
Sun, B., Srinibasan, B., Huang, X., Pre-activation-based one-pot synthesis of an alpha-(2,3)-sialylated core-fucosylated complex type bi-antennary N-glycan dodecasaccharide. Chem. Eur. J 14 (23), 7072-81, (2008).
Supplementary European Search Report in European Application No. EP 13775664.9, dated Oct. 27, 2015, in 7 pages.
Suresh et al., "Bispecific monoclonal antibodies from hybrid hybridomas," *Methods in Enzymology*, 1986, 121:210-228.
Sutton, VR et al., Bcl-2 Prevents Apoptosis Induced by Perforin and Granzyme B, But Not That Mediated by Whole Cytotoxic Lymphocytes, J of Immunology 1997,. 158(12), 5783.
Suzuki E, et al., "A nonfucosylated anti-HER2 antibody augments antibody-dependent cellular cytotoxicity in breast cancer patients" *Clin Cancer Res.* Mar. 15, 2007;13(6):1875-82.
Svennerholm et al., "Human brain gangliosides: Developmental changes from early fetal stage to advanced age," *Biochim. Biophys. Acta*, Sep. 25, 1989, 1005(2):109-117.
Syrigos et al., "Antibody directed enzyme prodrug therapy (ADEPT): a review of the experimental and clinical considerations," *Anticancer Research*, Jan.-Feb. 1999, 19(1A):605-614.
Tahir et al., "Loss of IFN-γ production by invariant NK T cells in advanced cancer," *J. Immunol.*, Oct. 1, 2001, 167(7):4046-4050.
Takakura, Yoshimitsu et al., Molecular cloning, expression and properties of an alpha/beta-Galactoside alpha 2,3-sialyltransferase from Vibrio sp. JT- FAJ-16. J. Biochem. 142, 403-412, (2007) .

Takano, Ryo et al., Sialylation and Malignant Potential in Tumour Cell Glycosylation Mutants, Glycobiology 4, 665-674 (1994).
Takeda et al., "Construction of chimaeric processed immunoglobulin genes containing mouse variable and human constant region sequences," Nature, Apr. 4-10, 1985, 314(6010):452-454.
Taki, Takao et al., Glycolipids of Metastatic Tissue in Liver From Colon Cancer: Appearance of Sialylated Lex and Lex Lipids, J. Biochem. 103, 998-1003, 1988.
Talmadge et al., Murine models to evaluate novel and conventional therapeutic strategies for cancer, Am. J. Pathol, 170(3): 793-804 (2007).
Tanaka, Hiroshi et al., An Efficient Convergent Synthesis of GP1c Ganglioside Epitope, J Am Chern Soc. 2008, 130, 17244.
Tanaka, Katsunori et al., Synthesis of a Sialic Acid Containing Complex-Type N-Glycan on a Solid Support, Chemistry—an Asian Journal, 2009, vol. 4 (4), p. 574-580.
Taton, T. Andrew et al., Scanometric DNA Array Detection with Nanoparticle Probes, Science 289 (2000) 1757-1760.
Taton, T. Andrew et al., Two-Color Labeling of Oligonucleotide Arrays Via Size-Selective Scattering of Nanoparticle Probes, J. Am. Chem. Soc. (2001), 123, 5164-5165.
Taylor-Papadimitriou et al., "Exploiting altered glycosylation patterns in cancer: Progress and challenges in diagnosis and therapy," *Trends Biotechnol.*, Jun. 1994, 12(6):227-233.
Tebbey et al. "Importance of manufacturing consistency of the glycosylated monoclonal antibody adalimumab (Humira®) and potential impact on the clinical use of biosimilars" GABI Journal 2016, vol. 5 Issue 2, pp. 70-73.
Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).
"The Human Protein Atlas", B3GALT5 URL:http://www.proteinatlas.org/ENSG00000183778-B3GALT5/cancer, Sep. 9, 2015, downloaded Aug. 4, 2017.
Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.
Thurber, Greg et al., Antibody Tumor Penetration: Transport Opposed By Systemic and Antigen-Mediated Clearance, Adv Drug Deliv Rev, 60: 1421-1434, 2008.
Toba, et al., "Synthesis and biological evaluation of truncated α-glaactosylceramide derivatives focusing on cytokine induction profile," Bioorganic & Medicinal Chemistry 20(2012): 2850-2859.
Tomlinson et al., "The repertoire of human germline $V_H$ sequences reveals about fifty groups of $V_H$ segments with different hypervariable loops," *J. Mol. Biol.*, Oct. 5, 1992, 227(3):776-798.
Torres-Sanchez et al., "Synthesis and Biological Evaluation of Phophono Analogues of Capsular Polysaccharide Fragments From Neisseria Meningtitidis A" Chem Eur J (2007) vol. 13, pp. 6623-6635.
Toshima, K. Glycosyl fluorides in glycosidations. Carbohydr. Res. 327, 15-26 (2000).
Traunecker et al., "Bispecific single chain molecules (Janusins) target cytotoxic lymphocytes on HIV infected cells," *EMBO J.*, Dec. 1991, 10(12):3655-3659.
Traylor et al., "Gangliosides of human cerebral astrocytomas," *J. Neurochem.*, Jan. 1980, 34(1):126-131.
Trinchieri et al., "Interleukin-12: a proinflammatory cytokine with immunoregulatory functions that bridge innate resistance and antigen-specific adaptive immunity," *Annu. Rev. Immunol.*, 1995, 13:251-276.
Tsai et al., "Design and synthesis of activity probes for glycosidases," *Org. Lett.*, Oct. 17, 2002, 4(21):3607-3610.
Tsai, Charng-sheng et al., Development of Trifunctional Probes for Glycoproteomic Analysis, Chem. Commun. 2010, 46, 5575-5577.
Tsai TI, et al., "Effective sugar nucleotide regeneration for the large-scale enzymatic synthesis of Globo H and SSEA4" *J Am Chem Soc.* Oct. 2, 2013;135(39): 14831-9, Epub Sep. 17, 2013.
Tsai, Charng-Sheng et al., Cell-Permeable Probe for Identification and Imaging of Sialidases, PNAS, vol. 110, No. 7, 2013, 2466-2471.
Tsai, Tsung-I et al., An Effective Bacterial Ducosidase For Glycoprotein Remodeling, ACS Chemical Biology, vol. 12, No. 1, Jan. 20, 2017, pp. 63-72.

(56) References Cited

OTHER PUBLICATIONS

Tseng, Susan Y. et al., Glycan Arrays on Aluminum Coated Glass Slides. Chem. Asian J, 2008, 3, 1395-1405.
Tsuji, et al., "Preparation of glycolipids and analogs as antigens for NKT cells for use in vaccines and immunotherapy," CAPLUS 149:492050 (2008).
Tsukamoto, Hiroshi et al., *Photobacterium* sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.
Tumpey, Terrence et al., Characterization of the Reconstructed 1918 Spanish Influenza Pandemic Virus, Science, 310:77, 2005.
Tutt et al., "Trispecific F(ab')$_3$ derivatives that use cooperative signaling via the TCR/CD3 complex and CD2 to activate and redirect resting cytotoxic T cells," *J. Immunol.*, Jul. 1, 1991, 147(1):60-69.
Tyagarajan K et al., "Exoglycosidase purity and linkage specificity: assessment using oligosaccharide substrates and high-pH anion-exchange chromatography with pulsed amperometric detection" *Glycobiology.* Jan. 1996;6(1):83-93.
Tzeng, Y. L. et al., Epidemiology and Pathogenesis of Neisseria Meningitidis, Microbes Infect 2000, 2, 687-700.
Uchida, Tsuyoshi et al., Diphtheria Toxin and Related Proteins, J Biol. Chem. 218; 3838-3844 (1973).
Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.
Ulevitch, RJ et al., Receptor-Dependent Mechanisms of Cell Stimulation By Bacterial Endotoxin, 1995, Annu. Rev. Immunol., 13: 437.
Ulrich, G.; Ziessel, R.; Harriman, A. "The chemistry of fluorescent bodipy dyes: Versatility unsurpassed." Angew. Chem. Int. Ed. 2008, 47, 1184-1201.
Unverzagt, Carlo et al., A Double Regio- and Stereoselective Glycosylation Strategy for the Synthesis of N-Glycans, Chem. Eur. J., 2008, 14, 1304-1311.
Urlaub et al., "Isolation of Chinese hamster cell mutants deficient in dihydrofolate reductase activity." Proc. Natl. Acad. Sci. U.S.A., Jul. 1980, 77(7):4216-4220.
Valentine MA, et al., "Phosphorylation of the CD20 phosphoprotein in resting B lymphocytes. Regulation by protein kinase C" *J Biol Chem.* Jul. 5, 1989;264(19):11282-7.
Van Beek et al., "Increased sialic acid density in surface glycoprotein of transformed and malignant cells—a general phenomenon?" *Cancer Res.*, Nov. 1973, 33(11):2913-2922.
Van der Horst et al., "Photoaffinity labeling of a bacterial sialidase with an aryl azide derivative of sialic acid," *J. Biol. Chem.*, Jul. 5, 1990, 265(19), 10801-10804.
Van Hest, Jan C.M. et al., Efficient Introduction of Alkene Functionality Into Proteins in Vivo (1998) FEES Lett. 428:68.
Varki, Ajit et al., Symbol Nomenclature for Glycan Representation, Proteomics. Dec. 2009, 9(24): 5398-5399.
Van Meir et al., "Exciting new advances in neuro-oncology: the avenue to a cure for malignant glioma," *CA Cancer J. Clin.*, May-Jun. 2010, 60(3): 166-193.
Van Slambrouck et al., "Clustering of monosialyl-Gb5 initiates downstream signalling events leading to invasion of MCF-7 breast cancer cells," *Biochem. J.*, Feb. 1, 2007, 401(3):689-699.
Varghese et al., Three-dimensional structure of the complex of 4-guanidino-Neu5Ac2en and nfluenza virus neuraminidase. Protein Sci. Jun. 1995;4(6):1081-7.
Varki, "Glycan-based interactions involving vertebrate sialic-acid-recognizing proteins," *Nature*, Apr. 26, 2007, 446(7139):1023-1029.
Vasella et al., "Synthesis of a phosphonic acid analogue of N-Acetyl-2,3-didehydro-2-deoxyneuraminic acid, an inhibitor of Vibrio cholerae sialidase," Helv. Chim. Acta, Mar. 13, 1991, 74(2):451-463.
Vaswani et al., "Humanized antibodies as potential therapeutic drugs," *Ann. Allergy, Asthma Immunol.*, Aug. 1998, 81(2): 105-116, 119.

Vavricka, Christopher et al., Influenza Neuraminidase Operates Via a Nucleophilic Mechanism and Can Be Targeted By Covalent Inhibitors, Nature Communcations, 4:1491 (2013).
Verhoeyen et al., "Reshaping human antibodies: grafting an antilysozyme activity," *Science*, Mar. 25, 1988, 239(4847):1534-1536.
Vermeer AW et al., "The thermal stability of immunoglobulin: unfolding and aggregation of a multi-domain protein" *Biophys J.* Jan. 2000;78(1):394-404.
Vinogradova et al., "Molecular mechanism of lysosomal sialidase deficiency in galactosialidosis involves its rapid degradation," *Biochem. J.*, Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbiol 2009, 7, 274-286.
Vitetta, ES et al., Redesigning Nature's Poisons to Create Anti-Tumor Reagents, Science 23(8): 1098 (1987).
Vocadlo et al., "A strategy for functional proteomic analysis of glycosidase activity from cell lysates," *Angew. Chem. Int. Ed. Engl.*, Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).
Wada et al., "A crucial role of plasma membrane-associated sialidase in the survival of human cancer cells," *Oncogene*, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases," *Methods Mol. Biol.*, 2009, 519:417-429.
Walker, L. M. et al. Broad neutralization coverage of HIV by multiple highly potent antibodies. Nature 477, 466-470, (2011).
Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.
Wang, Zhen et al., Multi-Component One-Pot Synthesis of the Tumor-Associated Carbohydrate Antigen Globo-H Based on Preactivation of Thioglycosyl Donors, J Org. Chem. 2007, 72, 6409.
Wang et al., "Glycan microarray of Globo H and related structures for quantitative analysis of breast cancer," *Proc. Natl. Acad. Sci. U.S.A.*, Aug. 19, 2008, 105(33):11661-11666.
Wang et al., "A continuous colorimetric assay for rhinovirus-14 3C protease using peptide p-nitroanilides as substrates," Anal. Biochem., Oct. 15, 1997, 252(2):238-245.
Wang et al., "Synthesis of Neisseria Meningitidis Serogroup W135 Capsular Oligosaccharides for Immunogenicity Comparison and Vaccine Development" Angew Chem Int Ed (2013) vol. 52, pp. 9157-9161.
Wang, Michael et al., "Mechanism by which mutations at his274 alter sensitivity of influenza A virus NI neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, a. Carbohydrate microarrays for the recognition of cross-reactive molecular markers of microbes and host cells. Nat. Biotechnol . 20, 275-281, (2002).
Wang et al., Computational Studies of H5N1 Influenza Virus Resistance to Oseltamivir. Protein Sci. 2009, 18(4): 707-715; p. 713.
Wang, C. C. et al. Glycans on Influenza Hemagglutinin Affect Receptor Binding and Immune Response, Proc. Natl. Acad. Sci. 2009, 106, 18137-18142.
Wang, L. X. Carbohydrate-based vaccines against HIV/AIDS. Acs Sym. Ser. 932, 133-160 (2006).
Wang, L. X. Synthetic carbohydrate antigens for HIV vaccine design. Curr. Opin. Chem. Biol. 17, 997-1005, (2013).
Wang, W. et al. A systematic study of the N-glycosylation sites of HIV-I envelope protein on infectivity and antibody-mediated neutralization. Retrovirology, 10, 14, (2013).

(56) References Cited

OTHER PUBLICATIONS

Wang, Zhen et al. A general strategy for the chemoenzymatic synthesis of asymmetrically branched N-glycans. Science 341, 379-383, (2013).
Ward et al., "Binding activities of a repertoire of single immunoglobulin variable domains secreted from *Escherichia coli,*" Nature, Oct. 12, 1989, 341(6242):544-546.
Waterhouse et al., "Combinatorial infection and in vivo recombination: a strategy for making large phage antibody repertoires," *Nuc. Acids Res.*, May 11, 1993, 21(9):2265-2266.
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "*Trypanosoma cruzi* trans-sialidase operates through a covalent sialyl-enzyme intermediate: tyrosine is the catalytic nucleophile," *J. Am. Chem. Soc.*, Jun. 25, 2003, 125(25):7532-7533.
Waibel, Robert et al., Tumor-Associated Membrane Sialoglycoprotein on Human Small Cell Lung Carcinoma Identified By The IgG2a Monoclonal Antibody SWA20, (1988) Cancer Res. 48, 4318-4323.
Wen, Wen Hsien et al., "Synergistic effect of zanamivir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wikstrand et al., "Monoclonal antibody therapy of human gliomas: Current status and future approaches," *Cancer Metastasis Rev.*, 1999, 18(4):451-464.
Wilen et al., "Strategies in optical resolutions," Tetrahedron, 1977, 33(21):2725-2736.
Williams et al., "Cloning and sequencing of human immunoglobulin V lambda gene segments." *Eur. J. Immunol.*, Jul. 1993, 23(7):1456-1461.
Wiltshire, S. et al. "Immunoassays with rolling circle DNA amplification: a versatile platform for ultrasensitive antigen detection," Proc. Natl. Acad. Sci. (2000) 97, 10113-10119.
Winter et al., "Making antibodies by phage display technology," *Annu. Rev. Immunol.*, 1994, 12:433-455.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).
Wiseman, Gregory et al., Ibritumomab Tiuxetan Radioimmunotherapy for Patients with Relapsed or Refractory Non-Hodgkin Lymphoma and Mild Thrombocytopenia: a Phase II Multicenter Trial, Blood 99(12): 4336-42 (2002).
Wiseman, Gregory A., et al. "Radiation dosimetry results and safety correlations from (90) Y-ibritumomab tiuxetan radioimmunotherapy for relapsed or refractory non-Hodgkin's lymphoma: Combined data from 4 clinical trials" The Journal of Nuclear Medicine 44.3 (2003): 465-474.
Witte et al., "Ultrasensitive in situ visualization of active glucocerebrosidase molecules," *Nat. Chem. Biol.*, Dec. 2010, 6(12):907-913.
Witzig, Thomas et al., Randomized Controlled Trial of Yttrium-90-Labeled Ibritumomab Tiuxetan Radioimmunotherpay Versus Rituximab Immunotherapy for Patients with Relapsed or Refractory Low-Grade, Follicular, or Transformed B-Cell Non-Hodgkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Wong et al., α-Galactosyl Ceramide Analogs and Their use as Therapeutic, CAPLUS 152:166997, 2010, 2 Pages.
Woo et al. Cytokine profiles induced by the novel swine-origin influenza A/H1N1 virus: Implications for treatment strategies. J Infect Dis. Feb. 1, 2010;201(3):346-53.

Woof et al., "Human antibody-Fc receptor interactions illuminated by crystal structures," *Nat. Rev. Immunol.*, Feb. 2004, 4(2):89-99.
Woyke, Tanja et al., Effect of Auristatin PHE on Microtubule Integrity and Nuclear Localization in Cryptococcus Neoformans, Antimicrob. Agents and Chemother. 45(12): 3580-3584 (2002).
Wright et al. Antibody variable region glycosylation: biochemical and clinical effects, Springer Semin Immunopathology, 15:259-273 (1993).
Wu et al., "Avidity of CD1d-ligand-receptor ternary complex contributes to T-helper 1 (Th1) polarization and anticancer efficacy," *Proc. Natl. Acad. Sci. USA*, Oct. 18, 2011, 108(42): 17275-17280.
Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.
Wu et al., "Catalytic azide-alkyne cycloaddition: reactivity and applications," Aldrichimica Acta, 2007, 40(1):7-17.
Xie, F.; Sivakumar, K.; Zeng, Q. B.; Bruckman, M. A.; Hodges, B.; Wang, Q. "A fluorogenic 'click' reaction of azidoanthracene derivatives." Tetrahedron 2008, 64, 2906-2914.
Yamaguchi, Kazunori et al., "Evidence for mitochondrial localization of a novel human sialidase (NEU4)," *Biochem. J.*, Aug. 15, 2005, 390(Pt 1):85-93.
Yamane-Ohnuki, Naoko et al., Production of Therapeutic Antibodies with Controlled Fucosylation, mAbs 2009, 1;3:230-236.
Yamashita et al., CS-8958, a prodrug of the new neuraminidase inhibitor R-125489, shows ong-acting anti-influenza virus activity. Antimicrob Agents Chemother. Jan. 2009;53(1): 186-92.
Yamashita, Yoshito et al., Alterations in Gastric Mucin with Malignant Transformation: Novel Pathway for Mucin Synthesis, (1995) J. Natl. Cancer Inst. 87, 441-446.
Yang, JM et al., Alterations of O-Glycan Biosynthesis in Human Colon Cancer Tissues, (1994) Glycobiology 4, 873-884.
Yaniv, "Enhancing elements for activation of eukaryotic promoters." Nature 297: 17-18, 1982.
Yansura et al., "Nucleotide sequence selection for increased expression of heterologous genes in *Escherichia coli,*" Methods: A Companion to Methods in Enzymol., Aug. 1992, 4(2): 151-158.
Yates AJ et al., Brain Tumors in Childhood. Childs Brain 5(1), 31-39 (1979).
Ye et al., "Stage-specific embryonic antigen 4 expression in epithelial ovarian carcinoma," *Int. J. Gynecol. Cancer*, Aug. 2010, 20(6):958-964.
Yelton et al., "Affinity maturation of the BR96 anti-carcinoma antibody by codon-based mutagenesis." *J. Immunol.*, Aug. 15, 1995, 155(4):1994-2004.
Yguerabide, Juan et al., Light-Scattering Submicroscopic Particles as Highly Fluorescent Analogs and Their Use as Tracer Labels in Clinical and Biological Applications: II. Experimental Characterization, Anal. Biochem. (1998), 262, 157-176.
Ying et al., One-bead-one-inhibitor-one-substrate screening of neuraminidase activity. Chembiochem. Oct. 2005;6(10):1857-65.
Yoshida M, et al. "Synthesis of chemically modified sialic acid-containing sialyl-Le X ganglioside analogues recognized by the selectin family." Glycoconjugate J. 1993, 10, 3-15.
Yoshimoto et al., "$CD4^{Pos}$, $NK1.1^{Pos}$ T cells promptly produce interleukin 4 in response to in vivo challenge with anti-CD3," *J. Exp. Med.*, Apr. 1, 1994, 179(4): 1285-1295.
Yu et al., "Anti-GD2 antibody with GM-CSF, interleukin-2, and isotretinoin for neuroblastoma," *N. Engl. J. Med.*, Sep. 30, 2010, 363(14):1324-1334.
Yuen et al., Human infection by avian influenza A H5N1. Hong Kong Med J. Jun. 2005;1 1(3):189-99.
Zapata et al., "Engineering linear F(ab')$_2$ fragments for efficient production in *Escherichia coli* and enhanced antiproliferative activity," *Protein Eng.*, Oct. 1995, 8(10):1057-1062.
Zarei et al., "Separation and identification of GM1b pathway Neu5Ac- and Neu5Gc gangliosides by on-line nanoHPLC-QToF MS and tandem MS: toward glycolipidomics screening of animal cell lines," *Glycobiology*, Jan. 2010, 20(1):118-126.

(56) References Cited

OTHER PUBLICATIONS

Zhang et al., "New cerebrosides from Acanthopanax gracilistylus," CAPLUS 156:225776 (2011).
Zhang, Hai-Long et al., A Novel Combined Conjugate Vaccine: Enhanced Immunogenicity of bFGF with CRM197 as a Carrier Protein, Molecular Medicine Reports, 4, 857-863, 2011.
Zhang et al., "Selection of tumor antigens as targets for immune attack using immunohistochemistry: I. Focus on gangliosides," *Int. J. Cancer*, Sep. 26, 1997, 73(1):42-49.
Zheng et al., Delayed antiviral plus immunomodular treatment still reduces mortality in mice infected by high inoculum of influenza A/H5N1 virus. Proc Natl Acad Sci U S A. Jun. 10, 2008; 105(23):8091-6.
Zhang et al. "Glycoengineered Pichia produced anti-HER2 is comparable to trastuzumab in preclinical study" mAbs May-Jun. 2011, vol. 3 No. 3, pp. 289-298.
Zhou et al., A fluorogenic probe for the copper(I)-catalyzed azide-alkyne ligation reaction: modulation of the fluorescence emission via $^3(n,\pi^*)$-$^1(\pi,\pi^*)$ inversion, *J. Am. Chem. Soc.*, Jul. 28, 2004, 126(29):8862-8863.
Zhu, X et al., Mass spectrometric characterization of the glycosylation pattern of HIV-gp120 expressed in CHO cells. Biochemistry 39, 11194-11204 (2000).
Zou, et al., Chemoenzymatic synthesis and Fc gamma receptor binding of homogenous glycoforms of antibody Fc to FcIIIa receptor. J Am Chem Soc. 2011, 133(46): 18975-91.
Zimmermann et al., Multi-target therapeutics: when the whole is greater than the sum of the parts. Drug Discov Today. Jan. 2007;12(1-2):34-42. Epub Nov. 28, 2006.
Hodoniczky J, Zheng YZ, James DC. "Control of recombinant monoclonal antibody effector functions by Fc N-glycan remodeling in vitro" Biotechnology Progress. 2005;21(6):1644-1652.
Komarova TV, et al. "Trastuzumab and pertuzumab plant biosimilars: Modification of Asn297-linked glycan of the mAbs produced in a plant with fucosyltransferase and xylosyltransferase gene knockouts" Biochemistry (Moscow). Apr. 1, 2017 ;82(4):510-520.
Liu L. "Antibody glycosylation and its impact on the pharmacokinetics and pharmacodynamics of monoclonal antibodies and Fc-fusion proteins" Journal of Pharmaceutical Sciences. Jun. 2015;104(6):1866-1884.
Raju TS. "Terminal sugars of Fc glycans influence antibody effector functions of IgGs" Current Opinion in Immunology. Aug. 1, 2008;20(4):471-478.
Zhou Q, et al. "Site-specific antibody-drug conjugation through glycoengineering" Bioconjugate Chemistry. Feb. 28, 2014;25(3):510-520.
U.S. Appl. No. 16/502,844, filed Jul. 3, 2019, Chi-Huey Wong.
Hsieh, M-H et al., "Synthesis and Evaluation of Acyl-Chain- and Galactose-6"-Modified Analogues of α-GalCer for NKT Cell Activation", ChemBioChem, 2012, vol. 13, No. 11, pp. 1689-1697.
Shao et al., "The effect of the protein matrix proximity on glycan reactivity in a glycoprotein model," Eur J. Biochem., 228:79-85 (1995).
Bello et al., Hematology 2007: 2007(1):233-242.
Berg, Jan-Olof et al., "Purification of Glycoside Hydrolases from Bacteroides fragilis," Applied and Environmental Microbiology, Jul. 1980, vol. 40, No. 1, pp. 40-47.
Database EMBL [Online] Mar. 3, 2005 (Mar. 3, 2005), "Bacteroides fragilis NCTC 9343 putative exported alpha-L-fucosidase protein", retrieved from EBI accession No. EMBL:CAH08937; XP-002775523.
Database EMBL [Online] Jan. 6, 2006 (Jan. 6, 2006). "Bacteroides thetaiotaomicron VPI-5482 alpha-L-fucosidase precursor", retrieved from EBI accession No. EMBL:AA076949; XP-002775522.
European Search Report dated Oct. 1, 2021, under EP Application No. 21162500.9.
Huang, Wei et al., "Chemoenzymatic Glycoengineering of Intact IgG Antibodies of Gain of Functions," JACS, 2012, vol. 134, pp. 12308-12318.
Liao, Shih-Fen et al., "Immunization of fucose-containing polysaccharides from Reishi mushroom Induces antibodies to tumor-associated Globo H-series epitopes". Proceedings National Academy of Sciences PNAS, vol. 110, No. 34, Aug. 1, 2013 (Aug. 1, 2013), pp. 13809-13814.
Lloyd e al., Protein Engineering, Design & Selection 2009, 22: 159-168.
Sakurama, Haruko et al., "Differences in the Substrate Specificities and Active-Site Structures of Two [alpha]-L—Fucosidases (Glycoside Hydrolase Family 29) from Bacteroides thetaiotaomicron". Bioscience Biotechnology Biochemistry, vol. 76, No. 5, May 23, 2012 (May 23, 2012), pp. 1022-1024.
Schroeder et al., J Allergy Clin Immunol 2010, 125: S41-S52.
Shivatare, Sachin S. et al., "Modular synthesis of N/glycans and arrays for the hetero-ligand binding analysis of HIV antibodies," Nat Chem., Apr. 2016, 8(4):338-346.
Tsai, Tsung-I et al., "An Effective Bacterial Fucosidase for Glycoprotein Remodeling," ACS Chemical Biology, 2017, vol. 12, pp. 63-72.

\* cited by examiner

FIG. 5A  HUMIRA® (Adalimumab) from CHO cells
FIG. 5B
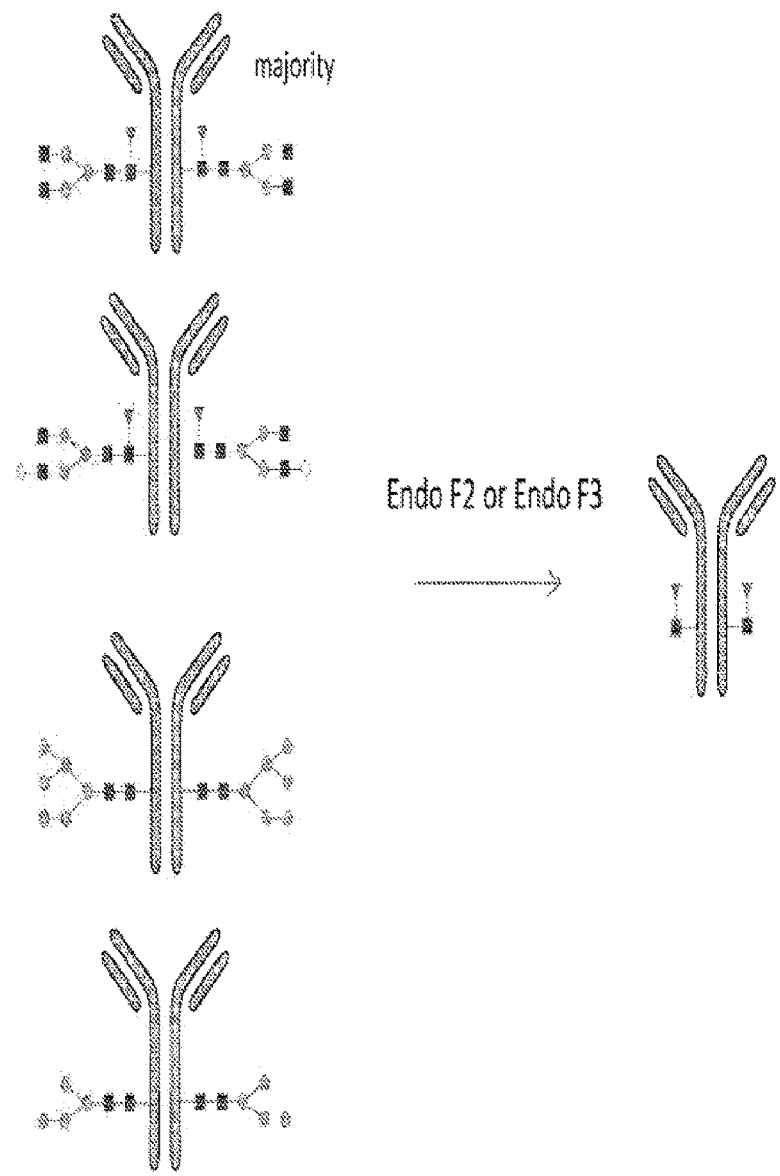
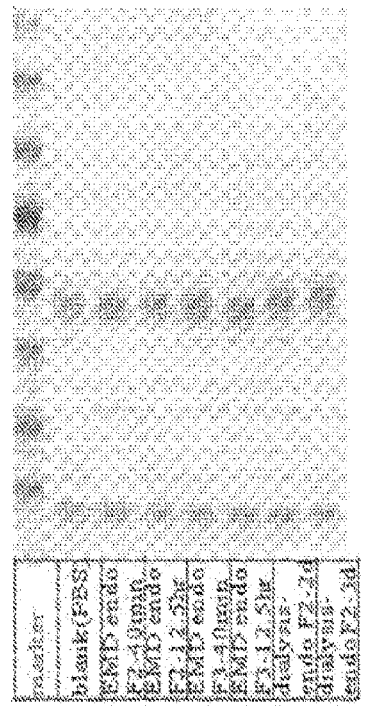
8-16% Tris-glycine gel

FIG. 7

| INN | Target; Format |
|---|---|
| Abciximab | GPIIb/IIIa; Chimeric IgG1 Fab |
| Adalimumab | TNF; Human IgG1 |
| Ado-trastuzumab emtansine | HER2; Humanized IgG1, ADC |
| Alemtuzumab | CD52; Humanized IgG1 |
| Alirocumab | PCSK9; Human IgG1 |
| Atezolizumab | PD-L1; Humanized IgG1 |
| Avelumab | PD-L1; Human IgG1 |
| Basiliximab | IL-2R; Chimeric IgG1 |
| Belimumab | BLyS; Human IgG1 |
| Benralizumab | IL-5Rα; Humanized IgG1 |
| Bevacizumab | VEGF; Humanized IgG1 |
| Bezlotoxumab | Clostridium difficile enterotoxin B; Human IgG1 |
| Blinatumomab | CD19, CD3; Murine bispecific tandem scFv |
| Brentuximab vedotin | CD30; Chimeric IgG1, ADC |
| Brodalumab | IL-17R; Human IgG2 |
| Burosumab | FGF23; Human IgG1 |
| Canakinumab | IL-1β; Human IgG1 |
| Caplacizumab | von Willebrand factor; Humanized Nanobody |
| Catumaxomab | EPCAM/CD3;Rat/mouse bispecific mAb |
| Cemiplimab | PD-1; Human mAb |
| Certolizumab pegol | TNF; Humanized Fab, pegylated |
| Cetuximab | EGFR; Chimeric IgG1 |
| Daclizumab | IL-2R; Humanized IgG1 |
| Daratumumab | CD38; Human IgG1 |
| Denosumab | RANK-L; Human IgG2 |
| Dinutuximab | GD2; Chimeric IgG1 |
| Dupilumab | IL-4Rα; Human IgG4 |
| Durvalumab | PD-L1; Human IgG1 |
| Eculizumab | C5; Humanized IgG2/4 |
| Edrecolomab | EpCAM; Murine IgG2a |
| Efalizumab | CD11a; Humanized IgG1 |

FIG. 7 Continued

| | |
|---|---|
| Elotuzumab | SLAMF7; Humanized IgG1 |
| Emapalumab | IFNgamma; Human IgG1 |
| Emicizumab | Factor IXa, X; Humanized IgG4, bispecific |
| Erenumab | CGRP receptor; Human IgG2 |
| Evolocumab | PCSK9; Human IgG2 |
| Fremanezumab | CGRP; Human IgG2 |
| Galcanezumab | CGRP; Human IgG4 |
| Gemtuzumab | CD33; Humanized IgG4, ADC |
| Golimumab | TNF; Human IgG1 |
| Guselkumab | IL-23 P19; Human IgG1 |
| Ibalizumab | CD4; Humanized IgG4 |
| Ibritumomab tiuxetan | CD20; Murine IgG1 |
| Idarucizumab | Dabigatran; |
| Idarucizumab | Humanized Fab |
| Infliximab | TNF; Chimeric IgG1 |
| Inotuzumab | CD22; Humanized IgG4, ADC |
| Ipilimumab | CTLA-4; Human IgG1 |
| Ixekizumab | IL-17a; Humanized IgG4 |
| Lanadelumab | Plasma kallikrein; Human IgG1 |
| Mepolizumab | IL-5; Humanized IgG1 |
| Mogamuizumab | CCR4; Humanized IgG1 |
| Moxetumomab pasudotox | CD22; Murine IgG1 dsFv immunotoxin |
| Muromonab-CD3 | CD3; Murine IgG2a |
| Natalizumab | a4 integrin; Humanized IgG4 |
| Nebacumab | Endotoxin; Human IgM |
| Necitumumab | EGFR; Human IgG1 |
| Nivolumab | PD1; Human IgG4 |
| Obiltoxaximab | Protective antigen of B. anthracis exotoxin; Chimeric IgG1 |
| Obinutuzumab | CD20; humanized IgG1; Glycoenginered |
| Ocrelizumab | CD20; Humanized IgG1 |
| Ofatumumab | CD20; Human IgG1 |
| Olaratumab | PDGRFα; Human IgG1 |
| Omalizumab | IgE; Humanized IgG1 |
| ozogamicin | CD22; Humanized IgG4, ADC |

FIG. 7 Continued

| | |
|---|---|
| ozogamicin | CD33; Humanized IgG4, ADC |
| Palivizumab | RSV; Humanized IgG1 |
| Panitumumab | EGFR; Human IgG2 |
| Pembrolizumab | PD1; Humanized IgG4 |
| Pertuzumab | HER2; Humanized IgG1 |
| Ramucirumab | VEGFR2; Human IgG1 |
| Ranibizumab | VEGF; Humanized IgG1 Fab |
| Ravulizumab | C5; Humanized IgG2/4 |
| Raxibacumab | B. anthrasis PA; Human IgG1 |
| Reslizumab | IL-5; Humanized IgG4 |
| Risankizumab | IL-23p19; Humanized IgG1 |
| Rituximab | CD20; Chimeric IgG1 |
| Romosozumab | Sclerostin; Humanized IgG2 |
| Sacituzumab govitecan | TROP-2; Humanized IgG1 ADC |
| Sarilumab | IL-6R; Human IgG1 |
| Secukinumab | IL-17a; Human IgG1 |
| Siltuximab | IL-6; Chimeric IgG1 |
| Tildrakizumab | IL-23p19; Humanized IgG1 |
| Tocilizumab | IL-6R; Humanized IgG1 |
| Tositumomab-I131 | CD20; Murine IgG2a |
| Trastuzumab | HER2; Humanized IgG1 |
| Ustekinumab | IL-12/23; Human IgG1 |
| Vedolizumab | α4β7 integrin; Humanized IgG1 |

FIG. 9

| Table 3 |
|---|
| Rituximab |
| Accession Number: DB00073 |
| Rituximab heavy chain(SEQ ID NO. 1)<br>QVQLQQPGAELVKPGASVKMSCKASGYTFTSYNMHWVKQTPGRGLEWIGAIYPGNGDTSY<br>NQKFKGKATLTADKSSSTAYMQLSSLTSEDSAVYYCARSTYYGGDWYFNVWGAGTTVTVS<br>AASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELLG<br>GPSVFLFPPKPKDTLMISRTPEVTCVVVDVSHEDPEVKFNWYVDGVEVHNAKTKPREEQY<br>NSTYRVVSVLTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLYSKLTVDKSR<br>WQQGNVFSCSVMHEALHNHYTQKSLSLSPGK<br><br>Rituximab light chain (SEQ ID NO. 2)<br>QIVLSQSPAILSASPGEKVTMTCRASSSVSYIHWFQQKPGSSPKPWIYATSNLASGVPVR<br>FSGSGSGTSYSLTISRVEAEDAATYYCQQWTSNPPTFGGGTKLEIKRTVAAPSVFIFPPS<br>DEQLKSGTASVVCLLNNFYPREAKVQWKVDNALQSGNSQESVTEQDSKDSTYSLSSTLTL<br>SKADYEKHKVYACEVTHQGLSSPVTKSFNRGEC |

SEQUENCE LISTING

```
<160> NUMBER OF SEQ ID NOS: 2

<210> SEQ ID NO 1
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30
```

```
Asn Met His Trp Val Lys Gln Thr Pro Gly Arg Gly Leu Glu Trp Ile
         35                  40                  45
Gly Ala Ile Tyr Pro Gly Asn Gly Asp Thr Ser Tyr Asn Gln Lys Phe
 50                      55                  60
Lys Gly Lys Ala Thr Leu Thr Ala Asp Lys Ser Ser Ser Thr Ala Tyr
 65                  70                  75                  80
Met Gln Leu Ser Ser Leu Thr Ser Glu Asp Ser Ala Val Tyr Tyr Cys
                 85                  90                  95
Ala Arg Ser Thr Tyr Tyr Gly Gly Asp Trp Tyr Phe Asn Val Trp Gly
             100                 105                 110
Ala Gly Thr Thr Val Thr Val Ser Ala Ala Ser Thr Lys Gly Pro Ser
         115                 120                 125
Val Phe Pro Leu Ala Pro Ser Ser Lys Ser Thr Ser Gly Gly Thr Ala
 130                     135                 140
Ala Leu Gly Cys Leu Val Lys Asp Tyr Phe Pro Glu Pro Val Thr Val
 145                 150                 155                 160
Ser Trp Asn Ser Gly Ala Leu Thr Ser Gly Val His Thr Phe Pro Ala
                 165                 170                 175
Val Leu Gln Ser Ser Gly Leu Tyr Ser Leu Ser Ser Val Val Thr Val
             180                 185                 190
Pro Ser Ser Ser Leu Gly Thr Gln Thr Tyr Ile Cys Asn Val Asn His
         195                 200                 205
Lys Pro Ser Asn Thr Lys Val Asp Lys Lys Val Glu Pro Lys Ser Cys
 210                     215                 220
Asp Lys Thr His Thr Cys Pro Pro Cys Pro Ala Pro Glu Leu Leu Gly
 225                 230                 235                 240
Gly Pro Ser Val Phe Leu Phe Pro Pro Lys Pro Lys Asp Thr Leu Met
                 245                 250                 255
Ile Ser Arg Thr Pro Glu Val Thr Cys Val Val Val Asp Val Ser His
             260                 265                 270
Glu Asp Pro Glu Val Lys Phe Asn Trp Tyr Val Asp Gly Val Glu Val
         275                 280                 285
His Asn Ala Lys Thr Lys Pro Arg Glu Glu Gln Tyr Asn Ser Thr Tyr
 290                     295                 300
Arg Val Val Ser Val Leu Thr Val Leu His Gln Asp Trp Leu Asn Gly
 305                 310                 315                 320
Lys Glu Tyr Lys Cys Lys Val Ser Asn Lys Ala Leu Pro Ala Pro Ile
                 325                 330                 335
Glu Lys Thr Ile Ser Lys Ala Lys Gly Gln Pro Arg Glu Pro Gln Val
             340                 345                 350
Tyr Thr Leu Pro Pro Ser Arg Asp Glu Leu Thr Lys Asn Gln Val Ser
         355                 360                 365
Leu Thr Cys Leu Val Lys Gly Phe Tyr Pro Ser Asp Ile Ala Val Glu
 370                     375                 380
Trp Glu Ser Asn Gly Gln Pro Glu Asn Asn Tyr Lys Thr Thr Pro Pro
 385                 390                 395                 400
Val Leu Asp Ser Asp Gly Ser Phe Phe Leu Tyr Ser Lys Leu Thr Val
                 405                 410                 415
Asp Lys Ser Arg Trp Gln Gln Gly Asn Val Phe Ser Cys Ser Val Met
             420                 425                 430
His Glu Ala Leu His Asn His Tyr Thr Gln Lys Ser Leu Ser Leu Ser
         435                 440                 445
Pro Gly Lys
```

```
<210> SEQ ID NO 2
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

METHODS FOR MODIFYING HUMAN ANTIBODIES BY GLYCAN ENGINEERING

CROSS-REFERENCE TO RELATED APPLICATION(S)

This patent application claims the benefit or priority of, and is a Continuation-in-Part of, U.S. application Ser. No. 12/959,351, filed Dec. 2, 2010, now U.S. Pat. No. 10,087, 236, which claims priority of U.S. Provisional Patent Application Ser. No. 61/265,757, filed Dec. 2, 2009. This patent application is also a Continuation-in-Part of U.S. application Ser. No. 16/018,400, filed Jun. 26, 2018, which claims priority to U.S. application Ser. No. 14/723,297, filed May 27, 2015, now U.S. Pat. No. 10,023,892, which claims priority to US provisional applications U.S. Ser. No. 62/003, 136, filed May 27, 2014, U.S. Ser. No. 62/003,104, filed May 27, 2014 U.S. Ser. No. 62/003,908, filed May 28, 2014, U.S. Ser. No. 62/020,199, filed Jul. 2, 2014, and U.S. Ser. No. 62/110,338, filed Jan. 30, 2015, the contents of each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Feb. 19, 2019, is named G2112-00604_SL.txt and is 6,550 bytes in size.

TECHNICAL FIELD OF THE INVENTION

This invention relates to the field of antibodies. In particular, the application relates to methods for modifying glycosylation states of human monoclonal antibodies (mAbs) by glycan engineering. More particularly, the application relates to uniformly glycosylated glycoforms of Fc regions of human mAbs and methods for preparing the antibodies by glycan engineering.

BACKGROUND OF THE INVENTION

Antibodies, also known as immunoglobulins (Ig), are glycoproteins that play a central role in immune responses. IgG antibodies (Abs) and fragments of IgG Abs have become major biotherapeutics for treating human diseases.

There are five functional classes of immunoglobulins, i.e., immunoglobulin M (IgM), immunoglobulin D (IgD), immunoglobulin G (IgG), immunoglobulin A (IgA) and immunoglobulin E (IgE). Among them, IgG is the most abundant immunoglobulin in serum.

The variable region (Fab) of the antibody molecule is involved in direct binding of the target antigen. All naturally-occurring antibodies each include a constant domain known as the Fc (Fragment, crystallizable) region, which is composed of constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins. By doing this, it mediates different physiological effects including opsonization, cell lysis, and degranulation of mast cells, basophils and eosinophils. (Woof J, Burton D (2004) Nat Rev Immunol 4 (2): 89-99; Heyman B (1996) Immunol. Lett. 54 (2-3): 195-199). Glycosylation of the antibody Fc fragment is essential for Fc receptor-mediated activity. (Peipp M. et al., Blood (2008) 112(6):2390-2399).

The constant (Fc) domain of naturally-occurring antibodies is usually N-glycosylated. The linkage of carbohydrates to proteins occurs through N-linked glycosylation—the attachment of a sugar to the amide nitrogen atom on the side chain of asparagines. The linkage to amino acids is generally embedded in a conserved sequence of amino acids. Glycosylation in the Fc region significantly affects Fc effector functions such as activation of complement (Roos et al., J Immunol. (12):7052-7059.2001) or binding to receptors via their constant (invariable sequence) domains (Mimura et al., J Biol. Chem. 2001 Dec. 7; 276(49):45539-45547; Shields et al., J Biol. Chem. 276(9):6591-6604 (2001)).

It has been found that the sequences of the oligosaccharides attached to Fc regions are essential to the stability and function of the antibodies. For example, the addition of sialic acid (SA), sialylation, at Asn 297 on the Fc domain and terminal galactosylation modify the anti-inflammatory properties of immunoglobulins and play a role in rheumatoid arthritis (RA). (Kaneko, Y et al., Science. (2006) 313(5787): 670-673).

Human antibodies prepared by conventional methods, such as genetic engineering, comprise mixtures of different glycoforms, i.e., containing different oligosaccharides attached to their Fc regions.

The clinical successes of the antibodies rituximab and alemtuzumab for hematological malignancies, and trastuzumab for solid breast tumors, have demonstrated that human or humanized monoclonal antibodies can be useful drugs for the treatment of cancer. All of these antibodies have been approved and are currently in the market. Yet, a need remains for improving this kind of drugs. For instance, rituximab induces a response only in approximately 60% of the patients with relapsed/refractory low-grade non-Hodgkin's lymphoma.

The preferred type of monoclonal antibody for target-cell killing applications is an IgG1-type mAb, where at least the constant (or the Fc) region is of human origin (i.e., chimeric, humanized, or fully-human IgG1s). IgG1 mAbs can exert their therapeutic effects via three classes of mechanisms. Direct binding of the antibody via its variable region to the target molecule on the surface of cancer cells can lead to cell death or inhibition of tumor growth, for example by triggering apoptosis upon cross-linking of target molecules by the antibody. The Fc region operates in the other two-types of mechanisms: complement-mediated cytotoxicity, and Fcγ receptor (FcγR)-dependent effector functions. Some Fc effector functions of IgG1s are mediated by the interactions of the Fc region of target-cell bound antibody molecules and Fcγ receptors on the surface of immune cells. The Fc domains of immunoglobulins have been shown to have effector functions which are primarily complement fixation and Fc receptor (FcR) binding. appropriate glycosylation at the conserved glycosylation site (N297) of the Fc domain is essential for the efficient interactions between mAbs and Fc receptors (FcR) and for the FcR-mediated effector functions, including antibody-dependent cell mediated cytotoxicity (ADCC) and complement-dependent cytotoxicity (CDC). Fc receptors bind to the constant domains of immunoglobulins and a number of receptors have been defined that are thought to mediate accessory functions including opsonization and ADCC (Daeron, M. Annual Review Immunology, (1997) 15; 203-234, Ravetch and Clynes, Annual Review of Immunology. 1998. 16:421-432).

The conserved glycosylation site on the Fc region of antibodies is a target for modulation of antibody effector functions. The crystal structure of a biosynthetic intermediate of human IgG1, bearing immature oligomannose-type glycans and reported to display increased antibody-dependent cellular cytotoxicity, has shown that glycan engineering can bias the Fc to an open conformation primed for receptor binding. (Crispin M., et al., J. Mol. Biol. 387(5):1061-1066 (2009).)

More specifically, certain glycoforms of a human antibody exhibit improved therapeutic effects while others possess undesired properties. For example, de-fucosylated but glycosylated Herceptin® is at least 50-fold more active in the efficacy of Fcγ receptor IIIa mediated ADCC than those with alpha-1,6-linked fucose residues (Shields, R L, et al. J. Biol. Chem., Vol. 277(30):26733-26740, (2002)). Similar results were reported for Rituximab® and other mAbs (Shinkawa T, et al., J. Biol. Chem. (2003) 278:3466-3473).

Strome et al., (WO 2007/146847) disclose a method of preparing antibodies with homogeneous glycosylation states by first deglycosylating an antibody or antibody fragment and then attaching a chemically synthesized sugar to the protein. This method lacks the ability to control the glycosylation process and does not enable control over the conjugation of specific carbohydrates at specific sites during the formation of a desired glycoform. Thus, there is a need for methods of preparing human antibodies comprising desired glycoform(s) wherein the glycosylation is performed in a stepwise manner so as to improve their therapeutic efficacy.

SUMMARY OF THE INVENTION

Provided herein are methods for engineering the glycan on the Fc region of a human, chimeric, or humanized glycosylated antibody, wherein the glycosylated antibody comprises an oligosaccharide attached at Asn-297, wherein the oligosaccharide includes or excludes a core fucose. In some embodiments the method can include the steps of contacting the antibody with a β-1,4-galactosyltransferase and UDP galactose thereby coupling the terminal unit of the oligosaccharide to the galactose to form an oligosaccharide having a terminal galactose unit, wherein the oligosaccharide having a terminal galactose unit is attached at each Asn 297 of the Fc region of the human, chimeric or humanized glycosylated antibody; and contacting the antibody comprising the oligosaccharide having a terminal galactose with an alpha-2,6-sialyltransferase and CMP-Neu5Ac, thereby adding a terminal Neu5Ac to each terminal galactose unit to form an oligosaccharide having a terminal Neu5Ac2Gal2, wherein the oligosaccharide having a terminal Neu5Ac2Gal2 is attached at each Asn 297 of the Fc region of the human, chimeric or humanized glycosylated antibody. In some embodiments, the method can include the step of providing the human, chimeric, or humanized glycosylated antibody, wherein the glycosylated antibody. The human, chimeric, or humanized glycosylated antibody can be an IgG, IgE. IgA, IgD, or and IgM. In some embodiments the IgG can be an IgG1, an IgG2, an IgG3, or an IgG4. The human, chimeric, or humanized glycosylated antibody can be a therapeutic antibody selected from the group consist of ravulizumab, sacituzumab, risankizumab, emapalumab, cemiplimab, galcanezumab, fremanezumab, romosozumab, moxetumomab, caplacizumab, lanadelumab, mogamuizumab, erenumab, tildrakizumab, ibalizumab, burosumab, durvalumab, emicizumab, benralizumab, ocrelizumab, guselkumab, inotuzumab, sarilumab, dupilumab, avelumab, brodalumab, atezolizumab, bezlotoxumab, olaratumab, reslizumab, obiltoxaximab, ixekizumab, daratumumab, elotuzumab, necitumumab, idarucizumab, alirocumab, mepolizumab, evolocumab, dinutuximab, secukinumab, nivolumab, blinatumomab, pembrolizumab, ramucirumab, vedolizumab, siltuximab, obinutuzumab, trastuzumab, raxibacumab, pertuzumab, brentuximab, belimumab, ipilimumab, denosumab, tocilizumab, ofatumumab, canakinumab, golimumab, ustekinumab, certolizumab, catumaxomab, eculizumab, ranibizumab, panitumumab, natalizumab, bevacizumab, cetuximab, efalizumab, omalizumab, tositumomab, ibritumomab, adalimumab, alemtuzumab, gemtuzumab, trastuzumab, infliximab, palivizumab, basiliximab, daclizumab, rituximab, abciximab, edrecolomab, nebacumab, and muromonab. In some embodiments, the oligosaccharide attached at Asn-297 can include an oligosaccharide moiety having the structure of $Gal_2GlcNAc_2Man_3GlcNAc_2$, $GalGlcNAc_2Man_3GlcNAc_2$, or $GlcNAc_2Man_3GlcNAc_2$ the glycan engineered human, chimeric or humanized antibody can have an $Neu5Ac_2Gal_2GlcNAc_2Man_3GlcNAc_2$ attached at each Asn 297 in the Fc region. In some embodiments, the method can include a set of CMP-Neu5Ac regeneration enzymes comprising a pyrophosphatase and a cytidine monophosphate kinase, and wherein the CMP-Neu5Ac is regenerated following the addition of the terminal Neu5Ac. The glycan engineered human, chimeric or humanized antibody can be further purified.

Also provided are methods for making an essentially pure population of glycoengineered human, chimeric, or humanized glycosylated antibodies from a population of precursor human, chimeric, or humanized glycosylated antibodies, wherein the precursor glycosylated antibodies have an oligosaccharide attached at Asn-297, wherein the oligosaccharide includes or excludes a core fucose, the method comprising contacting the precursor antibodies with a β-1,4-galactosyltransferase and UDP galactose thereby coupling the terminal unit of the oligosaccharide to the galactose to form an oligosaccharide having a terminal galactose unit, wherein the oligosaccharide having a terminal galactose unit is attached at each Asn 297 of the Fc region of the human, chimeric or humanized glycosylated antibody; and contacting the antibodies comprising the oligosaccharide having a terminal galactose with an alpha-2,6-sialyltransferase and CMP-Neu5Ac, thereby adding a terminal Neu5Ac to each terminal galactose unit to form an oligosaccharide having a terminal Neu5Ac2Gal2, wherein the oligosaccharide having a terminal Neu5Ac2Gal2 is attached at each Asn 297 of the Fc region of the human, chimeric or humanized glycosylated antibodies, and wherein the essentially pure population of glycoengineered human, chimeric, or humanized glycosylated antibodies comprises at least about 85% by weight of the glycoengineered human, chimeric, or humanized glycosylated antibodies.

Also provided are pharmaceutical formulations comprising an antibody prepared by the methods disclosed herein. The antibody can have the glycan structure of: $Sia_2(a2-6)Gal_2GlcNAc_2Man_3GlcNAc_2$ attached to the Asn297 of the Fc region.

The details of one or more embodiments of the invention are set forth in the description below. Other features or advantages of the present invention will be apparent from the following drawing and detailed description of several embodiments, and also from the appended claims.

DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIG. 5A shows a schematic illustration of digestion of heterogeneous glycoforms of Humira® obtained from Chinese hamster ovary (CHO) cells with Endo F2 and Endo F3. The results are shown in Coomassie stained polyacrylamide gels in FIG. 5B.

FIG. 7 is a table listing representative therapeutic antibodies. (Note: Related Antibod fragments and ADCs are shown)

FIG. 9 is a table showing the amino acid sequences of the heavy chain (SEQ ID NO. 1) of Rituximab and the light chain (SEQ ID NO. 2) of Rituximab.

DETAILED DESCRIPTION OF THE INVENTION

Figure 1:
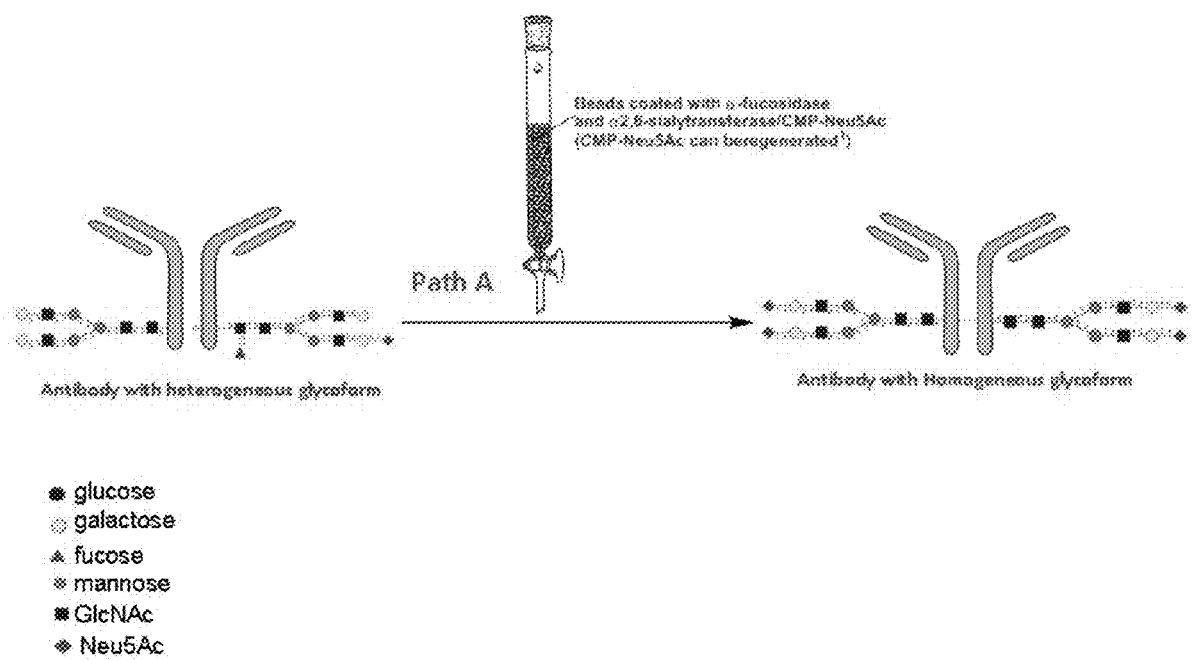
FIG. 1 shows a schematic illustration depicting a pathway (Path A) for modifying a representative human antibody by glycan engineering, using alpha-fucosidase, alpha-2,6-sialyltransferase, and optionally β-1,4-galactosyltransferase.

Disclosed herein are modified human antibodies prepared via glycan engineering. The invention relates to the Fc region of an antibody molecule, wherein the Fc region is specifically glycosylated with oligosaccharides that increase the efficacy and stability of the Fc region, and the antibody or antibody fragment comprising the Fc region. In some embodiments the specifically glycosylated Fc fragment comprises a monoclonal antibody, preferably a human or humanized monoclonal antibody. Methods for generating such Fc glycosylated antibodies or antibody fragments by glycan engineering are disclosed herein.

Provided herein are materials and methods for efficient production of homogeneous populations of glycoengineered antibodies having the structure Neu5Ac$_2$Gal$_2$GlcNAc$_2$Man$_3$GlcNAc$_2$ attached at each Asn 297 in the Fc region. Such antibodies provide enhanced therapeutic benefits relative to parental antibodies that have heterogeneous glycan structures attached at Asn 297 in the Fc region. Specifically, glycoengineered antibodies have enhanced efficacy of effector cell function mediated via increased FcγRIIIA binding and antibody-dependent cytotoxicity (ADCC) compared to the parental antibodies. The inventors have found that enzymatic treatment of populations of antibodies having heterogeneous glycan structures attached at Asn 297 permitted the in situ conversion of heterogeneous glycan structures to homogeneous glycan structures without the need for removal of the heterogeneous glycan structures followed by their replacement with homogeneous glycan structures.

In one embodiment, a two-step method is provided. In the first step, the native glycoantibody can be treated with β-1,4-galactosyltransferase and UDP galactose. The β-1,4-galactosyltransferase specifically catalyzes the addition of galactose to any glycan structures having a terminal GlcNAc. Exemplary glycan substrates include GalGlcNAc$_2$Man$_3$GlcNAc ("G1"), and the GlcNAc$_2$Man$_3$GlcNAc ("G0"). The glycan substrates can include or exclude a core fucose, that is, the exemplary structures "G0F" and"G0" respectively. The β-1,4-galactosyltransferase treatment generates an "intermediate" population of antibodies having an oligosaccharide structure having a terminal galactose unit, wherein the oligosaccharide having a terminal galactose unit is attached at each Asn 297 of the Fc region of the human, chimeric or humanized glycosylated antibody. An exemplary glycan structure intermediate population antibodies can be Gal$_2$GlcNAc$_2$Man$_3$GlcNAc$_2$ (G2/G2F) attached at each Asn 297 of the Fc region. For the second step, the "intermediate" population of antibodies can be treated with alpha-2,6-sialyltransferase and CMP-Neu5Ac (also referred to as CMP-sialic acid). The alpha-2,6-sialyltransferase specifically catalyzes the addition of Neu5Ac to the terminal galactose unit of the intermediate population of antibodies produced in the first step as well as to any native antibodies having a terminal galactose unit, to form an oligosaccharide having a terminal Neu5Ac2Gal$_2$ attached at each Asn 297 of the Fc region of the human, chimeric or humanized glycosylated antibody. Thus, the second step of the method can produce a population of homogeneously glycosylated antibodies having, for example, the structure Neu5Ac$_2$Gal$_2$GlcNAc$_2$Man$_3$GlcNAc$_2$ ("G2S2/G2S2F") attached at each Asn 297 in the Fc region.

The methods disclosed herein can be applied to a glycosylated antibody, for example, a human, chimeric, or humanized glycosylated antibody. The glycosylated antibody can include or exclude a core fucose. The glycosylated antibody can be a therapeutic antibody, for example, any of the antibodies listed in the table in FIG. 7. In some embodiments, the therapeutic antibody can be a commercially available antibody. Exemplary therapeutic antibodies include, for example, without limitation, ravulizumab, sacituzumab, risankizumab, emapalumab, cemiplimab, galcanezumab, fremanezumab, romosozumab, moxetumomab, caplacizumab, lanadelumab, mogamuizumab, erenumab, tildrakizumab, ibalizumab, burosumab, durvalumab, emicizumab, benralizumab, ocrelizumab, guselkumab, inotuzumab, sarilumab, dupilumab, avelumab, brodalumab, atezolizumab, bezlotoxumab, olaratumab, reslizumab, obiltoxaximab, ixekizumab, daratumumab, elotuzumab, necitumumab, idarucizumab, alirocumab, mepolizumab, evolocumab, dinutuximab, secukinumab, nivolumab, blinatumomab, pembrolizumab, ramucirumab, vedolizumab, siltuximab, obinutuzumab, trastuzumab, raxibacumab, pertuzumab, brentuximab, belimumab, ipilimumab, denosumab, tocilizumab, ofatumumab, canakinumab, golimumab, ustekinumab, certolizumab, catumaxomab, eculizumab, ranibizumab, panitumumab, natalizumab, bevacizumab, cetuximab, efalizumab, omalizumab, tositumomab, ibritumomab, adalimumab, alemtuzumab, gemtuzumab, trastuzumab, infliximab, palivizumab, basiliximab, daclizumab, rituximab, abciximab, edrecolomab, nebacumab, and muromonab.

The methods disclosed herein include one or more enzymes that catalyze the transfer of a specific saccharide moiety to the terminal unit of an N-glycan. An enzyme can be a galactosyltransferase, an enzyme that transfers a galactose to specific acceptor structures in the glycan. A galactosyltransferase can be, for example, β-1,4-galactosyltransferase, which catalyzes the specific transfer of a galactose from a UDP-α-D-galactose to generate a β1-4-linkage with a terminal GlnAc unit. β-1,4-galactosyltransferase (EC: 2.4.1.-) is also referred to as β-1,4-galactosyltransferase 1, Beta-1,4-GalTase 1, Beta4Gal-T1, b4Gal-T1, UDP-Gal:beta-GlcNAc beta-1,4-galactosyltransferase 1 and UDP-galactose:beta-N-acetylglucosamine beta-1,4-galactosyltransferase 1. The β-1,4-galactosyltransferase family consists of at least seven members, Gal-T1 to Gal-T7 with a 25% to 55% sequence homology. Each subfamily member is expressed in a tissue-specific manner and shows differences in the oligosaccharide acceptor specificity. Useful β-1,4-galactosyltransferases are specific for a terminal GlnAc acceptor. In some embodiments, useful galactosyltransferases will have minimal activity on N-glycan substrates having a terminal galactose residue.

Alternatively or in addition, a galactosyltransferase can be, for example, β-1,3-galactosyltransferase (EC:2.4.1.) β-1,3-galactosyltransferase (EC:2.4.1.) β-1,3-galactosyltransferase is also referred to as β-1,3-galactosyltransferase 2, Beta-1,3-GalTase 2, Beta3Gal-T2, and UDP-galactose:2-acetamido-2-deoxy-D-glucose 3beta-galactosyltransferase The methods disclosed herein include one or more sialyltransferase enzymes that catalyze the specific transfer of a sialic acid moiety to the terminal unit, for example a terminal galactose, of an N-glycan. In some embodiments, the sialyltransferase can be an alpha-2,6-sialyltransferase (EC: 2.4.99.1), which catalyzes the transfer of sialic acid from CMP-sialic acid (CMP-N-acetyl-beta-neuraminate) to galactose-containing acceptor substrates to generate an.N-acetyl-alpha-neuraminyl-2-6 linkage with a terminal galactose unit of the N-glycan. Alpha-2,6-sialyltransferase is also referred to as Beta-galactoside alpha-2,6-sialyltransferase 1, Alpha 2,6-ST 1, B-cell antigen CD75, CMP-N-acetylneuraminate-beta-galactosamide-alpha-2,6-sialyltransferase 1, ST6Gal I, and Sialyltransferase 1. In some embodiments, the sialytransferase can be an alpha-2,3-sialyltransferase (EC: 2.4.99.4), which catalyzes the transfer of sialic acid from CMP-sialic acid (CMP-N-acetyl-beta-neuraminate) to galactose-containing acceptor substrates to generate an.N-acetyl-alpha-neuraminyl-2-3 linkage with a terminal galactose unit of the N-glycan.

Figure 6:
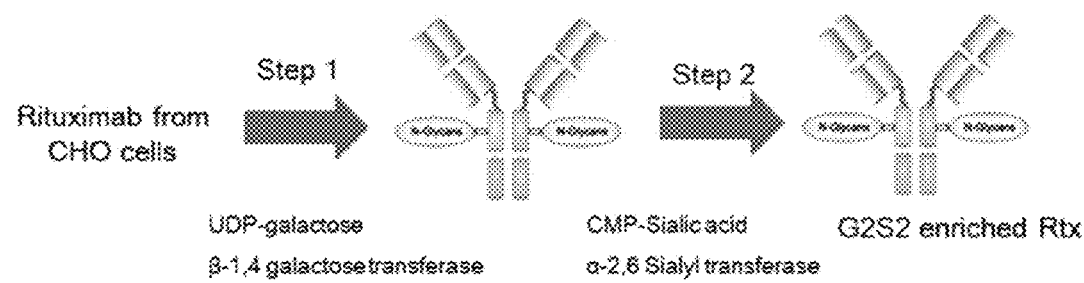
FIG. 6 shows a schematic illustration of depicting a method of engineering a glycan on the FC region of a glycoantibody.

The glycosylated parental antibody can be contacted with the enzyme, for example, the galactosyltransferase, in solution, under conditions and for a time sufficient to transfer of a galactose from a UDP-α-D-galactose to generate a β1-4-linkage with a terminal GlnAc unit. In some embodiments, the galactose can be transferred to only one GlnAc unit to produce a glycan having, for example, the structure GalGlcNAcMan$_3$GlcNAc$_2$ (G1F/G1F') as shown in FIG. 6. In some embodiments, the galactose can be transferred to more than one GlnAc unit to produce a glycan having, for example, the structure Gal$_2$GlcNAc$_2$Man$_3$GlcNAc$_2$ (G2/G2F) as shown in FIG. 6. In some embodiments, the galactosyltransferase can be immobilized on a solid support. Following the transfer of the galactose to the terminal GlnAc unit, the resulting "intermediate" population of glycosylated antibodies can be contacted with the sialyltransferase, for example, an alpha-2,6-sialyltransferase, in solution, under conditions and for a time sufficient to transfer of sialic acid from CMP-sialic acid to galactose-containing acceptor substrates to generate an.N-acetyl-alpha-neuraminyl-2-6 linkage with a terminal galactose unit of the N-glycan. In some embodiments, the sialic acid can be transferred to one terminal galactose to produce an N-glycan having, for example, the structure Sia(α2-6)Gal$_2$GlcNAc$_2$Man$_3$GlcNAc$_2$. In some embodiments, the sialic acid can be transferred to more than one terminal galactose to produce an N-glycan having, for example, the structure Sia$_2$(α2-6)Gal$_2$GlcNAc$_2$Man$_3$GlcNAc$_2$. In some embodiments, the sialyltransferase can be immobilized on a solid support.

In some embodiments, the parental antibody can be characterized prior to the enzymatic treatments in order to determine the relative amounts of the specific N-glycan structures present on the heterogeneously glycosylated parental antibody. Such characterization can be carried out, for example, using LC-MS or LC-MS/MS.

In some embodiments, the glycoengineered antibody can be increased in concentration relative to the reaction by-products. In some embodiments, the increase in the concentration of the glycoengineered antibody can be achieved by purifying the glycoengineered antibody. The purification can be performed using a purification method selected from: extraction, chromatography, dialysis, precipitation, filtration, centrifugation, or combinations thereof. In some embodiments, extraction purification can include or exclude extracting the antibody in an organic solvent from a solvent-aqueous mixture. In some embodiments, chromatography purification can include or exclude: size-exclusion chromatography, gel permeation chromatography, thiophilic chromatography, ion-exchange chromatography, ligand chromatography, hydrophobic interaction chromatography, free-flow electrophoresis, and combinations thereof. In some embodiments, ligand chromatography can include or exclude protein A, protein G, or protein L-bound bead-based chromatography. In some embodiments, dialysis purification can be performed by placing the reaction solution in an enclosure surrounded by a molecular-weight cutoff (MWCO) membrane wherein the molecular weight of the antibody is larger than the MWCO of the dialysis membrane, and the enclosure placed in a buffer or solution to remove small molecule reaction by-products. In some embodiments, the precipitation purification method can be include or exclude ammonium sulfate, potassium sulfate, ammonium acetate, and potassium acetate. In some embodiments, the filtration purification can include or exclude gel filtration. In some embodiments, the centrifugation purification can include or exclude ultracentrifugation, and sucrose gradient centrifugation.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

(1) Definitions

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds), Immunochemical Methods In Cell And Molecular Biology (Mayer and Walker, eds., Academic Press, London, 1987); Antibodies: A Laboratory Manual, by Harlow and Lane s (Cold Spring Harbor Laboratory Press, 1988); and Handbook Of Experimental Immunology, Volumes I-IV (D. M. Weir and C. C. Blackwell, eds., 1986).

The term "glycoantibodies" was coined by the inventor, Dr. Chi-Huey Wong, to refer to a homogeneous population of monoclonal antibodies (preferably, therapeutic monoclonal antibodies) having a single, uniformed glycoform bound to the Fc region. The individual glycoantibodies comprising the essentially homogeneous population are identical, bind to the same epitope, and contain the same Fc glycan with a well-defined glycan structure and sequence. As used herein, the term "anti-CD20 glycoantibodies" ("anti-CD20 GAbs") refers to a homogeneous population of anti-CD20 IgG molecules having the same glycoform on Fc. The term "anti-CD20 glycoantibody" ("anti-CD20 GAb") refers to an individual IgG antibody molecule in the anti-CD20 glycoantibodies. As used herein, "molecule" can also refer to antigen binding fragments.

As used herein, the term "glycan" refers to a polysaccharide, or oligosaccharide. or monosaccharide. Glycans can be monomers or polymers of sugar residues and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6' sulfo N-acetylglucosamine, etc). Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of $\beta$-1,4-linked D-glucose, and chitin is a glycan composed of $\beta$-1,4-linked N-acetyl-D-glucosamine Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Ser or Asn-X-Thr sequence, where X is any amino acid except proline.

As used herein, the terms "fucose", "core fucose" and "core fucose residue" are used interchangeably and refer to a fucose in $\alpha$1,6-position linked to the N-acetylglucosamine.

As used herein, the terms "N-glycan", "N-linked glycan", "N-linked glycosylation", "Fc glycan" and "Fc glycosylation" are used interchangeably and refer to an N-linked oligosaccharide attached by an N-acetylglucosamine (GlcNAc) linked to the amide nitrogen of an asparagine residue in a Fc-containing polypeptide. The term "Fc-containing polypeptide" refers to a polypeptide, such as an antibody, which comprises an Fc region.

As used herein, the term "glycosylation pattern" and "glycosylation profile" are used interchangeably and refer to the characteristic "fingerprint" of the N-glycan species that have been released from a glycoprotein or antibody, either enzymatically or chemically, and then analyzed for their carbohydrate structure, for example, using LC-HPLC, or MALDI-TOF MS, and the like. See, for example, the review in Current Analytical Chemistry, Vol. 1, No. 1 (2005), pp. 28-57; herein incorporated by reference in its entirety.

As used herein, the term "glycoengineered Fc" when used herein refers to N-glycan on the Fc region has been altered or engineered either enzymatically or chemically. The term "Fc glycoengineering" as used herein refers to the enzymatic or chemical process used to make the glycoengineered Fc. Exemplary methods of engineering are described in, for example, Wong et al U.S. Ser. No. 12/959,351, the contents of which is hereby incorporated by reference.

The terms "homogeneous", "uniform", "uniformly" and "homogeneity" in the context of a glycosylation profile of Fc region are used interchangeably and are intended to mean a single glycosylation pattern represented by one desired N-glycan species, with little or no trace amount of precursor N-glycan. In certain embodiments, the trace amount of the precursor N-glycan is less than about 2%.

"Essentially pure" protein means a composition comprising at least about 90% by weight of the specific protein, based on total weight of the composition, including, for example, at least about 85%, 86%, 87%, 88%, 89%, 90%, 91%, at least about 92%, at least about 93%, at least about 94%, at least about 95%, at least about 96%, at least about 97%, at least about 98%, or at least about 99% by weight.

An "essentially homogeneous" glycoengineered antibody means a composition comprising at least about 80%, 81%, 82%, 83%, 84%, 85% by weight of the glycoengineered antibody, including for example, at least about 85%, 86%, 87%, 88%, 89%, 90%, 91%, 92%, 93% 94%, 95%, 96%, 97%, at least about 98%, at least about 98.5%, at least about 99% based on total weight of the glycoengineered antibodies in the composition. In certain embodiments, the glycoengineered antibody is a structural variants, and/or antigen binding fragment thereof.

As used herein, the terms "IgG", "IgG molecule", "monoclonal antibody", "immunoglobulin", and "immunoglobulin molecule" are used interchangeably. As used herein, "molecule" can also refer to antigen binding fragments.

As used herein, the term "Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI (CD64), FcγRII (CD32), and FcγRIII (CD16) subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, $Annu. Rev. Immunol.$ 15:203-234 (1997)). FcRs are reviewed in Ravetch and Kinet, $Annu. Rev. Immunol$ 9:457-92 (1991); Capel et al., $Immunomethods$ 4:25-34 (1994); and de Haas et al., $J. Lab. Clin. Med.$ 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., $J. Immunol.$ 117:587 (1976) and Kim et al., $J. Immunol.$ 24:249 (1994)).

The term "effector function" as used herein refers to a biochemical event that results from the interaction of an antibody Fc region with an Fc receptor or ligand. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions can be assessed using various assays known in the art.

As used herein, the term "Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, $Annu. Rev. Immunol$ 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. $PNAS (USA)$ 95:652-656 (1998).

The term "Complement dependent cytotoxicity" or "CDC" as used herein refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., $J. Immunol. Methods$ 202:163 (1996), may be performed.

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., $Proc. Natl. Acad. Sci. USA$ 81:6851-6855 (1984)). Humanized antibody as used herein is a subset of chimeric antibodies.

"Humanized" forms of non-human (e.g., murine) antibodies are chimeric antibodies which contain minimal sequence derived from non-human immunoglobulin. For the most part, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR is typically no more than 6 in the H chain, and in the L chain, no more than 3. The humanized antibody optionally also will comprise at least a portion of an immunoglobulin constant region (Fc), typically that of a human immunoglobulin. For further details, see Jones et al., $Nature$ 321:522-525 (1986); Reichmann et al., $Nature$ 332:323-329 (1988); and Presta, $Curr. Op. Struct. Biol.$ 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

As used herein, the term "antigen" is defined as any substance capable of eliciting an immune response. As used herein, the term "antigen specific" refers to a property of a cell population such that supply of a particular antigen, or a fragment of the antigen, results in specific cell proliferation.

As used herein, the term "immunogenicity" refers to the ability of an immunogen, antigen, or vaccine to stimulate an immune response.

As used herein, the term "epitope" is defined as the parts of an antigen molecule which contact the antigen binding site of an antibody or a T cell receptor.

As used herein, the term "specifically binding," refers to the interaction between binding pairs (e.g., an antibody and an antigen). In various instances, specifically binding can be embodied by an affinity constant of about 10−6 moles/liter, about 10−7 moles/liter, or about 10−8 moles/liter, or less.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes.

The phrase "substantially similar," "substantially the same", "equivalent", or "substantially equivalent", as used herein, denotes a sufficiently high degree of similarity between two numeric values (for example, one associated with a molecule and the other associated with a reference/comparator molecule) such that one of skill in the art would consider the difference between the two values to be of little or no biological and/or statistical significance within the context of the biological characteristic measured by said values (e.g., Kd values, anti-viral effects, etc.). The difference between said two values is, for example, less than about 50%, less than about 40%, less than about 30%, less than about 20%, and/or less than about 10% as a function of the value for the reference/comparator molecule.

The phrase "substantially reduced," or "substantially different", as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

The "variable region" or "variable domain" of an antibody refers to the amino-terminal domains of heavy or light chain of the antibody. These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ) based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1, and IgA2. The heavy chain constant domains that correspond to the different classes of immunoglobulins are called $\alpha$, $\delta$, $\epsilon$, $\gamma$, and $\mu$, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2nd ed. 1988); Hammerling et al., in: Monoclonal Antibodies and T-Cell hybridomas 563-681 (Elsevier, N.Y., 1981)), recombinant DNA methods (see, e.g., U.S. Pat. No. 4,816,567), phage display technologies (See, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| (Kabat Numbering) | | | | |
| H1 | H31-H35 | H26-H35 | H26-H32 | H30-H35 |
| (Chothia Numbering) | | | | |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-36 or 24-34 (L1), 46-56 or 50-56 or 49-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the hypervariable region residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO93/1161; and Hollinger et al., Proc. Natl. Acad. Sci. USA 90: 6444-6448 (1993).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody", as used herein, is an antibody which mimics at least one of the functional activities of a polypeptide of interest.

A "disorder" is any condition that would benefit from treatment with an antibody of the invention. This includes chronic and acute disorders or diseases including those pathological conditions which predispose the mammal to the disorder in question. Non-limiting examples of disorders to be treated herein include cancer.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" and "cancerous" generally refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

As used herein, the term "antigen" is defined as any substance capable of eliciting an immune response.

As used herein, the term "antigen specific" refers to a property of a cell population such that supply of a particular antigen, or a fragment of the antigen, results in specific cell proliferation.

The term "CD20 expressing cancer" as used herein refers to all cancers in which the cancer cells show an expression of the CD20 antigen. Preferably CD20 expressing cancer as used herein refers to lymphomas (preferably B-Cell Non- Hodgkin's lymphomas (NHL)) and lymphocytic leukemias. Such lymphomas and lymphocytic leukemias include e.g. a) follicular lymphomas, b) Small Non-Cleaved Cell Lymphomas/Burkitt's lymphoma (including endemic Burkitt's lymphoma, sporadic Burkitt's lymphoma and Non-Burkitt's lymphoma) c) marginal zone lymphomas (including extranodal marginal zone B cell lymphoma (Mucosa-associated lymphatic tissue lymphomas, MALT), nodal marginal zone B cell lymphoma and splenic marginal zone lymphoma), d) Mantle cell lymphoma (MCL), e) Large Cell Lymphoma (including B-cell diffuse large cell lymphoma (DLCL), Diffuse Mixed Cell Lymphoma, Immunoblastic Lymphoma, Primary Mediastinal B-Cell Lymphoma, Angiocentric Lymphoma-Pulmonary B-Cell Lymphoma) f) hairy cell leukemia, g) lymphocytic lymphoma, Waldenstrom's macroglobulinemia, h) acute lymphocytic leukemia (ALL), chronic lymphocytic leukemia (CLL)/small lymphocytic lymphoma (SLL), B-cell prolymphocytic leukemia, i) plasma cell neoplasms, plasma cell myeloma, multiple myeloma, plasmacytoma j) Hodgkin's disease. More preferably the CD20 expressing cancer is a B-Cell Non-Hodgkin's lymphomas (NHL). Especially the CD20 expressing cancer is a Mantle cell lymphoma (MCL), acute lymphocytic leukemia (ALL), chronic lymphocytic leukemia (CLL), B-cell diffuse large cell lymphoma (DLCL), Burkitt's lymphoma, hairy cell leukemia, follicular lymphoma, multiple myeloma, marginal zone lymphoma, post transplant lymphoproliferative disorder (PTLD), HIV associated lymphoma, Waldenstrom's macro globulinemia, or primary CNS lymphoma.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

An "individual" or a "subject" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, the vertebrate is a human.

"Mammal" for purposes of treatment refers to any animal classified as a mammal, including humans, domestic and farm animals, and zoo, sports, or pet animals, such as dogs, horses, cats, cows, etc. In certain embodiments, the mammal is human.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents the function of cells and/or causes destruction of cells. The term is intended to include radioactive isotopes (e.g., At211, I131, I125, Y90, Re186, Re188, Sm153, Bi212, P32, Pb212 and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolyticenzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1 (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

An "individual" or a "subject" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, the vertebrate is a human.

"Mammal" for purposes of treatment refers to any animal classified as a mammal, including humans, domestic and farm animals, and zoo, sports, or pet animals, such as dogs, horses, cats, cows, etc. In certain embodiments, the mammal is human.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents the function of cells and/or causes destruction of cells. The term is intended to include radioactive isotopes (e.g., At211, I131, I125, Y90, Re186, Re188, Sm153, Bi212, P32, Pb212 and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolyticenzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal See preceding definition of "treating."

Administration "in combination with" one or more further therapeutic agents includes simultaneous (concurrent) and consecutive administration in any order.

The glycosylation of recombinant proteins produced from mammalian cells in culture is an important process in ensuring the effective use of therapeutic antibodies (Goochee et al., 1991; Jenkins and Curling, 1994). Mammalian cell culture delivers a heterogeneous mixture of glycosylation patterns which do not all have the same properties. Properties like safety, efficacy and the serum half-life of therapeutic proteins can be affected by these glycosylation patterns. We have successfully addressed the glycoform heterogeneity problem by the development of a novel class of monoclonal antibodies, named "glycoantibodies".

The term "glycoantibodies" was coined by the inventor, Dr. Chi-Huey Wong, to refer to a homogeneous population of monoclonal antibodies (preferably, therapeutic monoclonal antibodies) having a single, uniformed glycoform on Fc. The individual glycoantibodies comprising the homogeneous population are identical, bind to the same epitope, and contain the same Fc glycan with a well-defined glycan structure and sequence.

Glycoantibodies may be generated from monoclonal antibodies (preferably, therapeutic monoclonal antibodies) commercially available or in the development. Monoclonal antibodies for therapeutic use can be humanized, human or chimeric.

The term "parental antibody" as used herein refers to the monoclonal antibody used to produce a glycoantibody. The parental antibodies can be obtained by cell culturing such as mammalian cell culture, *Pichia pastoris* or insect cell lines. Preferably, the parental antibodies are produced in mammalian cell culture. The parental antibodies may be FDA approved or in development.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981); each of which is incorporated herein by reference in its entirety. The term "monoclonal antibody" (abbreviated as "mAb") as used herein is not limited to antibodies produced through hybridoma technology. The term "monoclonal antibody" refers to an antibody that is derived from a single clone, including any eukaryotic, prokaryotic, or phage clone, and not the method by which it is produced. A "monoclonal antibody" may comprise, or alternatively consist of, two proteins, i.e., a heavy and a light chain.

Described herein are the functionally active glycoantibodies derived from therapeutic monoclonal antibodies by Fc glycoengineering. The glycoantibodies with optimized glycoforms exhibit more potent biological activities compared to the therapeutic monoclonal antibodies. It is contemplated that the glycoantibodies with optimized glycoforms may provide an alternative for therapeutic use.

Glycoantibodies of the invention consist of a single, uniformed glycoform (N-glycan) on Fc. In some embodiments, the N-glycan is attached to the Asn-297 of the Fc region.

The N-glycans according to the invention have a common pentasaccharide core of $Man_3GlcNAc_2$ which is also referred to as "trimannose core" or "pentasaccharide core", wherein "Man" refers to mannose, "Glc" refers to glucose, "NAc" refers to N-acetyl, and GlcNAc refers to N-acetylglucosamine.

In some embodiments, the N-glycan has a biantennary structure.

The N-glycan described herein may have intrachain substitutions comprising "bisecting" GlcNAc. When a glycan comprises a bisecting GlcNAc on the trimannose core, the structure is represented as $Man_3GlcNAc_3$. When a glycan comprises a core fucose attached to the trimannose core, the structure is represented as $Man_3GlcNAc_2(F)$. The N-glycan may comprise one or more termial sialic acids (e.g. N-acetylneuraminic acid). The structure represented as "Sia" refers to a termial sialic acid. Sialylation may occur on either the α1-3 or α1-6 arm of the biantennary structures.

In some embodiments, the N-glycan described herein comprises at least one α2-6 terminal sialic acid. In certain embodiments, the N-glycan comprises one α2-6 terminal sialic acid. In a preferred embodiment, the N-glycan comprises two α2-6 terminal sialic acids.

In some embodiments, the N-glycan described herein comprises at least one α2-3 terminal sialic acid. In certain embodiments, the N-glycan comprises one α2-3 terminal sialic acid. In a preferred embodiment, the N-glycan comprises two α2-3 terminal sialic acids.

In some embodiments, the N-glycan described herein comprises at least one galactose. In certain embodiments, the N-glycan comprises one galactose. In a preferred embodiment, the N-glycan comprises two galactoses. Preferably, the N-glycan according to the disclosure is free of core fucose.

Table 1 lists exemplary N-glycans in glycoantibodies.

TABLE 1

| GAb | Glycan structure | Glycan sequence |
|---|---|---|
| 1-101 | | $Sia_2(α2-6)Gal_2GlcNAc_2Man_3GlcNAc_2$ |
| 1-102 | | $Sia(α2-6)Gal_2GlcNAc_2Man_3GlcNAc_2$ |

TABLE 1-continued

| GAb | Glycan structure | Glycan sequence |
|---|---|---|
| 1-103 | | Sia(α2-6)GalGlcNAc$_2$Man$_3$GlcNAc$_2$ |
| 1-104 | | Gal$_2$GlcNAc$_2$Man$_3$GlcNAc$_2$ |
| 1-105 | | GalGlcNAcMan$_3$GlcNAc$_2$ |
| 1-106 | | GalGlcNAc$_2$Man$_3$GlcNAc$_2$ |
| 1-107 | | GlcNAc$_3$Man$_3$GlcNAc$_2$ |
| 1-108 | | GlcNAc$_2$Man$_3$GlcNAc$_2$ |
| 1-109 | | GlcNAcMan$_3$GlcNAc$_2$ |
| 1-110 | | GlcNAcMan$_3$GlcNAc$_2$ |

TABLE 1-continued

| GAb | Glycan structure | Glycan sequence |
|---|---|---|
| 1-111 | | Man₃GlcNAc₂ |
| 1-112 | | Sia₂(α2-6)Gal₂GlcNAc₃Man₃GlcNAc₂ |
| 1-113 | | Sia(α2-6)Gal₂GlcNAc₃Man₃GlcNAc₂ |
| 1-114 | | Sia(α2-6)GalGlcNAc₃Man₃GlcNAc₂ |
| 1-115 | | Gal₂GlcNAc₃Man₃GlcNAc₂ |
| 1-116 | | GalGlcNAc₃Man₃GlcNAc₂ |
| 1-117 | | Sia₂(α2-3)Gal₂GlcNAc₂Man₃GlcNAc₂ |
| 1-118 | | Sia(α2-3)Gal₂GlcNAc₂Man₃GlcNAc₂ |

TABLE 1-continued

| GAb | Glycan structure | Glycan sequence |
|---|---|---|
| 1-119 | | Sia$_2$(α2-3)Gal$_2$GlcNAc$_3$Man$_3$GlcNAc$_2$ |
| 1-120 | | Sia(α2-3)Gal$_2$GlcNAc$_3$Man$_3$GlcNAc$_2$ |
| 1-121 | | Sia$_2$(α2-3/α2-6)Gal$_2$GlcNAc$_3$Man$_3$GlcNAc$_2$ |
| 1-122 | | Sia$_2$(α2-6/α2-3)Gal$_2$GlcNAc$_2$Man$_3$GlcNAc$_2$ |
| 1-123 | | Sia$_2$(α2-3/α2-6)Gal$_2$GlcNAc$_3$Man$_3$GlcNAc$_2$ |
| 1-124 | | Sia$_2$(α2-6/α2-3)Gal$_2$GlcNAc$_3$Man$_3$GlcNAc$_2$ |
| 1-125 | | Sia(α2-3)GalGlcNAc$_2$Man$_3$GlcNAc$_2$ |
| 1-126 | | Sia(α2-3)GalGlcNAc$_3$Man$_3$GlcNAc$_2$ |

In some embodiments, the structure of the oligosaccharide on the antibody can include or exclude an oligosaccharide having any of the following structures:
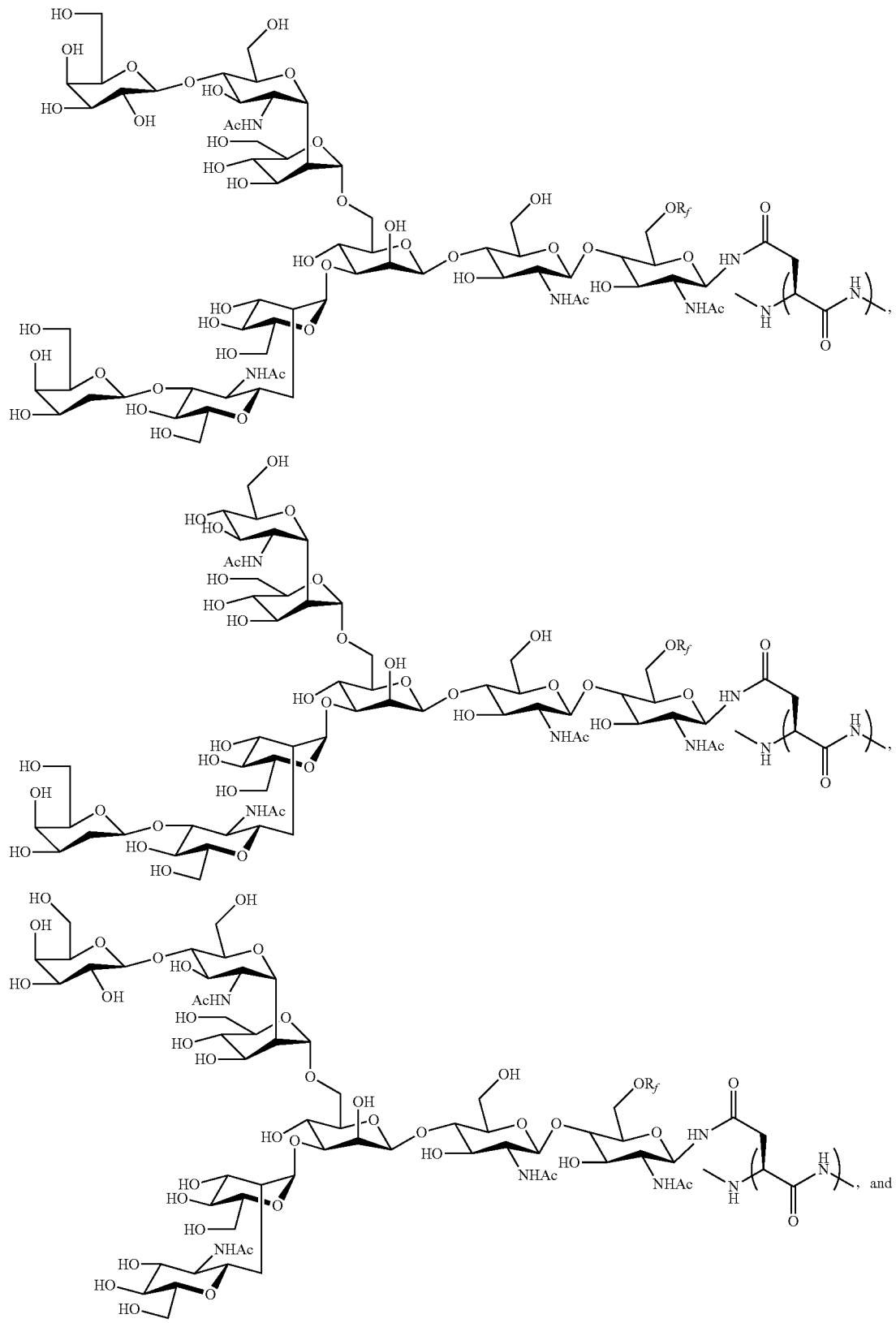

-continued
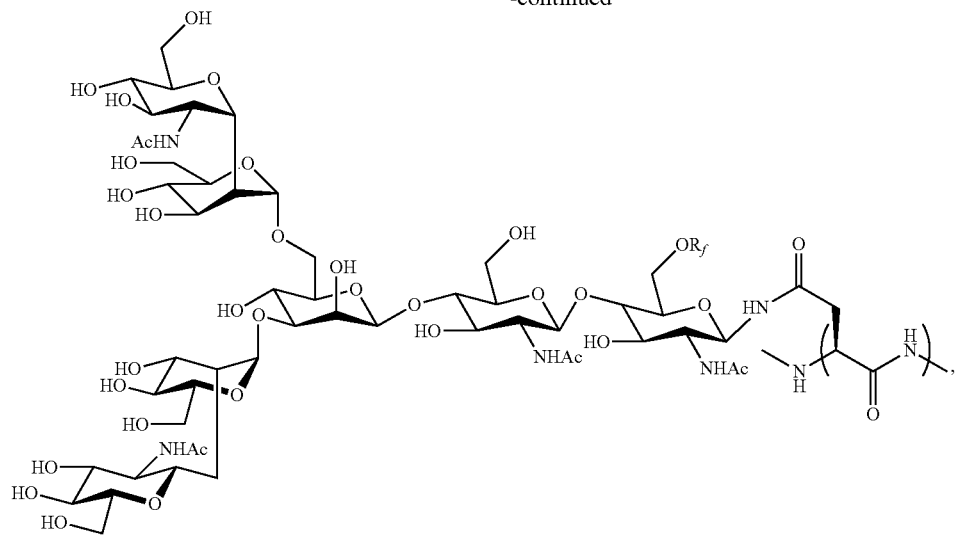
where $R_f$ is selected from H or
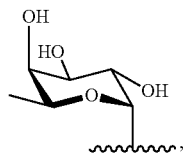
and the indicated asparagine is the Asn-297.
In some embodiments, this disclosure relates to a method comprising the steps of (a) reacting UDP galactose with an oligosaccharide having the structure:
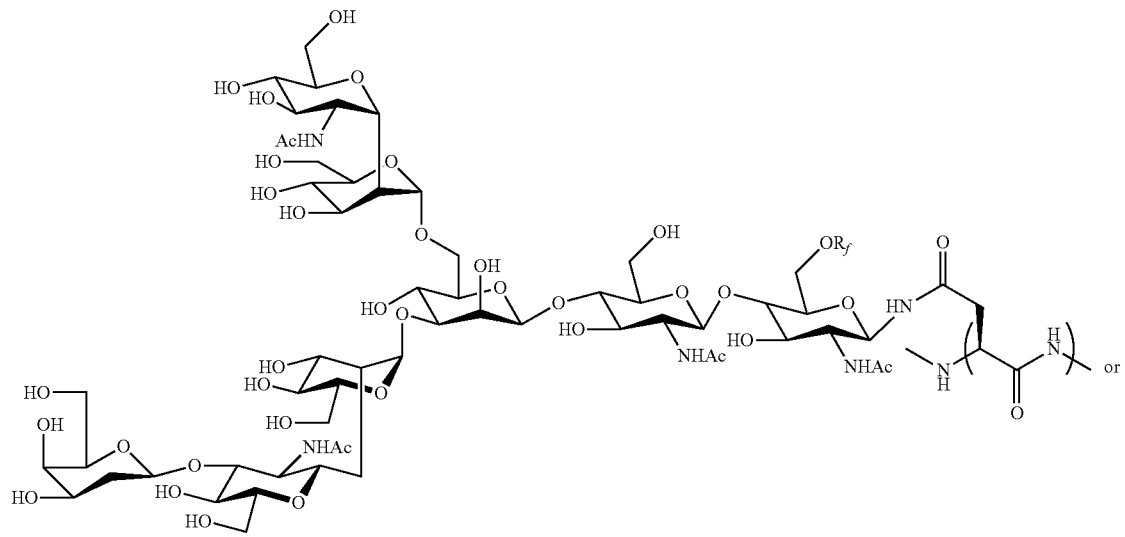

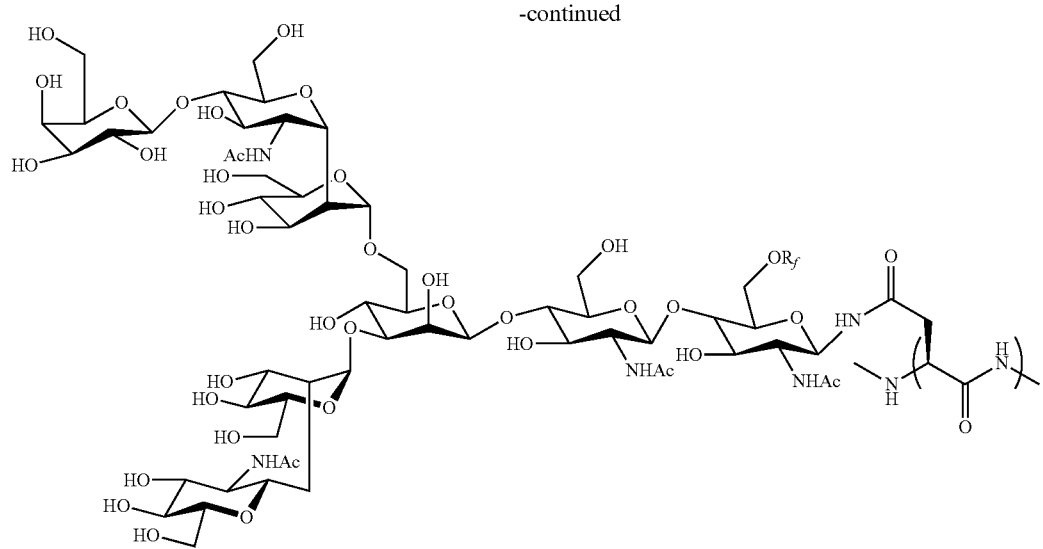
using β-1,4-galactosyltransferase as an enzymatic catalyst to form a Gal$_2$-oligosaccharide having the structure:
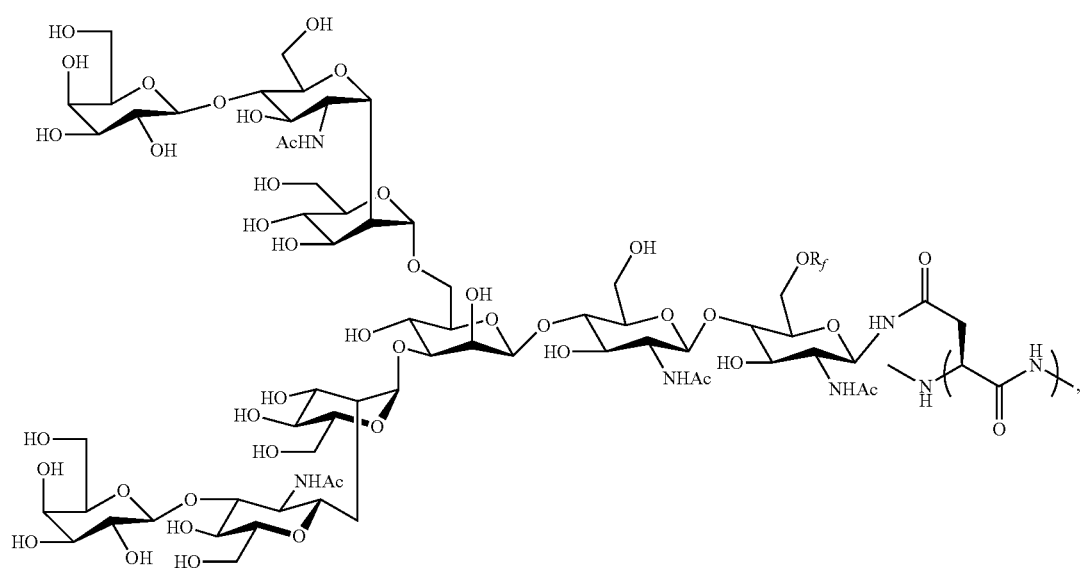

and reacting UDP galactose with an oligosaccharide having the structure:
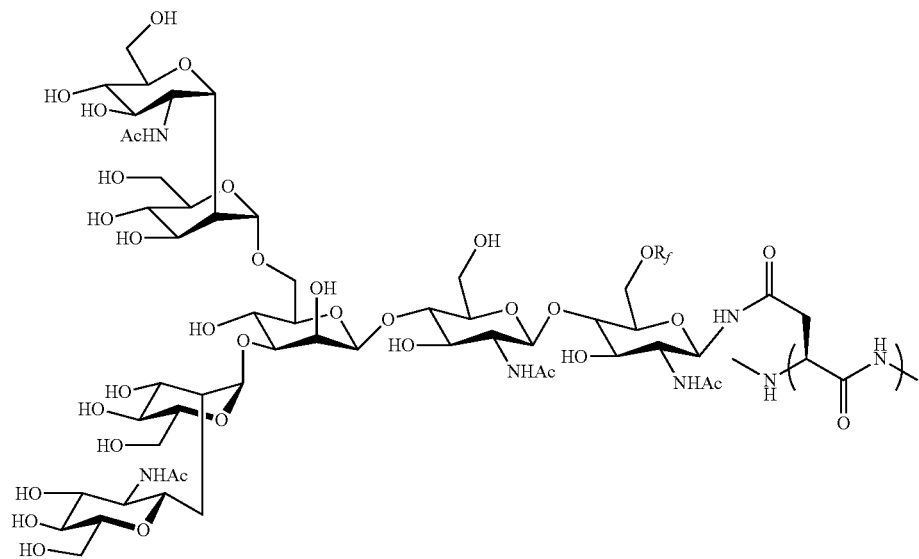
using β-1,4-galactosyltransferase as an enzymatic catalyst to form an $Gal_2$-oligosaccharide having the structure:
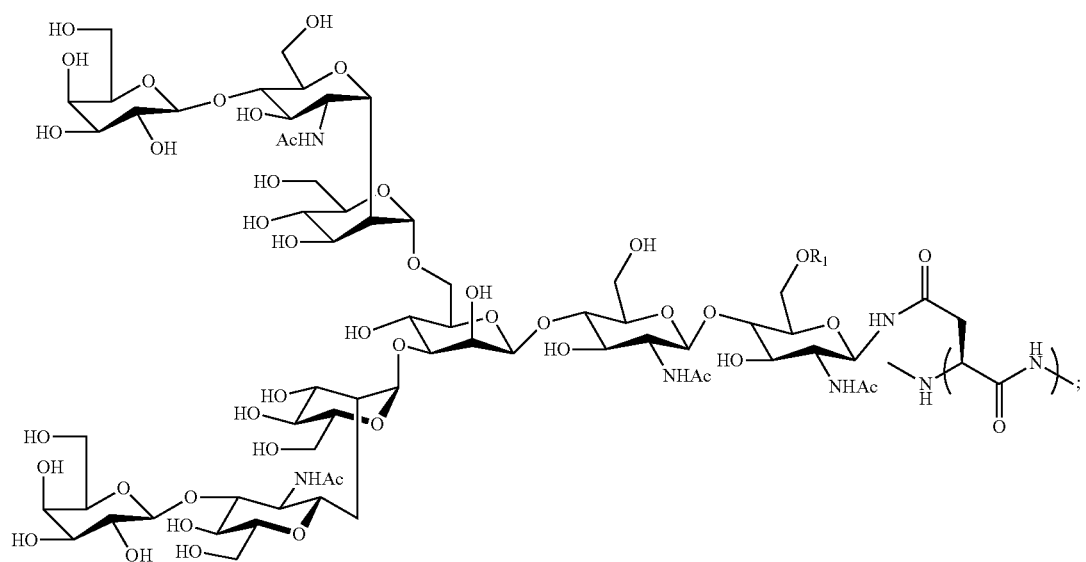

and
(b) reacting the Gal$_2$-oligosaccharide having the structure:
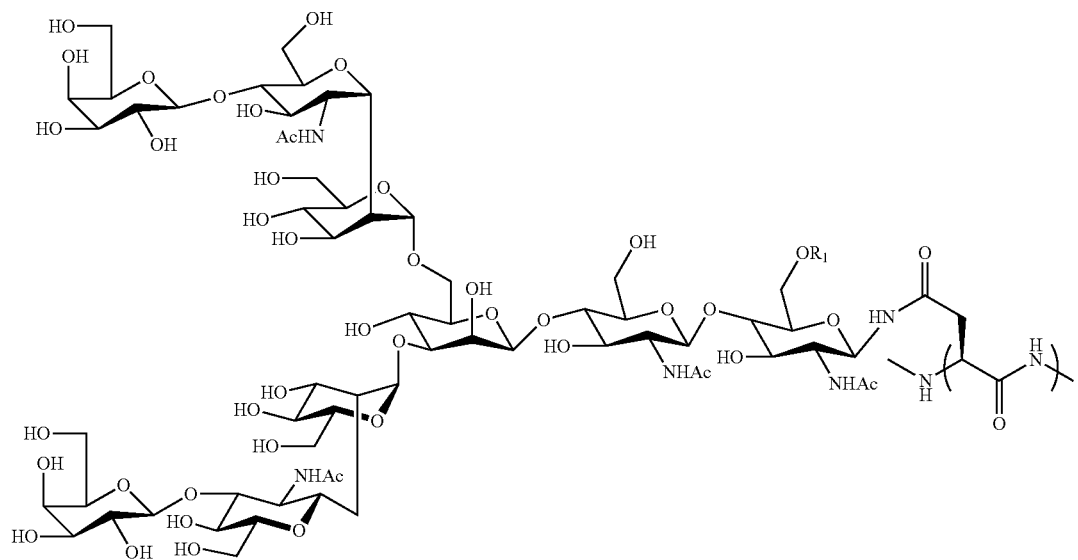
with the compound having the structure:
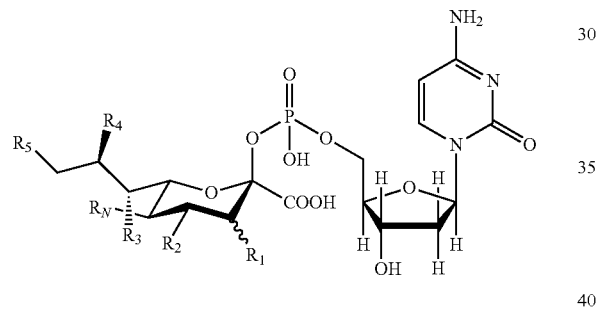
using an alpha-2,6-sialyltransferase as the enzymatic catalyst to form a glycan having the structure:
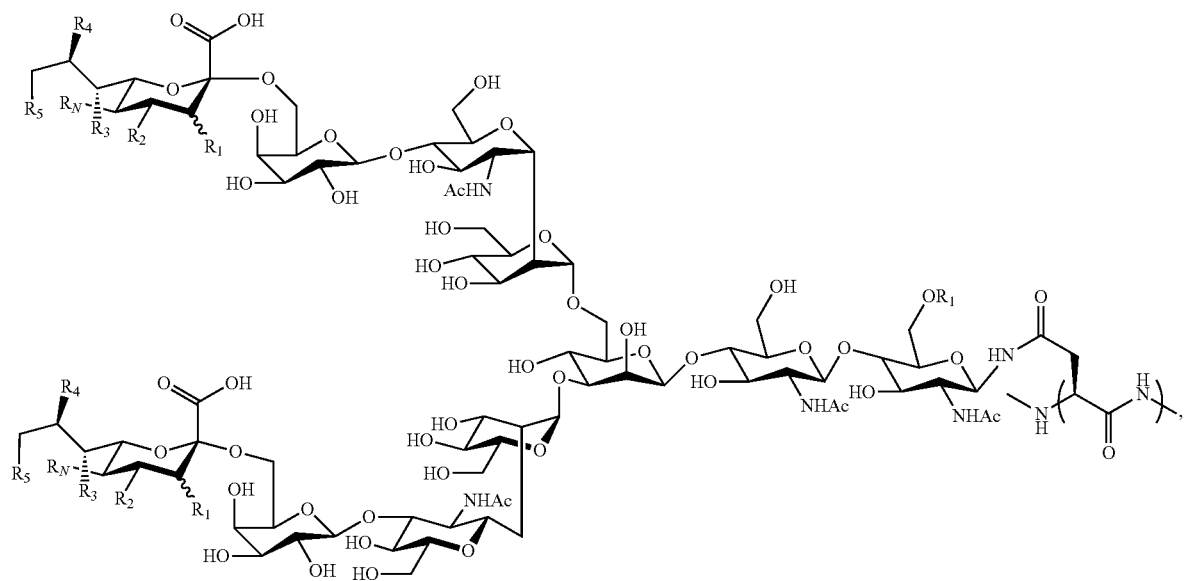

wherein:

$R_1$ is selected from hydrogen or hydroxy;

each instance of $R_2$, $R_3$, $R_4$, and $R_5$ is independently selected from hydrogen, halogen, optionally substituted alkyl, optionally substituted alkenyl, optionally substituted alkynyl, optionally substituted heterocyclyl, optionally substituted aryl, —$N_3$, —$NO_2$, —$N(R_B)_2$, —$N(R_A)C(O)R_A$, —$OR_A$, —$OC(O)R_A$, —$SR_A$, —$C(O)N(R_B)_2$, —CN, —$C(O)R_A$, —$C(O)OR_A$, —$S(O)R_A$, —$SO_2R_A$, —$SO_2N(R_B)_2$, and —$NHSO_2R_B$;

$R_N$ is selected from —$N_3$, —$NO_2$, —$N(R_B)_2$, —$N(R_A)C(O)R_A$, —$OR_A$, —$OC(O)R_A$, —$SR_A$, —$C(O)N(R_B)_2$, —CN, —$C(O)R_A$, —$C(O)OR_A$, —$S(O)R_A$, —$SO_2R_A$, —$SO_2N(R_B)_2$, and —$NHSO_2R_B$;

each instance of $R_A$ is independently selected from hydrogen, optionally substituted alkyl, optionally substituted alkenyl, optionally substituted alkynyl, optionally substituted heterocyclyl, and optionally substituted aryl; and each instance of $R_B$ is independently selected from hydrogen, optionally substituted alkyl, optionally substituted alkenyl, optionally substituted alkynyl, optionally substituted heterocyclyl, and optionally substituted aryl.

In some embodiments, this disclosure relates to a method of forming a glycan having the structure of:

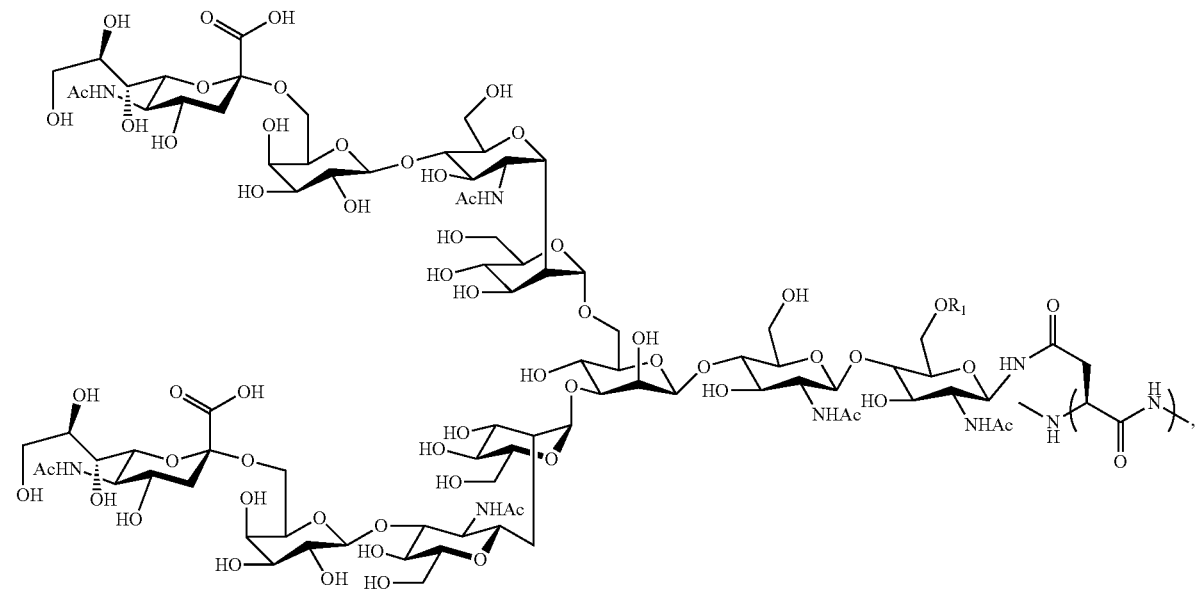

wherein $R_f$ is selected from H or

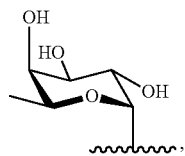

and wherein the indicated asparagine is the Asn-297.

In some embodiments, this disclosure relates to a pharmaceutical composition comprising a glycan having the structure of:

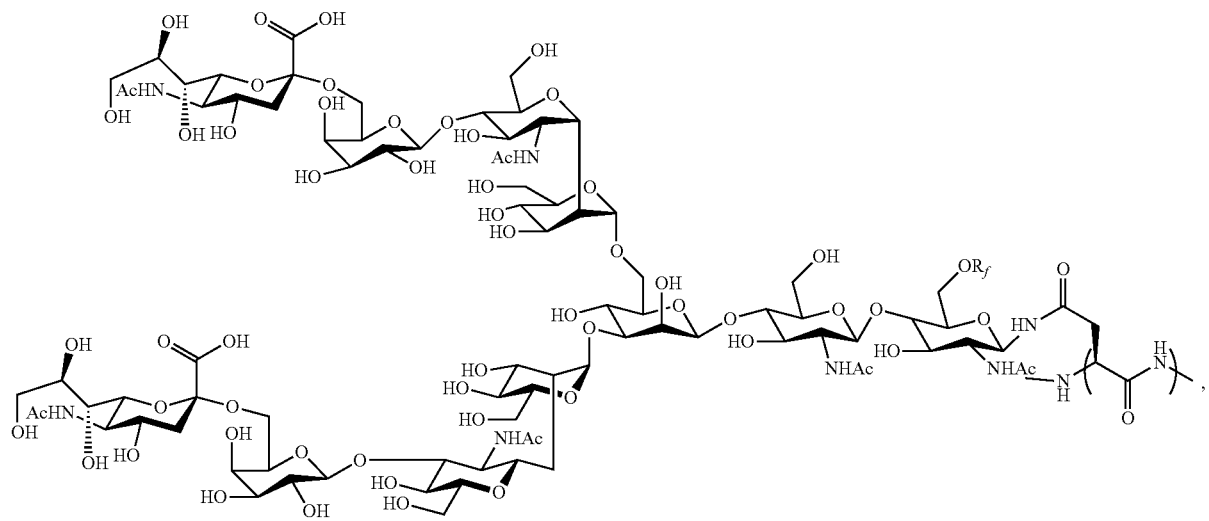

wherein $R_f$ is selected from H or

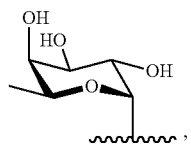

and
wherein the indicated asparagine is the Asn-297.

Glycosylation on Fc can affect a variety of immunoglobulin effector-mediated functions, including ADCC, CDC and circulating half-life. ADCC enhancement is a key strategy for improving therapeutic antibody drug efficacy. It has the potential of lowering effective drug dosage for benefits of lower drug cost. The glycoantibodies described herein can be characterized by functional properties. Glycoantibodies described herein may be useful for treating a cancer. The FDA has approved multiple therapeutic monoclonal antibodies for cancer therapies, and many more are being studied in clinical trials either alone or in combination with other treatments. These monoclonal antibodies ("parental antibodies") can be used to produce glycoantibodies.

Exemplary monoclonal antibodies for cancers include, but are not limited to, Ado-trastuzumab emtansine (Kadcyla), Alemtuzumab (Campath), Belimumab (Benlysta), Bevacizumab (Avastin), Brentuximab vedotin (Adcetris), Cabozantinib (Cometriq), Canakinumab (Ilaris), Cetuximab (Erbitux), Denosumab (Xgeva), Ibritumomab tiuxetan (Zevalin), Ipilimumab (Yervoy), Nivolumab (Opdivo), Obinutuzumab (Gazyva), Ofatumumab (Arzerra, HuMax-CD20), Panitumumab (Vectibix), Pembrolizumab (Keytruda), Pertuzumab (Perjeta), Ramucirumab (Cyramza), Rituximab (Rituxan, Mabthera), Siltuximab (Sylvant), Tocilizumab, Tositumomab (Bexxar) and Trastuzumab (Herceptin).

Anti-CD20 Glycoantibodies (Anti-CD20 GAb)

The "CD20" antigen is a non-glycosylated, transmembrane phosphoprotein with a molecular weight of approximately 35 kD that is found on the surface of greater than 90% of B cells from peripheral blood or lymphoid organs. CD20 is expressed during early pre-B cell development and remains until plasma cell differentiation; it is not found on human stem cells, lymphoid progenitor cells or normal plasma cells. CD20 is present on both normal B cells as well as malignant B cells. Other names for CD20 in the literature include "B-lymphocyte-restricted differentiation antigen" and "Bp35". The CD20 antigen is described in, for example, Clark and Ledbetter, Adv. Can Res. 52:81-149 (1989) and Valentine et al. J. Biol. Chem. 264(19):11282-11287 (1989).

The present disclosure features a novel class of anti-CD20 antibodies, termed "anti-CD20 glycoantibodies" ("anti-CD20 GAb"). The anti-CD20 glycoantibodies can be generated from anti-CD20 monoclonal antibodies by Fc glycoengineering. The individual anti-CD20 glycoantibodies comprising the homogeneous population are identical and contain the same Fc glycan with a well-defined glycan structure and sequence. The anti-CD20 GAb according to the present invention specifically binds to the same epitope of a human CD20 antigen on a cell membrane as its patent antibody.

The term "parental antibody" as used herein refers to the anti-CD20 monoclonal antibody used to produce an anti-CD20 glycoantibody.

The parental antibodies can be obtained by cell culturing such as mammalian cell culture, Pichia pastoris or insect cell lines. Preferrably, the parental antibodies are produced in mammalian cell culture. The parental antibodies may be FDA approved or in development. Exemplary parental antibodies include, but not limited to, Rituximab, Ofatumumab, Tositumomab, Ocrelizumab, 11B8 or 7D8 (disclosed in WO2004/035607), an anti-CD20 antibody disclosed in WO 2005/103081 such as C6, an anti-CD antibody disclosed in WO2003/68821 such as IMMU-106 (from Immunomedics), an anti-CD20 antibody disclosed in WO2004/103404 such as AME-133 (from Applied Molecular Evolution/Lilly), and anti-CD20 antibody disclosed in US 2003/0118592 such as TRU-015 (from Trubion Pharmaceuticals Inc), 90Y-labeled 2B8 murine antibody designated "Y2B8" (ZEVALIN®) (Biogen-Idec, Inc.) (e.g., U.S. Pat. No. 5,736,137, Anderson et al.; ATCC deposit HB11388); murine and chimeric 2H7 antibody (e.g., U.S. Pat. No. 5,677,180, Robinson et al.); humanized 2H7 antibodies such as rhuMAb2H7 and other versions (Genentech, Inc.) (e.g., WO 2004/056312, Adams et al., and other references noted below); human monoclonal antibodies against CD20 (GenMab A/S/Medarex, Inc.) (e.g., WO 2004/035607 and WO 2005/103081, Teeling et al.); a chimerized or humanized monoclonal antibody binding to an extracellular epitope of CD20 (Biomedics Inc.) (e.g., WO 2006/106959, Numazaki et al.); humanized LL2 and similar antibodies (Immunomedics, Inc.) (e.g., U.S. Pat. No. 7,151, 164 and US 2005/0106108, Hansen); A20 antibodies (Immunomedics, Inc.) such as chimeric A20 (cA20) or humanized A20 antibody (hA20, IMMUN-106T, veltuzumab) (e.g., US 2003/0219433, Hansen et al.); fully human antibodies against CD20 (Amgen/AstraZeneca) (e.g., WO 2006/130458, Gazit et al.); antibodies against CD20 (Avestha Gengraine Technologies Pvt Ltd.) (e.g., WO 2006/126069, Morawala); and chimeric or humanized B-Ly1 antibodies to CD20 (Roche/GlycArt Biotechnology AG) such as GA101 (e.g., WO 2005/044859; US 2005/0123546; US 2004/0072290; and US 2003/0175884, Umana et al.).

In some embodiments, the exemplary anti-CD20 GAb described herein comprise a heavy chain having the amino acid sequence set forth in SEQ ID NO: 2, and a light chain having the amino acid sequence set forth in SEQ ID NO: 1 as shown in FIG. 9.

In some embodiments, the N-glycan is attached to the Asn-297 of the Fc region.

The N-glycans according to the invention have a common pentasaccharide core of $Man_3GlcNAc_2$ which is also referred to as "trimannose core" or "pentasaccharide core", wherein "Man" refers to mannose, "Glc" refers to glucose, "NAc" refers to N-acetyl, and GlcNAc refers to N-acetylglucosamine.

In some embodiments, the N-glycan has a biantennary structure.

The N-glycan described herein may have intrachain substitutions comprising "bisecting" GlcNAc. When a glycan comprises a bisecting GlcNAc on the trimannose core, the structure is represented as $Man_3GlcNAc_3$. When a glycan comprises a core fucose attached to the trimannose core, the structure is represented as $Man_3GlcNAc_2(F)$. The N-glycan may comprise one or more termial sialic acids (e.g. N-acetylneuraminic acid). The structure represented as "Sia" refers to a termial sialic acid. Sialylation may occur on either the α1-3 or α1-6 arm of the biantennary structures.

In some embodiments, the N-glycan described herein comprises at least one α2-6 terminal sialic acid. In certain embodiments, the N-glycan comprises one α2-6 terminal sialic acid. In a preferred embodiment, the N-glycan comprises two α2-6 terminal sialic acids.

In some embodiments, the N-glycan described herein comprises at least one α2-3 terminal sialic acid. In certain embodiments, the N-glycan comprises one α2-3 terminal sialic acid. In a preferred embodiment, the N-glycan comprises two α2-3 terminal sialic acids.

In some embodiments, the N-glycan described herein comprises at least one galactose. In certain embodiments, the N-glycan comprises one galactose. In a preferred embodiment, the N-glycan comprises two galactoses.

The N-glycan disclosed herein can include or exclude a core fucose. In some embodiments, the N-glycan according to the disclosure is free of core fucose. In some embodiments, the N-glycan according to the disclosure includes a core fucose.

The HER2 gene is overexpressed or amplified in approximately 30% of breast cancers. Breast cancer patients with HER2 overexpression or amplification have shortened disease-free and overall survivals. The HER2 protein is thought to be a unique and useful target for antibody therapy of cancers overexpressing the HER2 gene. A monoclonal antibody anti-HER2, Trastuzumab (Herceptin®), has been successfully used in therapy for malignant cancers relating to this target, which was approved by FDA in 1998 for the treatment of HER2 overexpressing breast cancer. A need remains for improved therapeutic antibodies against HER2 which are more effective in preventing and/or treating a range of diseases involving cells expressing HER2, including but not limited breast cancer.

The present disclosure features a novel class of anti-HER2 antibodies, termed "anti-HER2 glycoantibodies" ("anti-HER2 GAb"). The anti-HER2 glycoantibodies can be generated from anti-HER2 monoclonal antibodies by Fc glycoengineering. The individual anti-HER2 glycoantibodies comprising the homogeneous population are identical and contain the same Fc glycan with a well-defined glycan structure and sequence. The anti-HER2 GAb according to the present invention specifically binds to the same epitope of a human HER2 antigen as its patent antibody.

The term "parental antibody" as used herein refers to the anti-HER2 monoclonal antibody used to produce an anti-HER2 glycoantibody.

The parental antibodies can be obtained by cell culturing such as mammalian cell culture, *Pichia pastoris* or insect cell lines. Preferably, the parental antibodies are produced in mammalian cell culture. The parental antibodies may be FDA approved or in development. FDA approved anti-HER2 therapeutic antibodies include Trastuzumab (Herceptin), Lapatinib (Tykerb), Pertuzumab (Perjeta), Ado-trastuzumab emtansine (Kadcyla, Genentech).

Glycoantibodies described herein may be useful for treating an autoimmunity and/or inflammation. Exemplary monoclonal antibodies for autoimmunity and inflammation include, but are not limited to, Natalizumab (Tysabri; Biogen Idec/Elan), Vedolizumab (MLN2; Millennium Pharmaceuticals/Takeda), Belimumab (Benlysta; Human Genome Sciences/GlaxoSmithKline), Atacicept (TACI-Ig; Merck/Serono), Alefacept (Amevive; Astellas), Otelixizumab (TRX4; Tolerx/GlaxoSmithKline), Teplizumab (MGA031; MacroGenics/Eli Lilly), Rituximab (Rituxan/Mabthera; Genentech/Roche/Biogen Idec), Ofatumumab (Arzerra; Genmab/GlaxoSmithKline), Ocrelizumab (2H7; Genentech/Roche/Biogen Idec), Epratuzumab (hLL2; Immunomedics/UCB), Alemtuzumab (Campath/MabCampath; Genzyme/Bayer), Abatacept (Orencia; Bristol-Myers Squibb), Eculizumab (Soliris; Alexion pharmaceuticals), Omalizumab (Xolair; Genentech/Roche/Novartis), Canakinumab (Ilaris; Novartis), Mepolizumab (Bosatria; GlaxoSmithKline), Reslizumab (SCH55700; Ception Therapeutics), Tocilizumab (Actemra/RoActemra; Chugai/Roche), Ustekinumab (Stelara; Centocor), Briakinumab (ABT-874; Abbott), Etanercept (Enbrel; Amgen/Pfizer), Infliximab (Remicade; Centocor/Merck), Adalimumab (Humira/Trudexa; Abbott), Certolizumab pegol (Cimzia; UCB), and Golimumab (Simponi; Centocor).

Monocytes and macrophages secrete cytokines known as tumor necrosis factor-α (TNFα) and tumor necrosis factor-β (TNFβ) in response to endotoxin or other stimuli. TNFα is a soluble homotrimer of 17 kD protein subunits (Smith, et al., J. Biol. Chem. 262:6951-6954 (1987)). A membrane-bound 26 kD precursor form of TNF also exists (Kriegler, et al., Cell 53:45-53 (1988)). TNF-α is a potent inducer of the inflammatory response, a key regulator of innate immunity and plays an important role in the regulation of Th1 immune responses against intracellular bacteria and certain viral infections. However, dysregulated TNF can also contribute to numerous pathological situations. These include immune-mediated inflammatory diseases (IMIDs) including rheumatoid arthritis, Crohn's disease, psoriatic arthritis, ankylosing spondylitis, ulcerative colitis and severe chronic plaque psoriasis.

The present disclosure features a novel class of anti-TNFα monoclonal antibodies, termed "anti-TNFα glycoantibodies" ("anti-TNFα GAbs"). Anti-TNFα glycoantibodies can be generated from anti-TNFα monoclonal antibodies ("parental antibodies") by Fc glycoengineering. The term "parental antibodies" as used herein refers to the anti-TNFα monoclonal antibodies used to produce anti-TNFα glycoantibodies. The individual anti-TNFα glycoantibodies comprising the homogeneous population are identical and contain the same Fc glycan with a well-defined glycan structure and sequence. Anti-TNFα glycoantibodies of the invention may bind to the same epitope of a human TNFα antigen as its patental antibodies do.

The parental antibodies may be produced in cells such as mammalian cells, *Pichia pastoris* or insect cells. Preferably, the parental antibodies are produced in mammalian cells. The parental antibodies may be FDA approved or in development. Anti-TNFα monoclonal antibodies approved or in development include Infliximab, Adalimumab, Golimumab, CDP870 (certolizumab), TNF-TeAb and CDP571.

In some embodiments, glycoantibodies described herein are useful for treating an infectious disease.

Exemplary monoclonal antibodies for infectious disease include, but are not limited to, anti-Ebola antibodies suc as MB-003 (c13C6, h13F6 and c6D8), ZMab (m1H3, m2G4 and m4G7) and ZMapp (c13C6, c2G4, c4G7), anti-HIV antibodies such as VRC01, VRC02, VRC03, VRC06, b12, HJ16, 8ANC131, 8ANC134, CH103, NIH45, NIH46, NIH45G54W, NIH46G54W, 3BNC117, 3BNC60, VRC-PG04, 1NC9, 12A12, 12A21, VRC23, PG9, PGT145, PGDM1400, PG16, 2G12, PGT121, PGT128, PGT135, 4E10, 10E8, Z13 and 2F5, and anti-influenza antibodies such as C179, CR6261, F10, FI6, CR8020, CH65, C05, TCN-032, D005, CR9114 and S139/1.

In some embodiments, the present disclosure features a novel class of glycoengineered FI6 monoclonal antibodies. F16 monoclonal antibodies are neutralizing anti-influenza A virus antibodies. The neutralizing antibodies response to Influenza A virus. Amino acid sequences of a heavy chain and a lights of the antibodies are as those described in PCT publication WO 2013011347.

The pharmaceutical composition according to the disclosure may be used in therapeutics. For example, the pharmaceutical composition can be used for preventing, treating, or ameliorating one or more symptoms associated with a disease, disorder, or infection where an enhanced efficacy of effector cell function (e.g., ADCC) mediated by FcγR is desired, e.g., cancer, autoimmune, infectious disease, and in enhancing the therapeutic efficacy of therapeutic antibodies the effect of which is mediated by ADCC.

After preparation of the antibodies as described herein, a "pre-lyophilized formulation" can be produced. The antibody for preparing the formulation is preferably essentially pure (i.e. free from contaminating proteins etc) and desirably essentially homogeneous (i.e. heterogeneously glycosylated). "Essentially pure" protein means a composition comprising at least about 90% by weight of the specific protein, based on total weight of the composition, preferably at least about 95% by weight. An "essentially homogeneous" glycoengineered antibody means a composition comprising at least about 85% by weight of the glycoengineered antibody, including for example, at least about 85%, at least about 90%, at least about 95%, at least about 97%, at least about 98%, at least about 98.5%, at least about 99% based on total weight of the glycoengineered antibodies in the composition. In certain embodiments, the glycoengineered antibody is a structural variants, and/or antigen binding fragment thereof.

The amount of antibody in the pre-lyophilized formulation is determined taking into account the desired dose volumes, mode(s) of administration etc. Where the protein of choice is an intact antibody (a full-length antibody), from about 2 mg/mL to about 50 mg/mL, preferably from about 5 mg/mL to about 40 mg/mL and most preferably from about 20-30 mg/mL is an exemplary starting protein concentration. The protein is generally present in solution. For example, the protein may be present in a pH-buffered solution at a pH from about 4-8, and preferably from about 5-7. Exemplary buffers include histidine, phosphate, Tris, citrate, succinate and other organic acids. The buffer concentration can be from about 1 mM to about 20 mM, or from about 3 mM to about 15 mM, depending, for example, on the buffer and the desired isotonicity of the formulation (e.g. of the reconstituted formulation). The preferred buffer is histidine in that, as demonstrated below, this can have lyoprotective properties. Succinate was shown to be another useful buffer.

The lyoprotectant is added to the pre-lyophilized formulation. In preferred embodiments, the lyoprotectant is a non-reducing sugar such as sucrose or trehalose. The amount of lyoprotectant in the pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/aggregation of the protein occurs upon lyophilization. Where the lyoprotectant is a sugar (such as sucrose or trehalose) and the protein is an antibody, exemplary lyoprotectant concentrations in the pre-lyophilized formulation are from about 10 mM to about 400 mM, and preferably from about 30 mM to about 300 mM, and most preferably from about 50 mM to about 100 mM.

The ratio of protein to lyoprotectant is selected for each protein and lyoprotectant combination. In the case of an antibody as the protein of choice and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, and preferably from about 200 to about 1000 moles of lyoprotectant to 1 mole antibody, for example from about 200 to about 600 moles of lyoprotectant to 1 mole antibody.

In preferred embodiments of the invention, it has been found to be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palnidopropyl-, or isostearamidopropyl-betaine (e.g lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68 etc). The amount of surfactant added is such that it reduces aggregation of the reconstituted protein and minimizes the formation of particulates after reconstitution. For example, the surfactant may be present in the pre-lyophilized formulation in an amount from about 0.001-0.5%, and preferably from about 0.005-0.05%.

In certain embodiments of the invention, a mixture of the lyoprotectant (such as sucrose or trehalose) and a bulking agent (e g mannitol or glycine) is used in the preparation of the pre-lyophilization formulation. The bulking agent may allow for the production of a uniform lyophilized cake without excessive pockets therein etc.

Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The pharmaceutical compositions and formulations described herein are preferably stable. A "stable" formulation/composition is one in which the antibody therein essentially retains its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes, for example.

After the protein, lyoprotectant and other optional components are mixed together, the formulation is lyophilized. Many different freeze-dryers are available for this purpose such as Hull50® (Hull, USA) or GT20® (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hrs). A secondary drying stage may be carried out at about 0-40° C., depending primarily on the type and size of container and the type of protein employed. However, it was found herein that a secondary drying step may not be necessary. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial. As a general proposition, lyophilization will result in a lyophilized formulation in which the moisture content thereof is less than about 5%, and preferably less than about 3%.

At the desired stage, typically when it is time to administer the protein to the patient, the lyophilized formulation may be reconstituted with a diluent such that the protein concentration in the reconstituted formulation is at least 50 mg/mL, for example from about 50 mg/mL to about 400 mg/mL, more preferably from about 80 mg/mL to about 300 mg/mL, and most preferably from about 90 mg/mL to about 150 mg/mL. Such high protein concentrations in the reconstituted formulation are considered to be particularly useful where subcutaneous delivery of the reconstituted formulation is intended. However, for other routes of administration, such as intravenous administration, lower concentrations of the protein in the reconstituted formulation may be desired (for example from about 5-50 mg/mL, or from about 10-40 mg/mL protein in the reconstituted formulation). In certain embodiments, the protein concentration in the reconstituted formulation is significantly higher than that in the pre-lyophilized formulation. For example, the protein concentration in the reconstituted formulation may be about 2-40 times, preferably 3-10 times and most preferably 3-6 times (e.g. at least three fold or at least four fold) that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%. Preferably, the reconstituted formulation has less than 6000 particles per vial which are >10 μm in size.

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5th Edition, John Wiley & Sons, Inc., New York, 2001; Larock, Comprehensive Organic Transformations, VCH Publishers, Inc., New York, 1989; and Carruthers, Some Modern Methods of Organic Synthesis, 3rd Edition, Cambridge University Press, Cambridge, 1987. Moreover, exemplary glycan and antibody methodologies are described in Wong et al, US20100136042, US20090317837, and US20140051127, the disclosures of each of which are hereby incorporated by reference.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, Stereochemistry of Carbon Compounds (McGraw-Hill, N Y, 1962); and Wilen, Tables of Resolving Agents and Optical Resolutions p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "C1-6" is intended to encompass C1, C2, C3, C4, C5, C6, C1-6, C1-5, C1-4, C1-3, C1-2, C2-6, C2-5, C2-4, C2-3, C3-6, C3-5, C3-4, C4-6, C4-5, and C5-6.

As used herein, the term "Alkyl" refers to a radical of a straight-chain or branched saturated hydrocarbon group having from 1 to 20 carbon atoms ("C1-20 alkyl"). In some embodiments, an alkyl group has 1 to 10 carbon atoms ("C1-10 alkyl"). In some embodiments, an alkyl group has 1 to 9 carbon atoms ("C1-9 alkyl"). In some embodiments, an alkyl group has 1 to 8 carbon atoms ("C1-8 alkyl"). In some embodiments, an alkyl group has 1 to 7 carbon atoms ("C1-7 alkyl"). In some embodiments, an alkyl group has 1 to 6 carbon atoms ("C1-6 alkyl"). In some embodiments, an alkyl group has 1 to 5 carbon atoms ("C1-5 alkyl"). In some embodiments, an alkyl group has 1 to 4 carbon atoms ("C1-4 alkyl"). In some embodiments, an alkyl group has 1 to 3 carbon atoms ("C1-3 alkyl"). In some embodiments, an alkyl group has 1 to 2 carbon atoms ("C1-2 alkyl"). In some embodiments, an alkyl group has 1 carbon atom ("C1 alkyl"). In some embodiments, an alkyl group has 2 to 6 carbon atoms ("C2-6 alkyl"). Examples of C1-6 alkyl groups include methyl (C1), ethyl (C2), n-propyl (C3), iso-propyl (C3), n-butyl (C4), tert-butyl (C4), sec-butyl (C4), iso-butyl (C4), n-pentyl (C5), 3-pentanyl (C5), amyl (C5), neopentyl (C5), 3-methyl-2-butanyl (C5), tertiary amyl (C5), and n-hexyl (C6). Additional examples of alkyl groups include n-heptyl (C7), n-octyl (C8) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted C1-10 alkyl (e.g., —CH3). In certain embodiments, the alkyl group is substituted C1-10 alkyl.

As used herein, the term "Alkenyl" refers to a radical of a straight-chain or branched hydrocarbon group having from 2 to 20 carbon atoms, one or more carbon-carbon double bonds, and no triple bonds ("C2-20 alkenyl"). In some embodiments, an alkenyl group has 2 to 10 carbon atoms ("C2-10 alkenyl"). In some embodiments, an alkenyl group has 2 to 9 carbon atoms ("C2-9 alkenyl"). In some embodiments, an alkenyl group has 2 to 8 carbon atoms ("C2-8 alkenyl"). In some embodiments, an alkenyl group has 2 to 7 carbon atoms ("C2-7 alkenyl"). In some embodiments, an alkenyl group has 2 to 6 carbon atoms ("C2-6 alkenyl"). In some embodiments, an alkenyl group has 2 to 5 carbon atoms ("C2-5 alkenyl"). In some embodiments, an alkenyl group has 2 to 4 carbon atoms ("C2-4 alkenyl"). In some embodiments, an alkenyl group has 2 to 3 carbon atoms ("C2-3 alkenyl"). In some embodiments, an alkenyl group has 2 carbon atoms ("C2 alkenyl"). The one or more carbon-carbon double bonds can be internal (such as in 2-butenyl) or terminal (such as in 1-butenyl). Examples of C2-4 alkenyl groups include ethenyl (C2), 1-propenyl (C3), 2-propenyl (C3), 1-butenyl (C4), 2-butenyl (C4), butadienyl (C4), and the like. Examples of C2-6 alkenyl groups include the aforementioned C2-4 alkenyl groups as well as pentenyl (C5), pentadienyl (C5), hexenyl (C6), and the like. Additional examples of alkenyl include heptenyl (C7), octenyl (C8), octatrienyl (C8), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted C2-10 alkenyl. In certain embodiments, the alkenyl group is substituted C2-10 alkenyl.

As used herein, the term "Alkynyl" refers to a radical of a straight-chain or branched hydrocarbon group having from 2 to 20 carbon atoms, one or more carbon-carbon triple bonds, and optionally one or more double bonds ("C2-20 alkynyl"). In some embodiments, an alkynyl group has 2 to 10 carbon atoms ("C2-10 alkynyl"). In some embodiments, an alkynyl group has 2 to 9 carbon atoms ("C2-9 alkynyl"). In some embodiments, an alkynyl group has 2 to 8 carbon atoms ("C2-8 alkynyl"). In some embodiments, an alkynyl group has 2 to 7 carbon atoms ("C2-7 alkynyl"). In some embodiments, an alkynyl group has 2 to 6 carbon atoms ("C2-6 alkynyl"). In some embodiments, an alkynyl group has 2 to 5 carbon atoms ("C2-5 alkynyl"). In some embodiments, an alkynyl group has 2 to 4 carbon atoms ("C2-4 alkynyl"). In some embodiments, an alkynyl group has 2 to 3 carbon atoms ("C2-3 alkynyl"). In some embodiments, an alkynyl group has 2 carbon atoms ("C2 alkynyl"). The one or more carbon-carbon triple bonds can be internal (such as in 2-butynyl) or terminal (such as in 1-butynyl). Examples of C2-4 alkynyl groups include, without limitation, ethynyl (C2), 1-propynyl (C3), 2-propynyl (C3), 1-butynyl (C4), 2-butynyl (C4), and the like. Examples of C2-6 alkenyl groups include the aforementioned C2-4 alkynyl groups as well as pentynyl (C5), hexynyl (C6), and the like. Additional examples of alkynyl include heptynyl (C7), octynyl (C8), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted C2-10 alkynyl. In certain embodiments, the alkynyl group is substituted C2-10 alkynyl.

As used herein, the term "Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In certain embodiments, the heteroatom is independently selected from nitrogen, sulfur, and oxygen. In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

As used herein, the term "Aryl" refers to a radical of a monocyclic or polycyclic (e.g., bicyclic or tricyclic) 4n+2 aromatic ring system (e.g., having 6,10, or 14 it electrons shared in a cyclic array) having 6-14 ring carbon atoms and zero heteroatoms in the aromatic ring system ("C6-14 aryl"). In some embodiments, an aryl group has six ring carbon atoms ("C6 aryl"; e.g., phenyl). In some embodiments, an aryl group has ten ring carbon atoms ("C10 aryl"; e.g., naphthyl such as 1-naphthyl and 2-naphthyl). In some embodiments, an aryl group has fourteen ring carbon atoms ("C14 aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C6-14 aryl. In certain embodiments, the aryl group is substituted C6-14 aryl.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

As used herein, the term "optionally substituted" refers to a substituted or unsubstituted moiety.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

As used herein, the term "halo" or "halogen" refers to fluorine (fluoro, —F), chlorine (chloro, —Cl), bromine (bromo, —Br), or iodine (iodo, —I).

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In one embodiment, the antibody will be purified (1) to greater than 95% by weight of antibody as determined by, for example, the Lowry method, and in some embodiments more than 99% by weight, (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

The term "exo-glycosylase" used herein refers to an enzyme capable of hydrolysis of glycan structure from the out most non-reducing end. Examples of suitable exoglycosylase include, but are not limited to sialidase, galactosidase, alpha-fucosidase, alpha-mannosidase. The term "endo-glycosylase" used herein refers to an enzyme capable of hydrolysis of glycan structures randomly from the inner sits of whole glycan. Examples include, but are not limited to Endo-H, Endo-F3, Endo-F2, and Endo-F1.

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

The term "isolated antibody" used herein refers to an antibody substantially free from naturally associated molecules, i.e., the naturally associated molecules constituting at most 20% by dry weight of a preparation containing the antibody. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie Blue or, preferably, silver stain. Isolated antibody includes the antibody in situ within recombinant cells since at least one component of the antibody's natural environment will not be present. Ordinarily, however, isolated antibody will be prepared by at least one purification step. Purity can be measured by any appropriate method, e.g., column chromatography, polyacrylamide gel electrophoresis, and HPLC.

A "human antibody" as used herein refers to an antibody naturally existing in humans, a functional fragment thereof, or a humanized antibody, i.e., a genetically engineered antibody a portion of which (e.g., a frame region or the Fc region) derives from a naturally-occurring human antibody.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β,β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the VL, and around about 31-35 (H1), 50-65 (H2) and 95-102 (H3) in the VH when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the VL, and 26-32 (H1), 52-56 (H2) and 95-101 (H3) in the VH when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the VL, and 27-38 (H1), 56-65 (H2) and 105-120 (H3) in the VH when numbered in accordance with the IMGT numbering system; Lefranc, M. P. et al. Nucl. Acids Res. 27:209-212 (1999), Ruiz, M. e al. Nucl. Acids Res. 28:219-221 (2000)). Optionally the antibody has symmetrical insertions at one or more of the following points 28, 36 (L1), 63, 74-75 (L2) and 123 (L3) in the VL, and 28, 36 (H1), 63, 74-75 (H2) and 123 (H3) in the VH when numbered in accordance with Honneger, A. and Plukthun, A. J. Mol. Biol. 309:657-670 (2001)).

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). The present invention provides variable domain antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332: 323-329 (1988); and Presta, Curr. Opin. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed following the method of Winter and co-workers (Jones et al., Nature, 321:522-525 (1986); Reichmann et al., Nature, 332:323-329 (1988); Verhoeyen et al., Science, 239:1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

An "intact" antibody is one that comprises an antigen-binding site as well as a CL and at least heavy chain constant domains, CH 1, CH 2 and CH 3. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH 1). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

An "antibody that inhibits the growth of infected cells" or a "growth inhibitory" antibody is one that binds to and results in measurable growth inhibition of infected cells expressing or capable of expressing an HIV1 epitope bound by an antibody. Preferred growth inhibitory antibodies inhibit growth of infected cells by greater than 20%, preferably from about 20% to about 50%, and even more preferably, by greater than 50% (e.g., from about 50% to about 100%) as compared to the appropriate control, the control typically being infected cells not treated with the antibody being tested. Growth inhibition can be measured at an antibody concentration of about 0.1 to 30 µg/ml, or about 0.5 nM to 200 nM in cell culture, where the growth inhibition is determined 1-10 days after exposure of the infected cells to the antibody. Growth inhibition of infected cells in vivo can be determined in various ways known in the art. The antibody is growth inhibitory in vivo if administration of the antibody at about 1 µg/kg to about 100 mg/kg body weight results in reduction the percent of infected cells or total number of infected cells within about 5 days to 3 months from the first administration of the antibody, preferably within about 5 to 30 days.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an infected cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., Proc. Natl. Acad. Sci. (USA) 95:652-656 (1998).

"Fc receptor" or "FcR" describes a receptor that binds to the Fc region of an antibody. In certain embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (reviewed by M. Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., Eur. J. Immunol. 24:2429-2434 (1994)).

"Human effector cells" are leukocytes that express one or more FcRs and perform effector functions. Preferably, the cells express at least FcγRIII and perform ADCC effector function. Examples of human leukocytes that mediate ADCC include PBMC, NK cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1997), may be performed.

A "mammal" for purposes of treating an infection, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal. See preceding definition of "treating."

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below.

A "growth inhibitory agent" when used herein refers to a compound or composition which inhibits growth of a cell, either in vitro or in vivo. Examples of growth inhibitory agents include agents that block cell cycle progression, such as agents that induce G1 arrest and M-phase arrest. Classic M-phase blockers include the vinca alkaloids (vincristine, vinorelbine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE™, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising CDRs and being capable of binding an antigen or HIV-infected cell.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

(2) Antibodies of the Invention

The antibodies and antibody fragments of the invention are glycosylated in their Fc regions with oligosaccharides that are (a) free of core fucoses and/or (b) include terminal sialic acids linked to galactoses. Preferably, the oligosaccharides are homogeneous. In some aspects the antibodies are human or humanized Where the Fc receptor binding protein is derived from the human IgG1 immunoglobulin or the human IgG3 immunoglobulin, the sequence of the Cγ2 domain present within the Fc receptor binding protein retains a highly-conserved N-linked glycosylation site at the asparagine (Asn, N) residue at position 297 (N297). The glycosylation of this residue has been identified as being important for mediating high affinity binding and activation of Fc receptors.

In one embodiment, the terminal sugar units of the invention are sialic acids linked to galactose. When the modified human or humanized antibodies are IgG molecules, the oligosaccharide moieties attached to the Fc regions can have the structures:

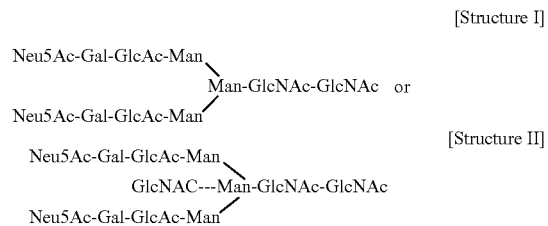

Disclosed herein is an antibody or antibody fragment in which both Ig domains comprise Fc regions that are attached to a monosaccharide moiety (e.g., N-Acetylglucosamine, GlcNAc) or a trisaccharide moiety (e.g., Mannose-N-Acetylglucosamine-N-Acetylglucosamine, Man-GlcNAc-GlcNAc).

Preferably, the trisaccharides are identical to the trisaccharide portions of the oligosaccharides attached to Fc regions of naturally-occurring human antibodies. When the antibodies are IgG molecules, the trisaccharides can have the structure of Man-GlcNAc-GlcNAc.

Any of the antibodies of this invention can be prepared from a commercially available therapeutic antibody (e.g., Reopro®, Rituxan®, Zenepax®, Simulect®, Synagis®, Remicade®, Herceptin®, Mylotarg®, Campath, Zevalin®, Humira®, Xolair®, Bexxar®, Raptiva®, Erbitux®, Avastin®, Tysabri®), human or humanized antibodies produced via a conventional method, preferably those undergoing clinical trials.

Other monoclonal antibodies suitable for this invention include, but are not limited to Cetuximab®, Rituximab®, Muromonab-CD3®, Abciximab®, Daclizumab®, Basiliximab®, Palivizumab®, Infliximab®, Trastuzumab®, Gemtuzumab Ozogamicin®, Alemtuzumab®, Ibritumomab Tiuxetan®, Adalimumab®, Omalizumab®, Tositumomab®, 1-131 Tositumomab®, Efalizumab®, Bevacizumab®, Panitumumab®, Pertuzumab®, Natalizumab®, Etanercept®, IGN101®, Volociximab®, Anti-CD80 Mab, Anti-CD23 Mab, CAT-3888®, CDP-791®, Eraptuzumab®, MDX-010®, MDX-060®, MDX-070®, Matuzumab®, CP-675®, 206®, CAL®, SGN-30®, Zanolimumab®, Adecatumumab®, Oregovomab®, Nimotuzumab®, ABT-874®, Denosumab®, AM 108®, AMG 714®, Fontolizumab®, Daclizumab®, Golimumab®, CNTO 1275®, Ocrelizumab®, Humax-CD20®, Belimumab®, Epratuzumab®, MLN1202®, Visilizumab®, Tocilizumab®, Ocrerlizumab®, Certolizumab Pegol®, Eculizumab®, Pexelizumab®, Abciximab®, Ranibizimumab®, Mepolizumab®, TNX-355®, and MYO-029®.

The antibodies of the present invention may be polyclonal or monoclonal antibodies. However, in preferred embodiments, they are monoclonal. In particular embodiments, antibodies of the present invention are human antibodies. Methods of producing polyclonal and monoclonal antibodies are known in the art and described generally, e.g., in U.S. Pat. No. 6,824,780. Typically, the antibodies of the present invention are produced by recombinant techniques, using vectors and methods available in the art, as described further below. Human antibodies may also be generated by in vitro activated B cells (see U.S. Pat. Nos. 5,567,610 and 5,229,275).

Human antibodies may also be produced in transgenic animals (e.g., mice) that are capable of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice results in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immunology, 7:33 (1993); U.S. Pat. Nos. 5,545,806, 5,569,825, 5,591,669 (all of GenPharm); U.S. Pat. No. 5,545,807; and WO 97/17852. Such animals may be genetically engineered to produce human antibodies comprising a polypeptide of the present invention.

In certain embodiments, antibodies of the present invention are chimeric antibodies that comprise sequences derived from both human and non-human sources. In particular embodiments, these chimeric antibodies are humanized or Primatized™. In practice, humanized antibodies are typically human antibodies in which some hypervariable region residues and possibly some FR residues are substituted by residues from analogous sites in rodent antibodies.

The choice of non-human sequences, both light and heavy, to be used in making the chimeric antibodies is important to reduce antigenicity and human anti-non-human antibody responses when the antibody is intended for human therapeutic use. It is further important that chimeric antibodies retain high binding affinity for the antigen and other favorable biological properties. To achieve this goal, according to a preferred method, chimeric antibodies are prepared by a process of analysis of the parental sequences and various conceptual chimeric products using three-dimensional models of the parental human and non-human sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

As noted above, antibodies (or immunoglobulins) can be divided into five different classes, based on differences in the amino acid sequences in the constant region of the heavy chains. All immunoglobulins within a given class have very similar heavy chain constant regions. These differences can be detected by sequence studies or more commonly by serological means (i.e. by the use of antibodies directed to these differences). Antibodies, or fragments thereof, of the present invention may be any class, and may, therefore, have a gamma, mu, alpha, delta, or epsilon heavy chain. A gamma chain may be gamma 1, gamma 2, gamma 3, or gamma 4; and an alpha chain may be alpha 1 or alpha 2.

In a preferred embodiment, an antibody of the present invention, or fragment thereof, is an IgG. IgG is considered the most versatile immunoglobulin, because it is capable of carrying out all of the functions of immunoglobulin molecules. IgG is the major Ig in serum, and the only class of Ig that crosses the placenta. IgG also fixes complement, although the IgG4 subclass does not. Macrophages, monocytes, PMN's and some lymphocytes have Fc receptors for the Fc region of IgG. Not all subclasses bind equally well; for example, IgG2 and IgG4 do not bind to Fc receptors. A consequence of binding to the Fc receptors on PMN's, monocytes and macrophages is that the cell can now internalize the antigen better. IgG is an opsonin that enhances phagocytosis. Binding of IgG to Fc receptors on other types of cells results in the activation of other functions. Antibodies of the present invention may be of any IgG subclass.

In another preferred embodiment, an antibody, or fragment thereof, of the present invention is an IgE. IgE is the least common serum Ig since it binds very tightly to Fc receptors on basophils and mast cells even before interacting with antigen. As a consequence of its binding to basophils and mast cells, IgE is involved in allergic reactions. Binding of the allergen to the IgE on the cells results in the release of various pharmacological mediators that result in allergic symptoms. IgE also plays a role in parasitic helminth diseases. Eosinophils have Fc receptors for IgE and binding of eosinophils to IgE-coated helminths results in killing of the parasite. IgE does not fix complement.

As noted above, the present invention further provides antibody fragments comprising a polypeptide of the present invention. In certain circumstances there are advantages of using antibody fragments, rather than whole antibodies. For example, the smaller size of the fragments allows for rapid clearance, and may lead to improved access to certain tissues, such as solid tumors. Examples of antibody fragments include: Fab, Fab', F(ab')2 and Fv fragments; diabodies; linear antibodies; single-chain antibodies; and multispecific antibodies formed from antibody fragments.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells.

In certain embodiments, antibodies of the present invention are bispecific or multi-specific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-HIV1 arm may be combined with an arm that binds to a triggering molecule on a leukocyte, such as a T-cell receptor molecule (e.g., CD3), or Fc receptors for IgG (Fc☐R), such as Fc☐RI (CD64), Fc☐RII (CD32) and Fc☐RIII (CD16), so as to focus and localize cellular defense mechanisms to the infected cell. Bispecific antibodies may also be used to localize cytotoxic agents to infected cells. These antibodies possess an HIV1-binding arm and an arm that binds the cytotoxic agent (e.g., saporin, anti-interferon-□, vinca alkaloid, ricin A chain, methotrexate or radioactive isotope hapten). Bispecific antibodies can be prepared as full length antibodies or antibody fragments (e.g., F(ab')2 bispecific antibodies). WO 96/16673 describes a bispecific anti-ErbB2/anti-Fc□RIII antibody and U.S. Pat. No. 5,837,234 discloses a bispecific anti-ErbB2/anti-Fc□RI antibody. A bispecific anti-ErbB2/Fc□ antibody is shown in WO98/02463. U.S. Pat. No. 5,821,337 teaches a bispecific anti-ErbB2/anti-CD3 antibody.

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, CH2, and CH3 regions. It is preferred to have the first heavy-chain constant region (CH1) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Antibodies with more than two valencies are contemplated. For example, trispecific antibodies can be prepared. Tutt et al., J. Immunol. 147: 60 (1991). A multivalent antibody may be internalized (and/or catabolized) faster than a bivalent antibody by a cell expressing an antigen to which the antibodies bind. The antibodies of the present invention can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain. Antibodies of the present invention further include single chain antibodies.

Methods for preparing any of the human antibodies described above are disclosed.

In one example, this method includes (i) providing a human antibody, which is glycosylated in the Fc region; and (ii) contacting the antibody with alpha-fucosidase, alpha-2,6-sialyltransferase, and optionally β-1,4-galactosyltransferase to modify the oligosaccharides contained in the antibody, thereby producing a human antibody of this invention. When both β-1,4-galactosyltransferase and alpha-2,6-sialyltransferase are used, the antibody to be modified must first contact with the β-1,4-galactosyltransferase and then the alpha-2,6-sialyltransferase. Alpha-2,6-sialyltransferase and β-galactosyltransferase transfer a sialic acid and a galactose, respectively, to an oligosaccharide via a glycosidic bond. In one example, the alpha-fucosidase and one of the β-1,4-galactosyltransferase and alpha-2,6-sialyltransferase can be immobilized on a support member (e.g., a bead). FIG. 1 shows a schematic illustration depicting the pathway (Path A).

Figure 2:
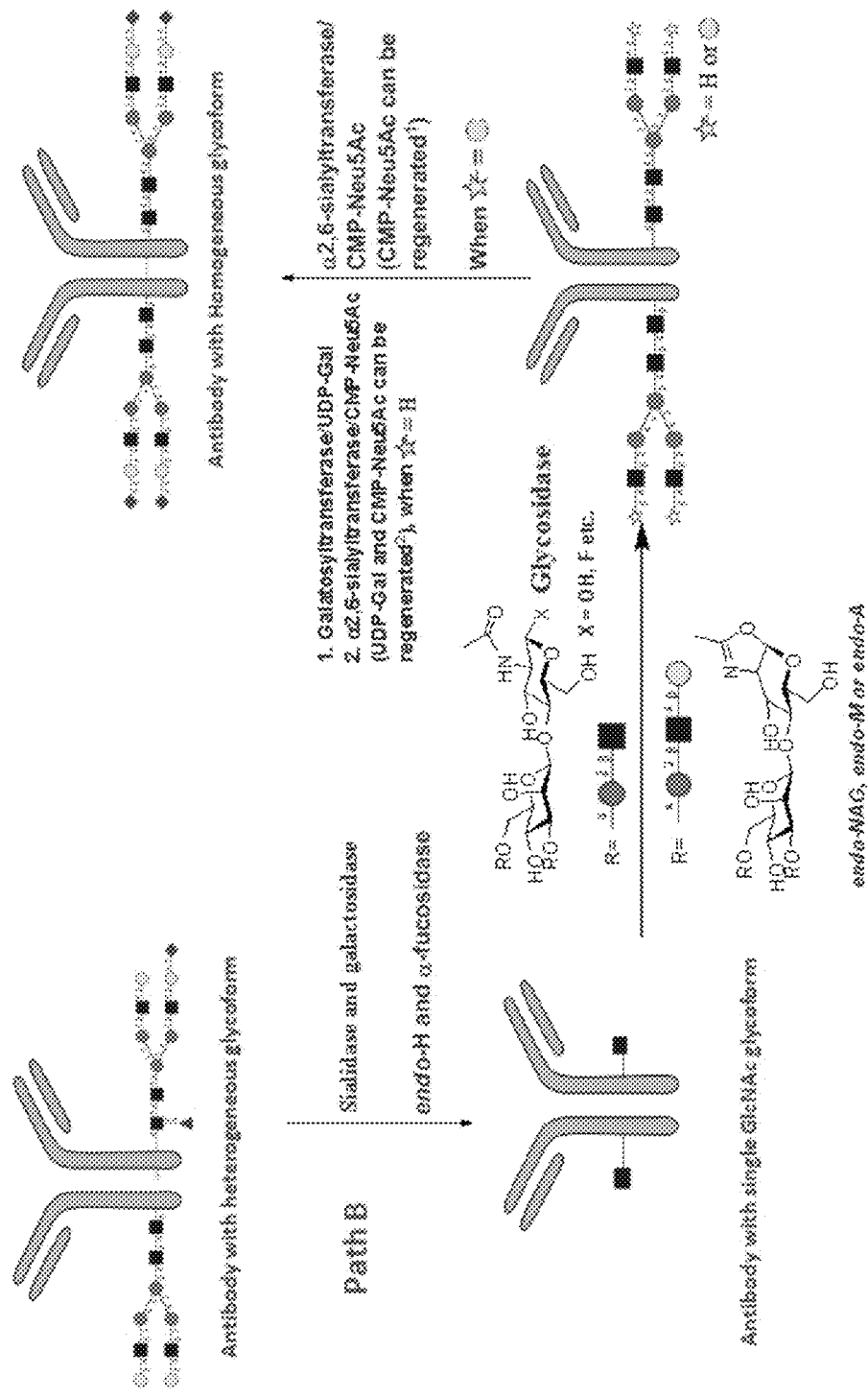
FIG. 2 shows a schematic illustration depicting a chemoenzymatic pathway (Path B) for preparing human antibodies in a single glycoform by glycan engineering, using various exo-glycosidases, endo-glycosidases, and glycosyltransferases.

FIG. 2 shows a schematic illustration depicting a chemoenzymatic pathway (Path B) for preparing human antibodies with a single glycoform by glycan engineering, using various exo-glycosidases, endo-glycosidases, and glycosyltransferases. The method the method comprises: (i) providing a Fc region of an antibody or antibody fragment, wherein the Fc region is glycosylated with an oligosaccharide; (ii) contacting the Fc region with an endo-glycosylase (such as endo-H, endo-F3, etc.) and an exo-glycosylase (such as sialidase, galactosidase, alpha-fucosidase, or a mixture thereof) under conditions wherein the oligosaccharide is digested to a single sugar unit (such as GlcNAc); (iii) elongating the single sugar unit to an oligosaccharide by glycosylation mediated by one or more glycosyltransferases such as endo-N-acetylglucosaminidase, endo-M or endo-A; and (iv) contacting the oligosaccharide with alpha-2,6-sialyltransferase to add a terminal sialic acid, thereby yielding the antibody having homogeneous oligosaccharides.

The oligosaccharide obtained from the elongating step can have a sugar sequence identical to at least a portion of an oligosaccharide found in a naturally-occurring antibody, i.e., a whole Ig molecule produced in a cell (either in cell culture or in a host animal) that glycosylates the Ig molecule in its Fc region. When the antibody is an IgG, the oligosaccharide can have the structure of:

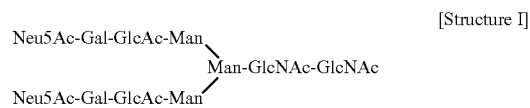

[Structure I]

In yet another example, the method of this invention comprises five steps: (i) providing a Fc region of an antibody or antibody fragment, wherein the Fc region is glycosylated with an oligosaccharide; (ii) contacting the Fc region with an endo-glycosylase (e.g., endo-H, endo-F3, etc.) and an exo-glycosylase (e.g., sialidase, galactosidase, alpha-fucosidase, or a mixture thereof) under conditions wherein the oligosaccharide is digested to a single sugar unit (e.g., GlcNAc); (iii) elongating the single sugar unit to a first oligosaccharide via glycosylation mediated by glycosyltransferases such as endo-N-acetylglucosaminidase, endo-M or endo-A; (iv) contacting the first oligosaccharide with a β-1,4-galactosyltransferase to produce a second oligosaccharide having a terminal galactose, and (v) contacting the second oligosaccharide with alpha-2,6-sialytransferase to add a terminal sialic acid, thereby yielding antibody populations having Fc regions glycosylated with homogeneous oligosaccharides.

Figure 3:
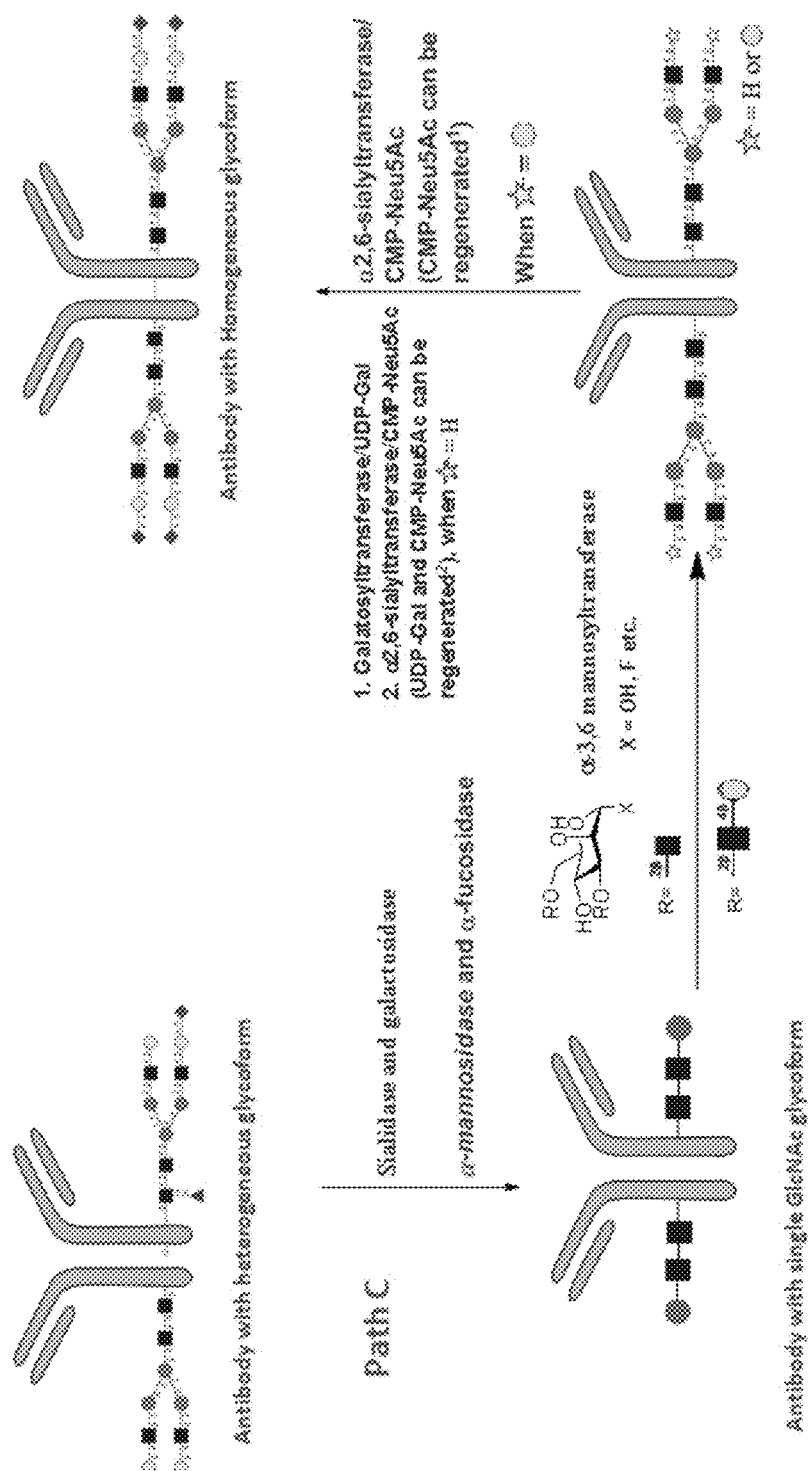
FIG. 3 shows a schematic illustration depicting an enzymatic pathway (Path C) for preparing human antibodies in a single glycoform by glycan engineering, using various exo-glycosidases and glycosyltransferases.
Figure 4:
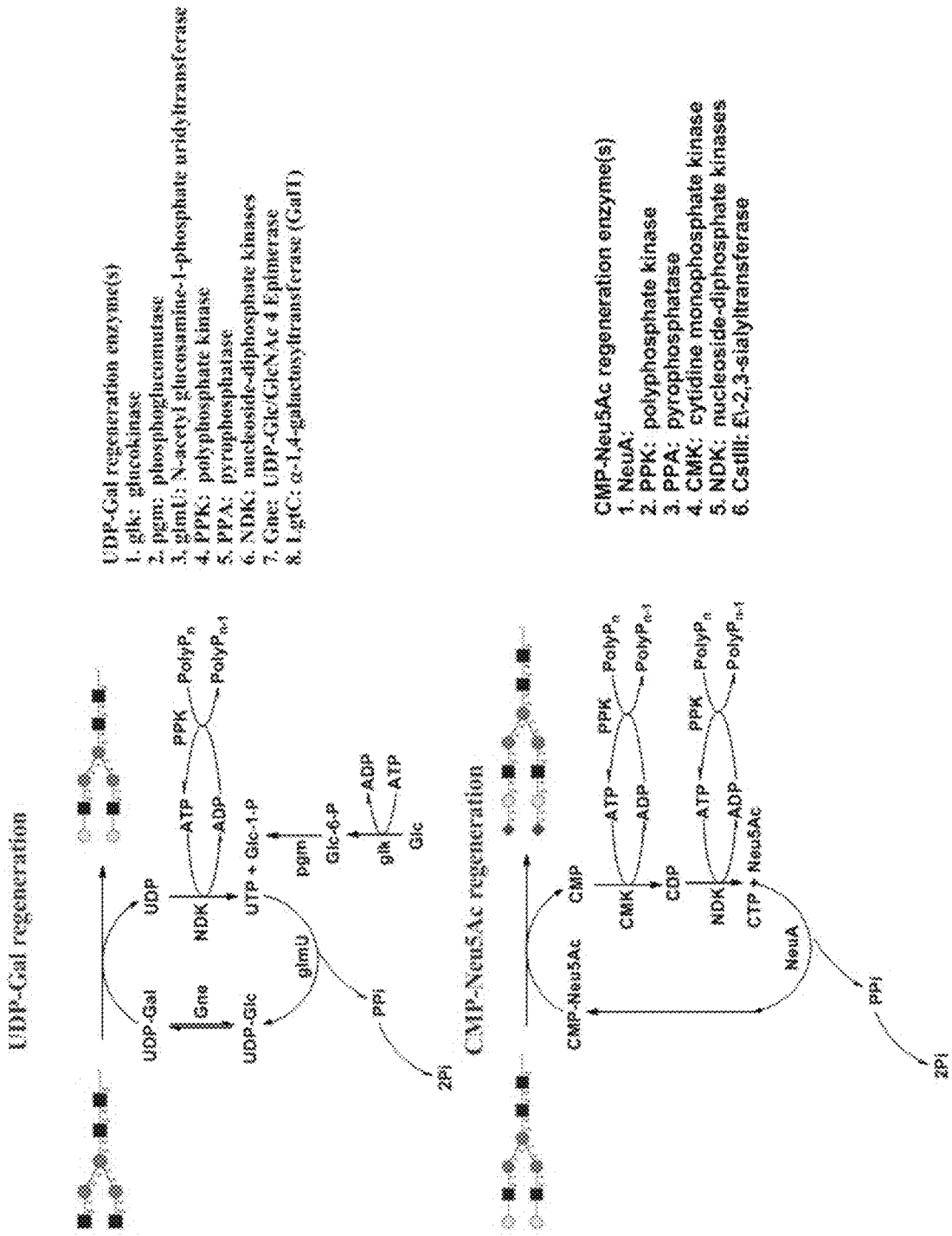
FIG. 4 shows a schematic illustration depicting the regeneration of the cofactor CMP-Neu5Ac and UDP-galactose.

In still another example, the method of this invention is performed as follows: (i) providing a human antibody, the Fc region of which is attached to oligosaccharides; (ii) treating the antibody with an exo-glycosylase (e.g., alpha-mannosidase, alpha-fucosidase, sialidase, galactosidase, or a mixture thereof) to trim each of the oligosaccharides to a trisaccharide (e.g., ManGlcNAcGlcNAc); (iii) elongating the trisaccharide to an oligosaccharide via glycosylation; and (iv) treating the oligosaccharide with alpha-2,6-sialytransferase to add terminal sialic acids, thereby yielding the antibody in a single glycoform. FIG. 3 shows a schematic illustration depicting such an enzymatic pathway (Path C).

Preferably, the oligosaccharide obtained from the elongating step has a sugar sequence identical to a portion of an oligosaccharide found in the Fc region of a naturally occurring human antibody. When the antibody is an IgG, the oligosaccharide can have the structure of:

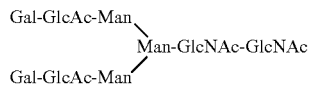

The oligosaccharide is then subjected to alpha-2,6-sialytransferase treatment to add terminal sialic acid residues.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1: Method a for Making Antibodies of the Invention

Following Path A depicted in FIG. 1, a human antibody can be treated with α-fucosidase to remove core fucoses and with α-2,6-siayltransferase to add terminal α-2,6-linked sialic acids. When necessary, it can be treated with β-1,4-galactosyltransferase to add a galactose and then with α-2,6-siayltransferase to add the terminal α-2,6-linked sialic acids. Preferably, the enzymes used in this method can be immobilized on a support member. In one example, α-fucosidase and α-2,6-siayltransferase are coated onto a plurality of beads and the resultant coated beads are packed in a column. A sample containing an antibody, either obtained from a commercial vendor or produced by a conventional method, is then loaded onto the column under conditions suitable for the enzymatic reactions catalyzed by the α-fucosidase and α-2,6-siayltransferase. The antibody, with core fucose removed and terminal sialic acid added, is then eluted by a suitable solution.

Example 2: Method B for Making Antibodies of the Invention

Alternatively, an antibody of this invention can be prepared following Path B described in FIG. 2. FIG. 2 shows an example for preparing an IgG antibody with its Fc region glycosylated with biantennary N-linked oligosaccharides. A human IgG antibody, having a glycosylated Fc region, was treated with sialidase and galactosidase, followed by Endo-H and alpha-fucosidase to produce an antibody having both Ig domains in the Fc region attached to a single GlcNAc residue. The antibody having two single GlcNAc residues attached (one in each of the Ig domains) is then subjected to endoglycosidase-catalyzed transglycosylation to elongate each of the GlcNAc residues to an oligosaccharide. In one example, a synthetic oligosaccharide with suitable leaving group like —OH, F or others is added to the GlcNAc mono-saccharide on the modified antibody via a glycosidase enzyme. Another example is a synthetic oligosaccharide with oxazoline group is added to the GlcNAc residue via an endo-beta-N-acetylglucosaminidase (NAG), endo-A or endo-M-mediated enzymatic reaction. The oligosaccharide is then treated with α-2,6-siayltransferase in the presence of CMP-Neu5Ac to add a terminal sialic acid residues. When necessary, a galactose residue is added to the oligosaccharide via β-1,4-galactosyltransferase, using UDP-Gal as a substrate, before addition of the sialic acids. In some embodiments, the UDP-galactose can be regenerated using the set of UDP-galactose regeneration enzymes. Useful UDP-galactose regeneration enzymes can include, for example, a glucose kinase, a phosphoglucomutase, an N-acetyl glucosamine-1 phosphate uridyltransferase, a polyphosphate kinase, a pyrophosphatase, a nucleoside diphosphate kinase, a UDP-Glc/GlcNAc$_4$ epimerase, a galactosyl transferase, a pyruvate kinase, a UDP kinase, a galactokinase, an ADP kinase, UDP-galactose pyrophosphorylase. In some embodiments, the CMP-Neu5Ac can be regenerated using a set of CMP-Neu5Ac regeneration enzymes. Useful CMP-Neu5Ac regeneration enzymes can include comprising a pyrophosphatase, a cytidine monophosphate kinase, a polyphosphate kinase, and a nucleoside diphosphate kinase.

Example 3: Method C for Making Antibodies of the Invention

An antibody of this invention can also be prepared following the process (i.e., Path C) depicted in FIG. 3. In this process, a human antibody with glycosylated Fc region can be first treated with one or more exo-glycosylases to remove core fucoses and to trim the original oligosaccharides attached to the Fc region to trisaccharides. The core fucose-free trisaccharides are then elongated by glysocyltransferases to desired oligosaccharides, e.g., having sugar sequences identical to those found in naturally occurring human antibodies. Finally, the desired oligosaccharides are treated with β-1,4-galactosyltrasferase and α-2,6-siayltransferase sequentially to add galactose residues and then terminal sialic acid residues.

Example 4: Methods for Cleaving the Chitobiose Linkage of Fc N-Linked Glycans

Endo F2 and Endo F3 are unique in their ability to cleave complex structures. Endo F2 cleaves asparagine-linked or free oligomannose, and biantennary complex oligosaccharides. Oligomannose structures are cleaved at a 20-fold reduced rate. Fucosylation has little effect on Endo F2 cleavage of biantennary structures. It will not cleave hybrid structures. It cleaves between the two N-acetylglucosamine residues in the diacetylchitobiose core of the oligosaccharide, generating a truncated sugar molecule with one N-acetylglucosamine residue remaining on the asparagine.

Endo F3 is unique in that its cleavage is sensitive to the state of peptide linkage of the oligosaccharide, as well as the state of core fucosylation. Endoglycosidase F3 cleaves asparagine-linked biantennary and triantennary complex oligosaccharides. It will cleave non-fucosylated biantennary and triantennary structures at a slow rate, but only if peptide-linked. Core fucosylated biantennary structures are efficient substrates for Endo F3, even as free oligosaccharides. Endo F3 will also cleave fucosylated trimannosyl core structures on free and protein-linked oligosaccharides.

As shown in FIG. 5A, Humira® obtained from CHO cells, comprises a heterogeneous population of glycoforms with a predominance of the fucosylated glycoform (GlcNAc-Man)$_2$-Man-GlcNAc-GlcNAc(Fucose)-[Fc].

Digestion with Endo F2 (in 0.05M NaH$_2$PO$_4$, pH 4.54 buffer) or Endo F3 (in 0.05M CH$_3$COONa, pH 4.54 buffer) yielded a glycoform with a single fucosylated GlcNAc as visualized by 8-16% polyacrylamide gel electrophoresis in Tris-glycine buffer with Coomassie Blue stain (FIG. 5B)

Example 5: Method for Glycan Engineering Antibodies

Rituximab that had been prepared from CHO cells was analyzed to quantitatively identify the glycan structures attached at Asn 297 of the Fc region. As shown in the table in FIG. 6, the N-glycan structures G2/G2F (Gal2GlcNAc2Man3GlcNAc2), G0/G0F (GlcNAc2Man3GlcNAc), and G1F/G1F' (GalGlcNAc2Man3GlcNAc) accounted for more than 90% of the glycan structures attached at Asn 297 of the Fc region. The G2/G2F structure made up 2.93% of the total; the G0/G0F structure made up 65.78% of the total, and the G1F/G1' made up 25.6% of the total. The Rituximab was converted to a formulation in which more than 90% of the glycan structures attached at Asn 297 of the Fc region had the structure G2S2/G2S2F (Neu5Ac2Gal2GlcNAc2Man3GlcNAc2) according to the method illustrated in the Neu5Ac2Gal2GlcNAc2Man3GlcNAc2. This method is illustrated in the flow diagram depicted at the top of FIG. 6. In step 1 of the method, Rituximab that had been prepared from CHO cells was contacted with UDP galactose and β-1,4-galactosyltransferase in order to couple the terminal GlcNac of the GalGlcNAc2Man3GlcNAc, and the GlcNAc2Man3GlcNAc to the galactose, resulting in a formulation ("intermediate") in which more than 90% of the 90% of the glycan structures attached at Asn 297 of the Fc region had the structure G2/G2F. In step 2 of the method, the "intermediate" was contacted with CMP-Neu5Ac (also referred to as CMP-sialic acid) and alpha-2,6-sialyltransferase in order to couple the terminal galactose of the intermediate to CMP-Neu5Ac. As shown in the Table, more than 90% of the final product was made up of Rituximab having a Neu5Ac2Gal2GlcNAc2Man3GlcNAc2 attached at each Asn 297 in the Fc region.

Figure 8:
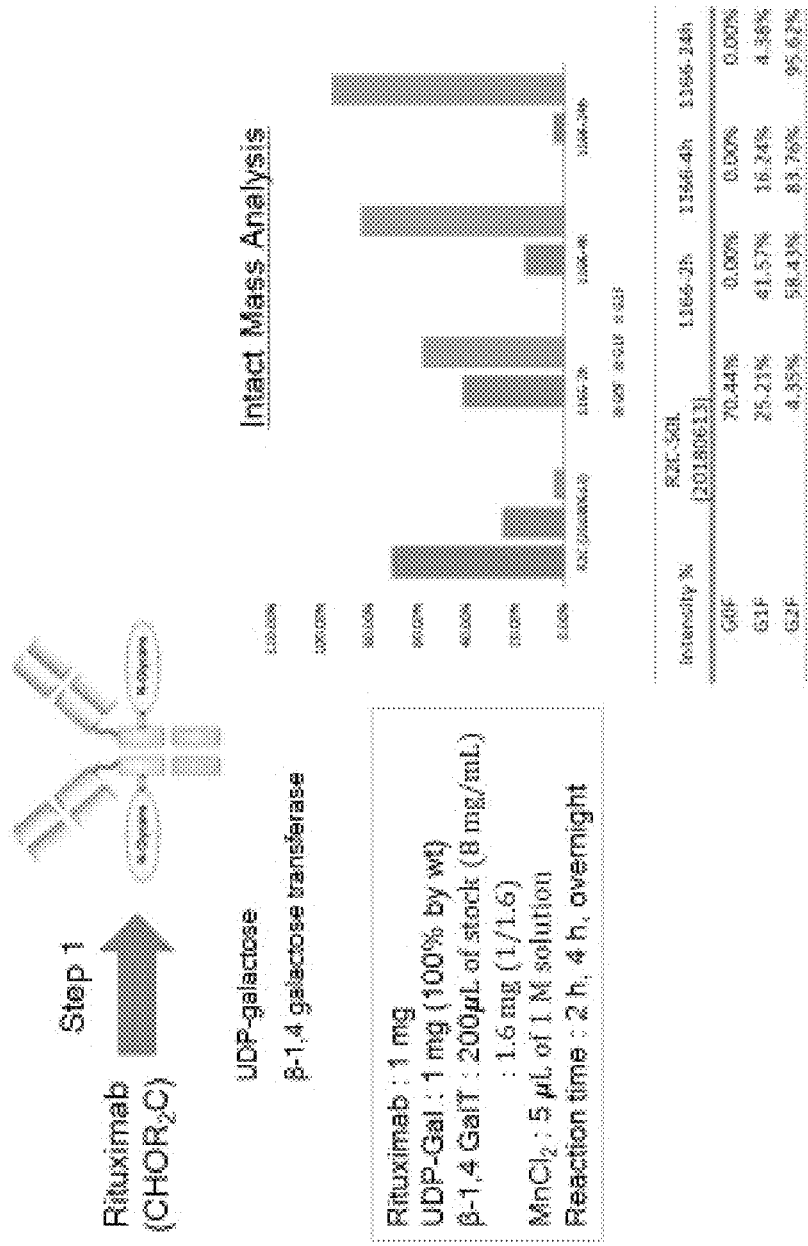
FIG. 8 depicts the results of treatment of Rituximab with β-1,4-galactosyltransferase and UDP galactose.

FIG. 8 depicts the results of a time course experiment in which Rituximab with β-1,4-galactosyltransferase and UDP galactose. Aliquots of Rituximab (1 mg) was treated with β-1,4-galactosyltransferase (1.6 mg) and UDP galactose (1 mg) for either 2 hours, 4 hours or overnight. Following treatment, the N-glycans were analyzed. As shown in the bar graph, there was a time-dependent increase the level of the G2F N-glycan and concomitant time-dependent decrease in the level of G1F N-glycan.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are encompassed within the scope of the claimed invention.

All publications and patent applications cited in this specification are herein incorporated by reference as if each individual publication or patent application were specifically and individually indicated to be incorporated by reference.

What is claimed is:

1. A method for engineering the glycan on the Fc region of a human, chimeric, or humanized glycosylated antibody, wherein the glycosylated antibody comprises an oligosaccharide attached at Asn-297, wherein the oligosaccharide includes or excludes a core fucose, the method comprising:
   (a) contacting the antibody with a β-1,4-galactosyltransferase and UDP galactose thereby coupling the terminal unit of the oligosaccharide to the galactose to form an oligosaccharide having a terminal galactose unit, wherein the oligosaccharide having a terminal galactose unit is attached at each Asn 297 of the Fc region of the human, chimeric or humanized glycosylated antibody; and
   (b) contacting the antibody comprising the oligosaccharide having a terminal galactose with an alpha-2,6-sialyltransferase and CMP-Neu5Ac, thereby adding a terminal Neu5Ac to each terminal galactose unit to form an oligosaccharide having a terminal Neu5Ac2Gal$_2$, wherein the oligosaccharide having a terminal Neu5Ac2Gal$_2$ is attached at each Asn 297 of the Fc region of the human, chimeric or humanized glycosylated antibody.

2. The method of claim 1, wherein the human, chimeric, or humanized glycosylated antibody comprises an IgG, IgE, IgA, IgD, or and IgM.

3. The method of claim 2, wherein the IgG is an IgG1, an IgG2, an IgG3, or an IgG4.

4. The method of claim 1, wherein the human, chimeric, or humanized glycosylated antibody is a therapeutic antibody selected from the group consist of ravulizumab, sacituzumab, risankizumab, emapalumab, cemiplimab, galcanezumab, fremanezumab, romosozumab, moxetumomab, caplacizumab, lanadelumab, mogamuizumab, erenumab, tildrakizumab, ibalizumab, burosumab, durvalumab, emicizumab, benralizumab, ocrelizumab, guselkumab, inotuzumab, sarilumab, dupilumab, avelumab, brodalumab, atezolizumab, bezlotoxumab, olaratumab, reslizumab, obiltoxaximab, ixekizumab, daratumumab, elotuzumab, necitumumab, idarucizumab, alirocumab, mepolizumab, evolocumab, dinutuximab, secukinumab, nivolumab, blinatumomab, pembrolizumab, ramucirumab, vedolizumab, siltuximab, obinutuzumab, trastuzumab, raxibacumab, pertuzumab, brentuximab, belimumab, ipilimumab, denosumab, tocilizumab, ofatumumab, canakinumab, golimumab, ustekinumab, certolizumab, catumaxomab, eculizumab, ranibizumab, panitumumab, natalizumab, bevacizumab, cetuximab, efalizumab, omalizumab, tositumomab, ibritumomab, adalimumab, alemtuzumab, gemtuzumab, trastuzumab, infliximab, palivizumab, basiliximab, daclizumab, rituximab, abciximab, edrecolomab, nebacumab, and muromonab.

5. The method of claim 1, wherein the oligosaccharide attached at Asn-297 is selected from the group consisting of Gal₂GlcNAc₂Man₃GlcNAc₂, GalGlcNAc₂Man₃GlcNAc₂, and GlcNAc₂Man₃GlcNAc₂.

6. The method of claim 1, wherein the terminal unit of the oligosaccharide comprises a GlcNAc.

7. The method of claim 1, wherein the oligosaccharide of step (a) having a terminal galactose unit attached at each Asn 297 of the Fc region of the human, chimeric or humanized glycosylated antibody is Gal₂GlcNAc₂Man₃GlcNAc₂.

8. The method of claim 1, wherein the glycan engineered human, chimeric or humanized antibody of step (b) has a Neu5Ac2Gal₂GlcNAc₂Man₃GlcNAc₂ attached at each Asn 297 in the Fc region.

9. The method of claim 1, wherein the β-1,4-galactosyltransferase and the alpha-2,6-sialyltransferase are immobilized on a solid support.

10. The method of claim 9, wherein the solid support is a bead.

11. The method of claim 1, further comprising a set of CMP-Neu5Ac regeneration enzymes comprising a pyrophosphatase and a cytidine monophosphate kinase, and wherein the CMP-Neu5Ac is regenerated following the addition of the terminal Neu5Ac.

12. The method of claim 1, further comprising purifying the glycan engineered human, chimeric or humanized antibody.

13. A method for glycan engineering the Fc region of a human, chimeric, or humanized glycosylated antibody, wherein the glycosylated antibody comprises an oligosaccharide attached at each Asn-297, wherein the oligosaccharide has the following structure:

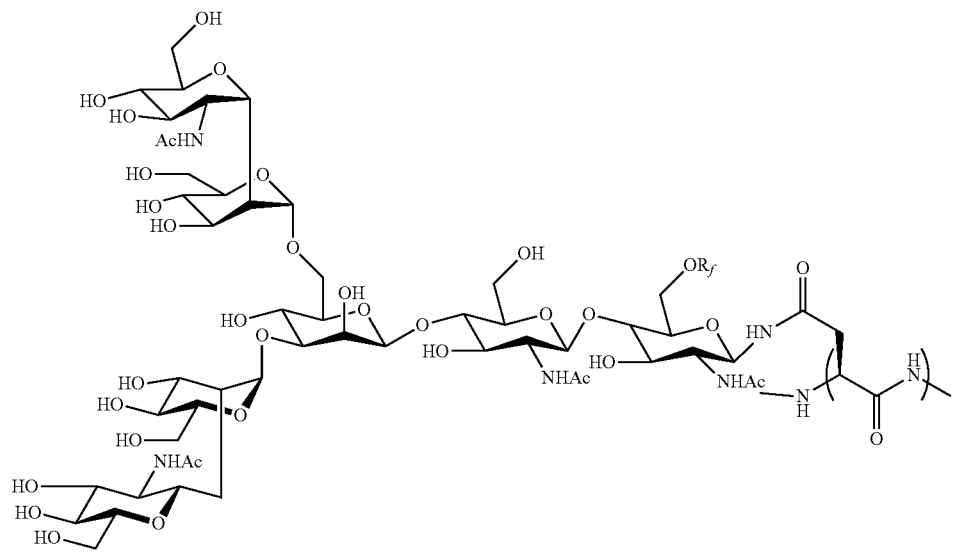

wherein $R_f$ is selected from H or

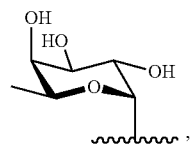

the method comprising:
(a) reacting UDP galactose with the oligosaccharide having the structure:

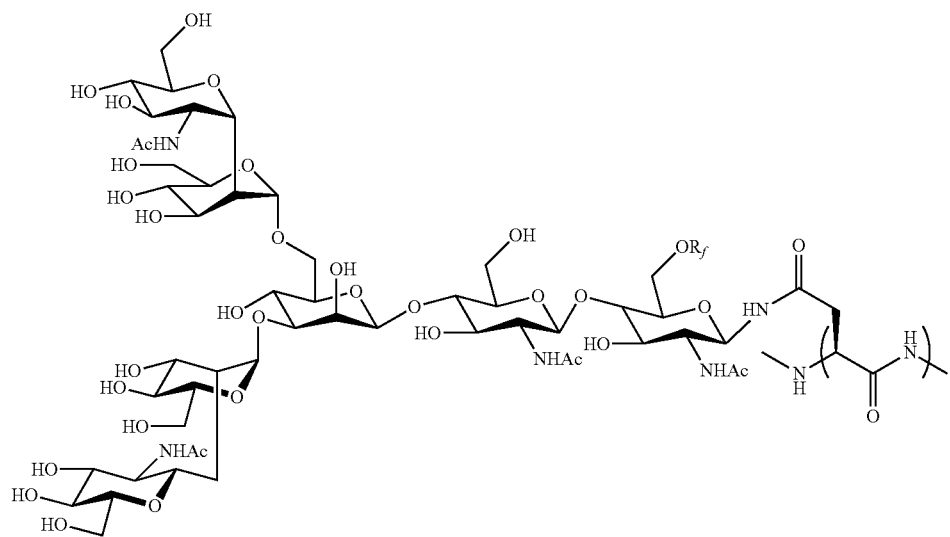
using β-1,4-galactosyltransferase as an enzymatic catalyst to form a Gal$_2$-oligosaccharide having the structure:
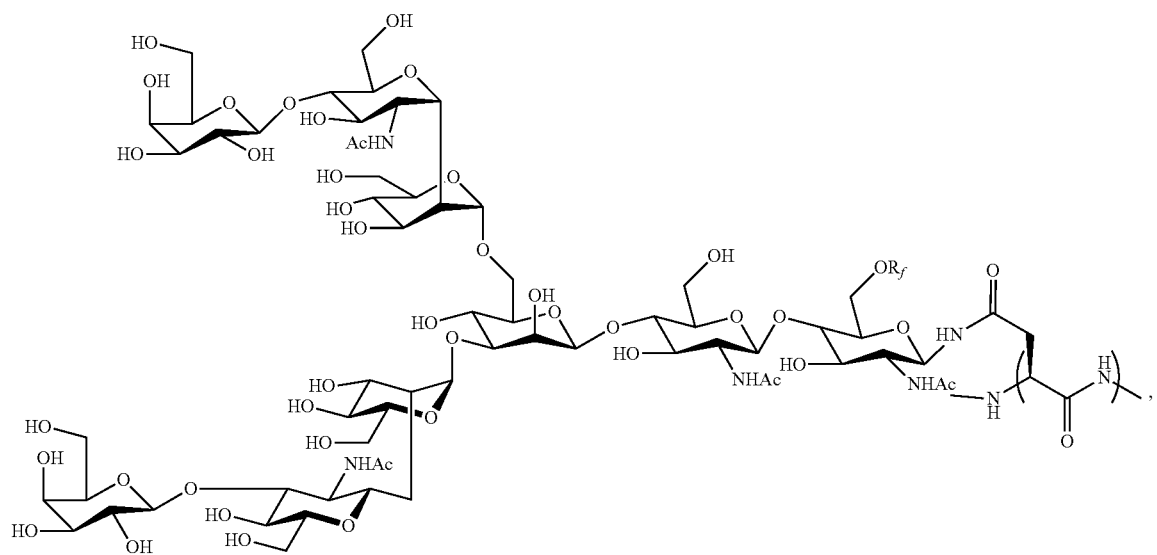

and
(b) reacting the Gal$_2$-oligosaccharide having the structure:
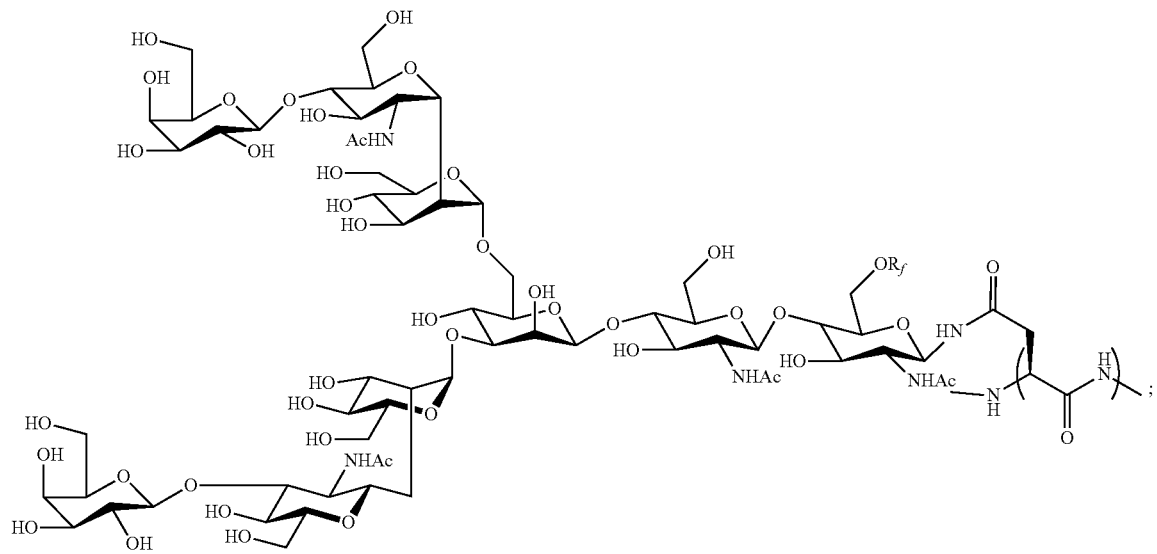
with a compound having the structure:
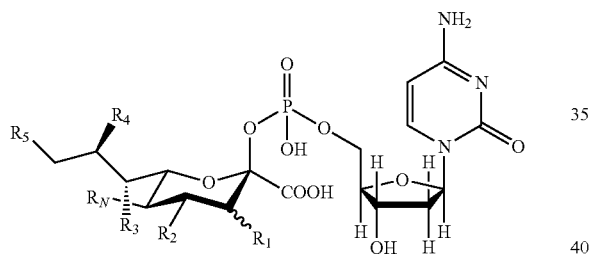
using an alpha-2,6-sialyltransferase as the enzymatic catalyst to form a glycan having the structure:
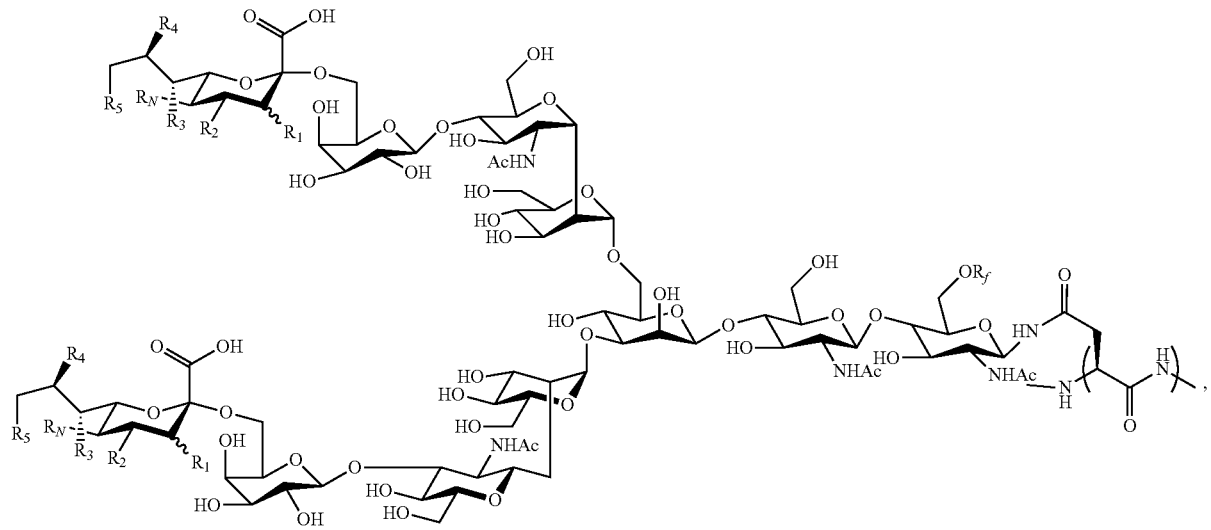

wherein:

$R_1$ is selected from hydrogen or hydroxy;

each instance of $R_2$, $R_3$, $R_4$, and $R_5$ is independently selected from hydrogen, halogen, optionally substituted alkyl, optionally substituted alkenyl, optionally substituted alkynyl, optionally substituted heterocyclyl, optionally substituted aryl, —$N_3$, —$NO_2$, —$N(R_B)_2$, —$N(R_A)C(O)R_A$, —$OR_A$, —$OC(O)R_A$, —$SR_A$, —$C(O)N(R_B)_2$, —CN, —$C(O)R_A$, —$C(O)OR_A$, —$S(O)R_A$, —$SO_2R_A$, —$SO_2N(R_B)_2$, and —$NHSO_2R_B$;

$R_N$ is selected from —$N_3$, —$NO_2$, —$N(R_B)_2$, —$N(R_A)C(O)R_A$, —$OR_A$, —$OC(O)R_A$, —$SR_A$, —$C(O)N(R_B)_2$, —CN, —$C(O)R_A$, —$C(O)OR_A$, —$S(O)R_A$, —$SO_2R_A$, —$SO_2N(R_B)_2$, and —$NHSO_2R_B$;

each instance of $R_A$ is independently selected from hydrogen, optionally substituted alkyl, optionally substituted alkenyl, optionally substituted alkynyl, optionally substituted heterocyclyl, and optionally substituted aryl; and each instance of $R_B$ is independently selected from hydrogen, optionally substituted alkyl, optionally substituted alkenyl, optionally substituted alkynyl, optionally substituted heterocyclyl, and optionally substituted aryl.

14. The method of claim 13, wherein the compound having the structure:

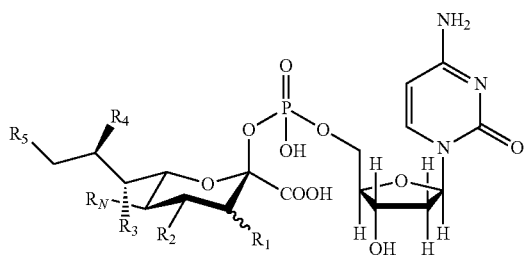

is formed by a reaction comprising the enzymes consisting of a pyrophosphatase and a cytidine monophosphate kinase.

15. The method of claim 14, wherein $R_1$ is hydrogen, $R_2$ is hydroxyl, $R_3$ is hydroxyl, $R_4$ is hydroxyl, $R_5$ is hydroxyl, $R_N$ is NHAc, and $R_f$ is hydrogen.

16. The method of claim 13, wherein the human, chimeric, or humanized glycosylated antibody comprising the oligosaccharide attached at Asn-297 excludes a core fucose.

17. A pharmaceutical formulation comprising an antibody of claim 13, wherein the antibody has the glycan structure of: $Sia_2(\alpha 2\text{-}6)Gal_2GlcNAc_2Man_3GlcNAc_2$ attached to the Asn-297 of the Fc region.

18. A method for engineering the glycan on the Fc region of a human, chimeric, or humanized glycosylated antibody, wherein the glycan has the structure of:

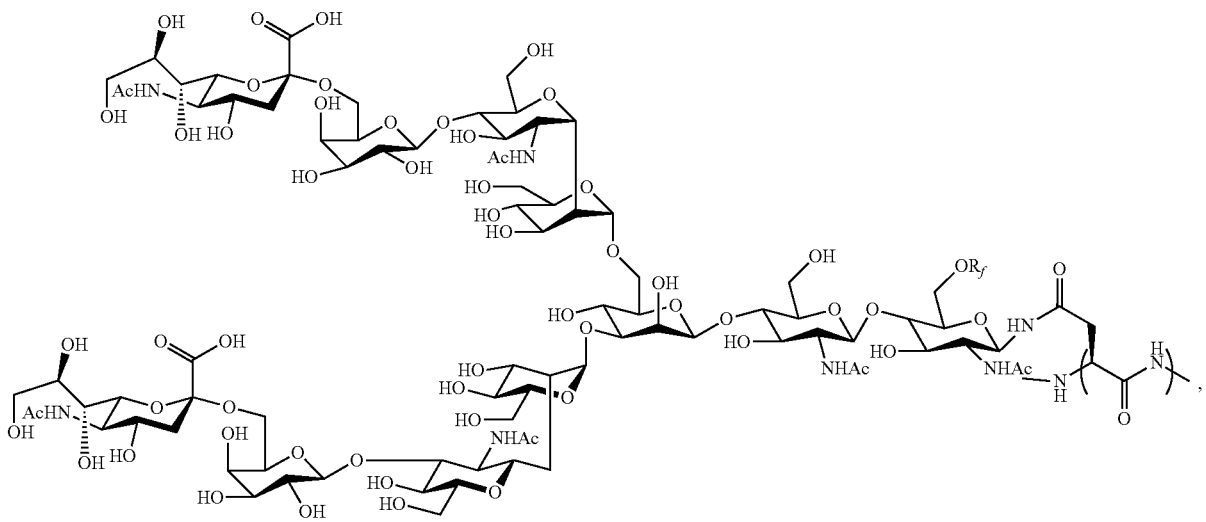

wherein $R_f$ is selected from H or

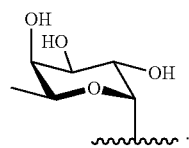

19. A method for engineering the glycan on the Fc region of a human, chimeric, or humanized glycosylated antibody, wherein the glycosylated antibody comprises an oligosaccharide attached at Asn-297, the method comprising:

(a) providing a human, chimeric, or humanized glycosylated antibody;

(b) contacting the antibody with a β-1,4-galactosyltransferase and UDP galactose thereby coupling the terminal unit of the oligosaccharide to the galactose to form an oligosaccharide having a terminal galactose unit, wherein the oligosaccharide having a terminal galactose unit is attached at each Asn 297 of the Fc region of the human, chimeric or humanized glycosylated antibody; and (c) contacting the antibody comprising the oligosaccharide having a terminal galactose with an alpha-2,6-sialyltransferase and CMP-Neu5Ac, thereby adding a terminal Neu5Ac to each terminal galactose unit to form an oligosaccharide having a terminal Neu5Ac2Gal2, wherein the oligosaccharide having a terminal Neu5Ac2Gal2 is attached at each Asn 297 of the Fc region of the human, chimeric or humanized glycosylated antibody.

20. The method of claim 19, wherein the human, chimeric, or humanized glycosylated antibody comprises an IgG, IgE, IgA, IgD, or and IgM.

21. The method of claim 20, wherein the IgG is an IgG1, an IgG2, an IgG3, or an IgG4.

22. The method of claim 19, wherein the human, chimeric, or humanized glycosylated antibody is a therapeutic antibody selected from the group consist of ravulizumab, sacituzumab, risankizumab, emapalumab, cemiplimab, galcanezumab, fremanezumab, romosozumab, moxetumomab, caplacizumab, lanadelumab, mogamuizumab, erenumab, tildrakizumab, ibalizumab, burosumab, durvalumab, emicizumab, benralizumab, ocrelizumab, guselkumab, inotuzumab, sarilumab, dupilumab, avelumab, brodalumab, atezolizumab, bezlotoxumab, olaratumab, reslizumab, obiltoxaximab, ixekizumab, daratumumab, elotuzumab, necitumumab, idarucizumab, alirocumab, mepolizumab, evolocumab, dinutuximab, secukinumab, nivolumab, blinatumomab, pembrolizumab, ramucirumab, vedolizumab, siltuximab, obinutuzumab, trastuzumab, raxibacumab, pertuzumab, brentuximab, belimumab, ipilimumab, denosumab, tocilizumab, ofatumumab, canakinumab, golimumab, ustekinumab, certolizumab, catumaxomab, eculizumab, ranibizumab, panitumumab, natalizumab, bevacizumab, cetuximab, efalizumab, omalizumab, tositumomab, ibritumomab, adalimumab, alemtuzumab, gemtuzumab, trastuzumab, infliximab, palivizumab, basiliximab, daclizumab, rituximab, abciximab, edrecolomab, nebacumab, and muromonab.

23. The method of claim 19, wherein the oligosaccharide attached at Asn-297 is selected from the group consisting of $Gal_2GlcNAc_2Man_3GlcNAc_2$, $GalGlcNAc_2Man_3GlcNAc_2$, and $GlcNAc_2Man_3GlcNAc_2$.

24. The method of claim 19, wherein the terminal unit of the oligosaccharide comprises a GlcNAc.

25. The method of claim 19, wherein the oligosaccharide of step (a) having a terminal galactose unit attached at each Asn 297 of the Fc region of the human, chimeric or humanized glycosylated antibody is $Gal_2GlcNAc_2Man_3GlcNAc_2$.

26. The method of claim 19, wherein the glycan engineered human, chimeric or humanized antibody of step (b) has a $Neu5Ac2Gal_2GlcNAc_2Man_3GlcNAc_2$ attached at each Asn 297 in the Fc region.

27. A method for making an essentially pure population of glycoengineered human, chimeric, or humanized glycosylated antibodies from a population of precursor human, chimeric, or humanized glycosylated antibodies, wherein the precursor glycosylated antibodies have an oligosaccharide attached at Asn-297, the method comprising:
(a) contacting the precursor antibodies with a β-1,4-galactosyltransferase and UDP galactose thereby coupling the terminal unit of the oligosaccharide to the galactose to form an oligosaccharide having a terminal galactose unit, wherein the oligosaccharide having a terminal galactose unit is attached at each Asn 297 of the Fc region of the human, chimeric or humanized glycosylated antibody; and
(b) contacting the antibodies comprising the oligosaccharide having a terminal galactose with an alpha-2,6-sialyltransferase and CMP-Neu5Ac, thereby adding a terminal Neu5Ac to each terminal galactose unit to form an oligosaccharide having a terminal Neu5Ac2Gal2, wherein the oligosaccharide having a terminal Neu5Ac2Gal2 is attached at each Asn 297 of the Fc region of the human, chimeric or humanized glycosylated antibodies, and wherein the essentially pure population of glycoengineered human, chimeric, or humanized glycosylated antibodies comprises at least about 85% by weight of the glycoengineered human, chimeric, or humanized glycosylated antibodies.

28. The method of claim 27, wherein the human, chimeric, or humanized glycosylated antibodies comprise an IgG, IgE, IgA, IgD, or and IgM.

29. The method of claim 28, wherein the IgG is an IgG1, an IgG2, an IgG3, or an IgG4.

30. The method of claim 27, wherein the human, chimeric, or humanized glycosylated antibodies are therapeutic antibodies selected from the group consisting of ravulizumab, sacituzumab, risankizumab, emapalumab, cemiplimab, galcanezumab, fremanezumab, romosozumab, moxetumomab, caplacizumab, lanadelumab, mogamuizumab, erenumab, tildrakizumab, ibalizumab, burosumab, durvalumab, emicizumab, benralizumab, ocrelizumab, guselkumab, inotuzumab, sarilumab, dupilumab, avelumab, brodalumab, atezolizumab, bezlotoxumab, olaratumab, reslizumab, obiltoxaximab, ixekizumab, daratumumab, elotuzumab, necitumumab, idarucizumab, alirocumab, mepolizumab, evolocumab, dinutuximab, secukinumab, nivolumab, blinatumomab, pembrolizumab, ramucirumab, vedolizumab, siltuximab, obinutuzumab, trastuzumab, raxibacumab, pertuzumab, brentuximab, belimumab, ipilimumab, denosumab, tocilizumab, ofatumumab, canakinumab, golimumab, ustekinumab, certolizumab, catumaxomab, eculizumab, ranibizumab, panitumumab, natalizumab, bevacizumab, cetuximab, efalizumab, omalizumab, tositumomab, ibritumomab, adalimumab, alemtuzumab, gemtuzumab, trastuzumab, infliximab, palivizumab, basiliximab, daclizumab, rituximab, abciximab, edrecolomab, nebacumab, and muromonab.

31. The method of claim 27, wherein the oligosaccharide attached at Asn-297 is selected from the group consisting of $Gal_2GlcNAc_2Man_3GlcNAc_2$, $GalGlcNAc_2Man_3GlcNAc_2$, and $GlcNAc_2Man_3GlcNAc_2$.

32. The method of claim 27, wherein the terminal unit of the oligosaccharide comprises a GlcNAc.

33. The method of claim 27, wherein the oligosaccharide of step (a) having a terminal galactose unit attached at each Asn 297 of the Fc region of the human, chimeric or humanized glycosylated antibody is $Gal_2GlcNAc_2Man_3GlcNAc_2$.

34. The method of claim 27, wherein the glycan engineered human, chimeric or humanized antibody of step (b) has a $Neu5Ac2Gal_2GlcNAc_2Man_3GlcNAc_2$ attached at each Asn 297 in the Fc region.

35. The method of claim 27, wherein the essentially pure population of glycoengineered human, chimeric, or humanized glycosylated antibodies comprises at least about 85% by weight of the glycoengineered human, chimeric, or humanized glycosylated antibodies.

36. The method of claim 27, wherein the essentially pure population of glycoengineered human, chimeric, or humanized glycosylated antibodies comprises at least about 90% by weight of the glycoengineered human, chimeric, or humanized glycosylated antibodies.

* * * * *